US007919132B2

(12) United States Patent
Regina et al.

(10) Patent No.: US 7,919,132 B2
(45) Date of Patent: Apr. 5, 2011

(54) BARLEY WITH ALTERED BRANCHING ENZYME ACTIVITY AND STARCH AND STARCH CONTAINING PRODUCTS WITH AN INCREASED AMYLOSE CONTENT

(75) Inventors: Ahmed Regina, Ngunnawal (AU); Matthew Kennedy Morell, Aranda (AU); Sadequr Rahman, Melba (AU)

(73) Assignee: Commonwealth Scientific and Industrial Research Organisation, Campbell (AU)

(*) Notice: Subject to any disclaimer, the term of this patent is extended or adjusted under 35 U.S.C. 154(b) by 0 days.

(21) Appl. No.: 12/384,823

(22) Filed: Apr. 9, 2009

(65) Prior Publication Data
US 2009/0226592 A1    Sep. 10, 2009

Related U.S. Application Data

(62) Division of application No. 10/434,893, filed on May 9, 2003, now Pat. No. 7,521,593.

(30) Foreign Application Priority Data

May 9, 2002    (AU) ............................................. 2198

(51) Int. Cl.
A23L 1/10      (2006.01)
B02C 23/06    (2006.01)
C12N 15/82    (2006.01)
A01H 5/00      (2006.01)
A01H 5/10      (2006.01)

(52) U.S. Cl. ........ 426/518; 426/615; 426/622; 800/320; 435/440

(58) Field of Classification Search .................. 426/622, 426/549, 589, 518, 615, 665
See application file for complete search history.

(56) References Cited

U.S. PATENT DOCUMENTS

| | | | |
|---|---|---|---|
| 3,690,896 A * | 9/1972 | Maxwell | 426/249 |
| 4,770,710 A | 9/1988 | Friedman et al. | |
| 5,792,920 A * | 8/1998 | Bridges et al. | 800/284 |
| 6,013,861 A | 1/2000 | Bird et al. | |
| 6,303,174 B1 | 10/2001 | McNaught et al. | |
| 6,307,125 B1 | 10/2001 | Block et al. | |
| 6,376,749 B1 * | 4/2002 | Broglie et al. | 800/284 |
| 6,483,009 B1 | 11/2002 | Poulsen et al. | |
| 6,734,339 B2 | 5/2004 | Block et al. | |
| 6,897,354 B1 | 5/2005 | Yamamori et al. | |
| 6,916,976 B1 | 7/2005 | Li et al. | |
| 7,001,771 B1 | 2/2006 | Morell et al. | |
| 7,041,484 B1 | 5/2006 | Baga et al. | |
| 7,521,593 B2 | 4/2009 | Regina et al. | |
| 2004/0060083 A1 | 3/2004 | Regina et al. | |
| 2004/0199942 A1 | 10/2004 | Morell et al. | |
| 2005/0071896 A1 | 3/2005 | Regina et al. | |
| 2006/0010517 A1 | 1/2006 | Li et al. | |
| 2006/0035379 A1 | 2/2006 | Morell et al. | |
| 2006/0204597 A1 | 9/2006 | Bird et al. | |
| 2006/0286186 A1 | 12/2006 | Bird et al. | |
| 2007/0300319 A1 | 12/2007 | Li et al. | |

FOREIGN PATENT DOCUMENTS

| | | |
|---|---|---|
| GB | 2360521 | 9/2001 |
| WO | WO97/22703 | 6/1997 |
| WO | WO00/15810 | 3/2000 |
| WO | WO00/66745 | 11/2000 |
| WO | WO01/32886 | 5/2001 |
| WO | WO01/62934 | 8/2001 |
| WO | WO02/37955 | 5/2002 |
| WO | WO02/101059 | 12/2002 |
| WO | WO03/023024 | 3/2003 |
| WO | WO03/094600 | 11/2003 |
| WO | WO2005/001098 | 1/2005 |
| WO | WO2005/040381 | 5/2005 |

OTHER PUBLICATIONS

Tetlow. Recent developments in understanding the regulation of starch metabolism in higher plants. 2004. Journal of Experimental Botany, vol. 55:406, pp. 2131-2145.*
Abel et al., GenBank Accession #Y10416 (Jan. 1997) S. Tuberosum mRNA for Soluble Starch Synthase.
Ainsworth, C. et al., "Expression, organization and structure of the genes encoding the waxy protein (granule-bound starch synthase) in wheat," Plant Mol. Biol. 22:67-82 (1993).
Baba, T. et al., "Identification, cDNA cloning and gene expression of soluble starch synthase in rice (oryza stativa L.) Immature Seeds," Plant Physiol. 103:565-573.
Banks et al., "Studies on Starches of High Amylose Content," Starch 26: 289-300 (1974).
Batey and Curtin, "Measurement of Amylose/Amylopectin Ratio by High-Performance Liquid Chromatography," Starch 48: 338-344 (1996).
Bhullar et al., GenBank Accession #CAB40374 (Apr. 1999) Starch synthase isoform SS III [Vigna unguiculata].
Block et al., GenBank Accession #U48227 (Jun. 1996) Triticum aestivum soluble starch synthase mRNA, partial cds.
Boyer and Preiss, "Evidence for Independent Genetic Control of the Multiple Forms of Maize Endosperm Branching Enzymes and Starch Synthases," Plant Physiology 67: 1141-1145 (1981).
Buleon et al., "Starch Granules: Structure and Biosynthesis," International Journal of Biological Macromolecules 23: 85-112 (1998).
Craig et al., "Mutations in the Gene Encoding Starch Synthase II Profoundly Alter Amylopectin Structure in Pea Embryos," The Plant Cell 10:413-426 (1998).
Denyer, K. et al., "Identification of Multiple Isoforms of Soluble and Granule Bound Starch Synthase in Developing Wheat Endosperm," Planta 196: 256-265 (1995).

(Continued)

Primary Examiner — Rena L Dye
Assistant Examiner — Saeeda Latham
(74) Attorney, Agent, or Firm — John P. White; Cooper & Dunham LLP

(57) ABSTRACT

Barley having a reduced level of SBEIIa activity produces grain having a high relative amylose content. The barley might additionally have reduced levels of SBEIIb activity. The barley grain of this invention can be of a non-shrunken phenotype despite a lesion in the amylopectin synthesis pathway.

17 Claims, 18 Drawing Sheets

OTHER PUBLICATIONS

Dry, I. et al., "Characterization of cDNAs encoding two isoforms of granule-bound synthase which show differential expression in developing storage organs of pea and potato, " Plant J. 2(2): 193-202 (1992).

Edwards et al., "Biochemical and Molecular Characterization of a Novel Starch Synthase from Potato Tubers, " Plant J. 8(2): 283-294 (1995).

Flipse et al., "Introduction of Sense and Antisense cDNA for Branching Enzyme in the Amylose-Free Potato Mutant Leads to Physico-Chemical Changes in the Starch," Planta 198: 340-347 (1996).

Fujita et al., "Grain and Starch Characteristics of the Double Recessive Lines for Amylose-free and High Amylose Gene in Barley," Breeding Science 49: 217-219 (1999).

Gao et al., GenBank Accession #AAC14014 (Apr. 1998) Starch synthase DULL 1 [Zea mays].

Gao et al., GenBank Accession #AAC14015 (Apr. 1998) Starch synthase DULL 1 [Zea mays].

Gao et al., "Characterization of dull I, a Maize Gene Coding for a Novel Starch Synthase, " Plant Cell 10:399-412 (1998).

Gao et al., GenBank Accession #AJ26502 (Apr. 2002) Triticum aestivum mRNA for starch synthase Iia-1 (wSs2a-1 gene).

Gao et al., GenBank Accession #CAB86618 (Apr. 2002) Starch synthase Iia-1 [Triticum aestivum].

Goering and DeHass, "A Comparison of the Properties of Large- and Small-Granule Starch Isolated from Several Isogenic Lines of Barley," Cereal Chemistry 51:573-578 (1974).

Harn et al., "Isolation and Characterization of the zSSIIA and zSSIIb Starch Synthase cDNA Clones from Maize Endosperm," Plant Mol. Biol. 37:639-649 (1998).

Holmes et al., Henderson's Dictionary of Biological Terms, 9th Ed., Van Nostrand Reinhold Co., New York, 1979, p. 218.

Jarvi and Eslick, "Shrunken Endosperm Mutants in Barley." Crop Science 15:363-366 (1975).

Klosgen, et al., "Molecular Analysis of the Waxy Locus of Zea mays, "Mol. Gen. Genet. 203: 237-244 (1986).

Knight, et al., "Molecular Cloning of Starch Synthase I from Maize (w64) Endosperm and Expression in *Escherichia coli*," Plant J. 14(5): 613-622 (1998).

Kull et al., "Genetic Engineering of Potato Starch Composition: Inhibition of Amylose Biosynthesis in Tubers from Transgenetic Potato Lines by the Expression of Antisense Sequences of the Gene for Granule-bound Starch Synthase," J. Genet. Breed. 49:69-76 (1995).

Li et al., "Cloning and Characterization of a Gene Encoding Wheat Starch Synthase I," Theor. AEEI. Genet. 98: 1208-1216 (1999).

Mazzolini et al., "Assaying synthetic ribozymes in plants: high-level expression of a functional hammerhead structure fails to inhibit taget gene activity in transiently transformed protoplasts, " Plant Mol. Biol. 20:715-731 (1992).

Morell et al., "The Biochemistry and Molecular Biology of Starch Synthesis in Cereals," Aust. J. Plant. Physiol. 22: 647-660 (1995).

Okagaki R. J., "Nucleotide Sequence of a Long cDNA from the Rice Waxy Gene," Plant Molecular Biology 19: 513-516 (1992).

Puchta, "Gene Replacement by Homologous Recombination in Plants," Plant Mol. Biol. 48:173-182 (2002).

Rahman et al., GenBank Accession #AF076680 (May 1999) Aegilops tauschii starch branching enzyme-I (SBE-1) gene, complete cds.

Rahman, S. et al., "A Complex Arrangement of Genes at a Starch Branching Enzyme I Locus in the D-genome Donor of wheat," Genome 40: 465-474 (1997).

Rahman, S. et al., "Characterisation of a Gene Encoding Wheat Endosperm Starch Branching Enzyme-I, " Theor. Appl. Genet. 98: 156-163 (1999).

Rahman, S. et al. The major proteins of wheat starch granules. Proceedings of the 45th Australian Cereal Chemistry Conference. (Eds Williams Y A. and Wrigley, C.W.) pp. 133-134 (1995).

Safford, et al., "Consequences of Antisense RNA Inhibition of Starch Branching Enzyme Activity on Properties of Potato Starch," Carbohydrate Polymers 35: 155-168 (1998).

Schwall, et al., "Production of Very-High-Amylose Potato Starch by Inhibition of SBE A and B," Nature Biotechnology 18: 551-554 (2000).

Shannon and Garwood, "In Starch: Chemistry and Technology," Whistler et al., eds, Academic Press, Orlando, FL, 25-86 (1984).

Sidebottom, et al., "Characterization of the Difference of Starch Branching Enzyme Activities in Normal and Low-Amylopectin Maize during Kernel Development," Journal of Cereal Science 27: 279-287 (1998).

Takaoka, M. et al., "Structural characterization of high: molecular weight starch granule-bound proteins in wheat (Triticum aestivum L.)," J. Agric. Food Chem. 45: 2929-2934 (1997).

Terada at al., "Efficient Gene Targeting by Homologous Recombination in Rice," Nature Biotech. 20: 1030-1034 (1997).

Thomas, et al. , "Size Constraints for Targeting Post-Transcriptional Gene Silencing and for RNA-directed Methylation in Nicotiana benthamiana Using a Potato Virus X Vector," Plant J. 25: 417-425 (2001).

Van der Leij et al., "Sequence of the Structural Gene for Granule-Bound Starch Synthase of Potato (Solanum Tuberosum L.) and Evidence for a Single Point Deletion in the amf allele, " Mol. Gen. Genet. 228: 240-248.

Walter et al., GenBank Accession #AAB17085 (Oct. 1996) Starch Synthase.

Walter et al., GenBank Accession #U66377 (Oct. 1996) Triticum aestivum soluble starch synthase mRNA; partial cd.

Yamamori and Endo, "Variation of Starch Granule Proteins and Chromosome Mapping of Their Coding Genes in Common Wheat," Theor. Appl. Genet. 93: 275-181 (1996).

Yamamori et al., "Genetic Elimination of a Starch Granule Protein, SGP-1, of Wheat Generates an Altered Starch with Apparent High Amylose," Theor. Appl. Genet. 101: 21-29 (2000).

Yamamori, "Selection of a Wheat Lacking a Putative Enzyme for Starch Synthesis, SGP-1," Proc. 9th in Wheat Gen. Symp. 4:300-302 (1998).

Sathish et al., "Cloning and Anti-Sense RNA Constructs of a Starch Branching Enzyme Gene From Barley Endosperm." Photosynthesis: from Light to Biosphere vol. V, P. Mathis (ed.) pp. 313-316 (1995).

Schondelmaier et al., "Genetical Studies in the Mode of Inheritance and Localization of the amol (High Amylose) Gene in Barley." Plant Breeding 109: 274-280 (1992).

Sun et al., Identification of Four Starch-Branching Enzymes in Barley Endosperm: Partial Purification of forms I, IIa and IIb. New Phytol. 137:215-222 (1997).

Sun et al., "The Two Genes Encoding Starch-Branching Enzymes IIa and IIb Are Differentially Expressed in Barley." Plant Physiol. 118:37-49 (1998).

Andersson A. A. M. et al. "Starch and By-Products from a Laboratory-Scale Barley Starch Isolation Procedure" Cereal Chemistry 78(5):507-513 (2001).

Supplementary Search Report issued by the European Patent Office on Jul. 11, 2007 in connection with PCT International Application No. PCT/AU03/00565.

Blauth et al., Identification of Mutator Insertional Mutants of Starch-Branching Enzyme 2a in Corn. Plant Physiol. 125:1396-1405 (2001).

Jansson et al., Cloning, Characterization and Modification of Genes Encoding Starch Branching Enzymes in Barley. *Starch: Structure and Functionality*. Royal Society of Chemistry, London, pp. 196-203 (1997).

Mizuno et al., Alteration of the Structural Properties of Starch Compounds by the Lack of an Isoform of Starch Branching Enzyme in Rice Seeds. *J. Biol. Chem.* 268(25):19084-19091(1993).

Morell et al., Barley *sex6* mutants lack starch synthase IIa activity and contain a starch with novel properties. *The Plant Journal*. 34:173-185 (2003).

Nishi et al., Biochemical and Genetic Analysis of the Effects of the Effects *Amylose-Extender* Mutation in Rice Endosperm. *Plant Physiol*. 127:459-472 (2001).

Feb. 10, 2005 International Search Report issued by the International Searching Authority (ISA/AU) in connection with International Application No. PCT/AU04/001517.

Jan. 3, 2006 International Preliminary Examination Report issued Jan. 12, 2006 by the International Bureau of WIPO in connection with PCT International Application No. PCT/AU2004/000901.

Craig et al., "Mutations in the Gene Encoding Starch Synthase II Profoundly Alter Amylopectin Structure in Pea Embryos," The Plant Cell 10:413-426 (1998).

EMBL Abstract Accession No. AJ269503, Jul. 6, 2000, Triticum aestivum mRNA for starch synthase IIa-2 (wSs2a-2 gene).

EMBL Abstract Accession No. AF155217, Sep. 7, 1999, Triticum aestivum starch synthase IIa mRNA, complete cds.

Gao and Chibbar, "Isolation, characterization, and expression analysis of starch synthase IIa cDNA from wheat (Triticum aestivum L.)," Genome 43:768-775 (2000).

Li et al., "The Localization and Expression of the Class II Starch Synthases of Wheat," Plant Physiology, 120:1147-1155 (1999).

Miao et al., "Evaluation and Chaaracterization of an Endosperm-Specific sbeIIa Promoter in Wheat," Chinese Science Bulletin 49(6): 579-585 (2004).

Myers et al., "Recent Progress Toward Understanding Biosynthesis of the Amylopectin Crystal," Plant Physiology: 122: 989-997 (2000).

Nakamura Y., Towards a Better Understanding of the Metabolic System for Amylopectin Biosynthesis in Plants: Rice Endosperm as s Model Tissue. Plant Cell Physiol. 43(7):718-725 (2002).

Rahman, Sadequr et al., "Comparison of Startch-Branching Enzyme Genes Reveals Evolutionary Relationships Among Isoforms. Characterization of a Gene for Starch-Branching Enzyme IIa from the Wheat D Genome Donor Aegilops tauschii," Plant Physiology, 125: 1314-1324.

Sundberg et al., "Glycaemic Responses and Hypocholesterolaemic Effects of High-Amylose Barley Diets on Broiler Chicks," J. Sci. Food Agric. 76: 457-463 (1998).

Vrinten and Nakamura, "Wheat Granule-Bound Starch Synthase I and II Are Encoded by Separate Genes That Are Expressed in Different Tissues," Plant Physiology, 122:255-263 (2000).

National Plant Germplasm System (http://www.ars-grin.gov/npgs/), GRIN System Accession No. GSHO 2476, Jun. 23, 1997).

Tetlow et al. Recent Developments in Misunderstanding the Regulation of Starch Metabolism in Higher Plants. Journal of Experimental Botany 55 (406): 2131-2145 (2004).

Andersson A. A. M. et al. "Starch and By-Products from a Laboratory-Scale Barley Starch Isolation Procedure" Cereal Chemistry78(5): 507-513 (2001).

Arnold CN. "Molecular pathogenesis of colorectal cancer", Cancer, vol. 104, pp. 2035-2047(2005).

Gillespie, K. "Type 1 diabetes:pathogenesis and prevention", CMAJ, vol. 175, pp. 165-170 (2006).

Regina A., "High-amylose wheat generated by RNA interference imrpoves indices of large-bowel health in rats", PNAS, vol. 103, pp. 3546-3551 (2006).

Sjoholm A, "Inflammation and etiology of type 2 diabetes", Diabetes/Metabolism Res. And Rev., vol. 22, pp. 4-10 (2006).

Tang et al. "Physicochemical properties and structure of large, medium and small granule starches in fractions of normal barley endosperm" *Carbohydrate Research*330:241-248 (2001).

Supplementary Search Report issued by the European Patent Office on Jul. 11, 2007 in connection with PCT International Application No. PCT/AU03/00565.

Complete file history for U.S. Patent Publication No. 2004-0060083-A1, published Mar. 25, 2004 (U.S. Appl. No. 10/434,893, filed May 9, 2003; Regina et al.).

Walker and Meritt, "Genetic Control of Abnormal Starch Granules and High Amylose Content in a Mutant of Glacier Barley," Nature 221:482-484 (1969).

Amendment and Request for Continued Examination submitted Jan. 11, 2008 in connection with U.S. Appl. No. 10/434,893, filed May 9, 2003.

Amendment submitted Apr. 19, 2007 in connection with U.S. Appl. No. 10/434, 893, filed May 9, 2003.

Amendment submitted Aug. 4, 2008 in connection with U.S. Appl. No. 10/434,893, filed May 9, 2003.

Amendment submitted Mar. 14, 2006 in connection with U.S. Appl. No. 10/434,893, filed May 9, 2003.

Complete file history for U.S. Patent No. 6,916,976 B1, issued Jul. 12, 2005.

Complete file history for U.S. Patent No. 7,521,593 B2, issued Apr. 21, 2009.

Examiner Interview Summary issued Dec. 3, 2008 in connection with U.S. Appl. No. 10/434,893, filed May 9, 2003.

Final Office Action issued Jul. 11, 2007 in connection with U.S. Appl. No. 10/434,893, filed May 9, 2003.

Notice of Allowance issued Dec. 3, 2008 in connection with U.S. Appl. No. 10/434,893, filed May 9, 2003.

Office Action issued Apr. 3, 2008 in connection with U.S. Appl. No. 10/434,893, filed May 9, 2003.

Office Action issued Oct. 19, 2006 in connection with U.S. Appl. No. 10/434,893, filed May 9, 2003.

Response submitted Nov. 17, 2003 in connection with U.S. Appl. No. 10/434,893, filed May 9, 2003.

Response to Restriction Requirement submitted Aug. 7, 2006 in connection with U.S. Appl. No. 10/434,893, filed May 9, 2003.

Restriction Requirement issued Feb. 14, 2006 in connection with U.S. Appl. No. 10/434,893, filed May 9, 2003.

Restriction Requirement issued May 5, 2006 in connection with U.S. Appl. No. 10/434,893, filed May 9, 2003.

D'Hulst et al, GenBank Accession #AAC17969 (Nov. 2001) Granule-bound starch synthase I precursor [Chlamydomonas reinhardtii].

* cited by examiner

```
   1 GGCGAGATGG CGGAAGTAAA CATGACAGGG GGGGCTGCAG AAAAACTTGA ATCTTCAGAA
  61 CCGACTCAGG GTATTGCGGA AACAATCACT GATGGTGTAA CCAAAGGAGT TAAAGAACTA
 121 GTCGTTGGGG AGAAACCGCA AGTTGTCCCA AAACCAGGAG ATGGGCAAAA AATATACGAG
 181 ATTGACCCAA CGCTGAAAGA TTTTCGGAGC CATCTTGACT ACCGATACAG CGAATACAAG
 241 AGAATTCGTG CTGCTATTGA CCAACATGAA GGTGGATTGG AAGTTTTTTC TCGTGGTTAT
 301 GAAAAGCTTG GATTTACCCG CAGTGCTAAA GGTATCACTT ACCGAGAATG GGCTCCTGGA
 361 GCGCATTCTG CAGCATTAGT AGGTGACTTC AACAATTGGA ACCCAAATGC AGATACTATG
 421 ACCAGAGATG ATTATGGTGT TTGGGAGATT TTCCTCCCTA ACAATGCTGA TGGATCCCCT
 481 GCTATTCCTC ATGGCTCACG TGTAAAGATA CGGATGGATA CTCCATCTGG TGTGAAGGAT
 541 TCAATTTCTG CTTGGATCAA GTTCTCTGTG CAGGCTCCAG GTGAAATACC ATTCAATGGC
 601 ATATATTATG ATCCACCTGA AGAGGAGAAG TATGTCTTCC AACATCCTCA ACCTAAACGA
 661 CCAGAGTCAC TAAGGATATA TGAATCACAC ATTGGAATGA GCAGCCCGGA ACCGAAGATA
 721 AATTCATATG CTAATTTTAG GGATGAGGTG CTGCCAAGAA TTAAAAGGCT TGGATACAAT
 781 GCAGTGCAGA TAATGGCAAT CCAGGAGCAT TCATACTATG CGAGCTTTGG GTACCATGTT
 841 ACTAATTTTT TTGCACCAAG TAGCCGTTTT GGAACTCCAG AGGACTTAAA ATCCTTGATC
 901 GATAGAGCAC ATGAGCTTGG TTTGCTTGTT CTTATGGATA TTGTTCATAG TCATTCGTCA
 961 AATAATACCC TTGACGGTTT GAATGGTTTC GATGGCACTG ATACACATTA CTTCCACGGT
1021 GGTCCACGTG GCCATCATTG GATGTGGGAT TCTCGTCTGT TCAACTATGG GAGTTGGGAA
1081 GTATTAAGAT TCTTACTGTC AAACGCGAGA TGGTGGCTTG AAGAATATAA GTTTGATGGA
1141 TTTCGATTTG ATGGGGTGAC TTCCATGATG TATACTCACC ATGGATTACA AATGACATTT
1201 ACTGGGAACT ATGGCGAGTA TTTTGGATTC GCCACTGATG TTGATGCGGT GGTTTACTTA
1261 ATGCTGGTCA ACGATCTAAT TCATGGACTT TATCCGGATG CTGTATCCAT TGGTGAAGAT
1321 GTCAGCGGAA TGCCTACATT TTGCATCCCT GTCCCAGATG GTGGTGTTGG TTTTGACTAT
1381 CGCCTGCATA TGGCTGTAGC AGATAAATGG ATTGAACTCC TCAAGCAAAG TGACGAATCT
1441 TGGAAAATGG CGATATTGT GCACACCCTA ACAAATAGAA GGTGGCTTGA GAAGTGTGTC
1501 ACTTATGCAG AAAGTCATGA TCAAGCACTA GTTGGTGACA AGACTATTGC ATTCTGGTTG
1561 ATGGATAAGG ATATGTATGA TTTCATGGCT CTGGATAGAC CTTCAACCCC TCGCATTGAT
1621 CGTGGCATAG CATTACATAA AATGATCAGG CTTGTCACCA TGGGTTTAGG TGGCGAAGGC
1681 TATCTTAATT TCATGGGAAA TGAGTTTGGG CATCCTGAAT GGATAGATTT TCCAAGAGGT
1741 CCGCAAACTC TTCCAACCGG CAAAGTTCTC CCTGGAAATA ACAATAGTTA TGATAAATGC
1801 CGCCGTAGAT TTGATCTTGG AGATGCAGAT TTTCTTAGAT ATCGTGGTAT GCAAGAGTTC
1861 GATCAGGCAA TGCAGCATCT TGAGGAAAAA TATGGGTTTA TGACATCTGA GCACCAGTAT
1921 GTTTCTCGGA ACATGAGGA AGATAAGGTG ATCATCTTCG AAAGAGGAGA TTTGGTATTT
1981 GTTTTCAACT TCCACTGGAG CAATAGCAAA AAAGACTACC GTGTTGGGTG TTCCAAGCCT
2041 GGGAAGTACA AGGTGGCCTT AGACTCTGAT GATGCACTCT TTGGTGGATT CAGCAGGCTT
2101 GATCATGATG TCGACTACTT CACAACCGAA CATCCGCATG ACAACAGGCC ACGCTCTTTC
2161 TCGGTGTACA CTCCGAGCAG AACTGCGGTC GTGTATGCCC TTACAGAGTA AGAACCAGCA
2221 GCTGTTTGTT ACAAGGCAAA AAGAGAACTC CAGTGAGCTC GTGGATTGTG AGCGAAGCGA
2281 CGGGCAACGG TCCGAGACTG TTCTAACCGC CGTGATTGGG AGGGGATCGT GCCTCTTCCC
2341 CAGATGCTAG GAGGATCAGA TGGATAGGTA GCTTGCTGGC GAGCCCTCGT TTTCAAGTGA
2401 CCTGCGAAAG AAAATGGACG GGCCTGGGTG ACATTTTGTA GTGCTGCACT GAACCATCCT
2461 ATCTCTCACA TTCCCGGTTG TTTATGTACA TATAAACTAA TAATTGCCCG TGCGCTTCAA
2521 CTTGGACAAA AAAAAAAAAA AAAAAAAAAA AAAA
```

FIGURE 1

```
   1 GGCGAGATGG CGGCGCCGGC GTTCGCAGTT TCCGCGGCGG GGATCGCCCG GCCATCGGCT
  61 CGTCGATCCA GCGGGGCAGA GCCGAGATCG CTGCTCTTCG GCCGCAACAA GGGCACCCGT
 121 TTCCCCCGTG CCGTCGGCGT CGGAGGTTCT GGGTGGCGCG TGGTCATGCG CGCGGGCGGC
 181 CCGTCCGGGG AGGTGATGAT CCCTGACGGC GGTAGTGGCG GAAGCGGAAC ACCGCTTCC
 241 ATCGAGGGTT CCGTTCAGTT CGAGTCTGAT GATCTGGAGG TTCCATTCAT CGACGATGAA
 301 CCAAGCCTGC ACGATGGAGG TGAAGATACT ATTCGGTCTT CAGAGACATA TCAGGTTACT
 361 GAAGAAATTG ATGCTGAAGG CGTGAGCAGA ATGGACAAAG AATCATCCAC GGTGAAGAAA
 421 ATACGCATTG TGCCACAACC CGGAAATGGA CAGCAAATAT ACGACATTGA CCCAATGCTC
 481 CGAGACTTTA AGTACCATCT TGAGTATCGA TACAGCCTAT ATAGGAGAAT ACGTTCAGAC
 541 ATTGATGAAT ACGATGGAGG CATGGATGTA TTTTCCCGCG GCTACGAGAA GTTTGGATTT
 601 GTTCGCAGCG CTGAAGGTAT CACTTACCGA GAATGGGCTC CTGGAGCAGA TTCTGCAGCA
 661 TTAGTTGGCG ACTTCAACAA TTGGGATCCA ACTGCAGACC ATATGAGCAA AAATGACTTG
 721 GGTATTTGGG AGATTTTTCT GCCAAACAAT GCAGATGGTT CGCCGCCAAT TCCTCATGGC
 781 TCACGGGTGA AGGTGCGGAT GGATACTCCA TCTGGGACAA AGGATTCAAT TCCTGCTTGG
 841 ATCAAGTACT CCGTGCAGAC TCCAGGAGAT ATACCATACA ATGGAATATA TTATGACCCT
 901 CCTGAAGAGG AGAAGTATGT ATTCAAGCAT CCTCAACCTA AACGACCAAA ATCATTGCGG
 961 ATATATGAAA CACATGTTGG CATGAGTAGC CCGGAACCAA AGATCAACAC ATATGCAAAC
1021 TTCAGAGATG AGGTGCTTCC AAGAATTAAA AGACTTGGAT ACAATGCAGT TCAAATAATG
1081 GCAATCCAAG AGCATTCATA CTATGGAAGC TTTGGGTACC ATGTTACCAA TTTCTTTGCA
1141 CCAAGTAGCC GTTTTGGGTC CCCAGAAGAT TTAAAATCCT TGATTGATAG AGCTCACGAG
1201 CTTGGTTTGC TTGTCCTGAT GGATGTTGTT CACAGTCACG CATCAAGTAA TACCTTGGAC
1261 GGTTTGAATG GTTTTGATGG CACGGATACA CATTACTTTC ATGGCGGCTC ACGGGGCCAT
1321 CACTGGATGT GGGATTCTCG TGTGTTCAAC TACGGGAATA AGGAAGTTAT AAGGTTTCTA
1381 CTTTCCAATG CAAGATGGTG GCTAGAGGAA TATAAGTTCG ATGGTTTCCG ATTCGACGGC
1441 GCGACCTCCA TGATGTATAC CCACCATGGA TTACAAGTAA CCTTTACAGG GAGCTACCAT
1501 GAATATTTTG GCTTTGCCAC GGATGTAGAT GCAGTTGTTT ACTTGATGCT GGTGAATGAT
1561 CTAATTCACG CGCTTTATCC TGAAGCCGTT ACTATTGGTG AAGATGTTAG TGGAATGCCT
1621 ACATTTGCCC TTCCTGTTCA AGTTGGTGGG GTTGGTTTTG ACTATCGCTT ACATATGGCC
1681 GTTGCCGATA AATGGATTGA ACTTCTCAAA GGAAGCGATG AAGGTTGGGA GATGGGTAAT
1741 ATTGTGCACA CACTAACAAA TAGAAGGTGG TTGGAAAAGT GTGTTACTTA TGCTGAAAGT
1801 CATGATCAAG CACTTGTTGG AGACAAGACT ATTGCATTCT GGTTGATGGA CAAGGATATG
1861 TATGATTTCA TGGCTCTGAA CGGACCTTCG ACACCTAATA TTGATCGCGG AATAGCACTG
1921 CATAAAATGA TTAGACTTAT CACAATGGCT TTAGGAGGAG AGGGTTATCT TAACTTTATG
1981 GGAAATGAGT TCGGGCATCC TGAATGGATA GACTTTCCAA GAGGCCCACA AGTACTTCCA
2041 ACTGGTAAGT TCATCCCAGG AAATAACAAC AGTTACGACA AATGCCGTCG AAGATTTGAC
2101 CTGGGTGATG CAGAATTTCT CAGGTATCAT GGTATGCAGC AATTTGATCA GGCAATGCAG
2161 CATCTTGAGG AAAAATATGG CTTTATGACA TCAGACCACC AGTACGTATC TCGGAAACAC
2221 GAGGAAGATA AGGTGATCGT GTTTGAAAAA GGGGACTTGG TATTTGTGTT CAACTTCCAC
2281 TGGAGTAATA GCTATTTCGA CTACCGGGTC GGTTGCTTAA AGCCTGGGAA GTACAAGGTG
2341 GTGTTAGACT CAGACGCTGG ACTCTTTGGT GGATTGGTA GGATCCATCA CACTGGAGAG
2401 CACTTCACTA ATGGCTGCCA ACATGACAAC AGGCCCCATT CGTTCTCAGT GTACACTCCT
2461 AGCAGAACCT GTGTTGTCTA TGCTCCAATG AACTAACAGC AAAGTGCAGC ATGCGCATGC
2521 GCGCTGTTGT TGCTTAGTAG CAACATAAAT CGTATGGTCA ATACAACCAG GTGCAAGGTT
2581 TAATAAGGTT TTTTTTTTTT TTTTTTTTT TTTTTTTTTT TTTTTTTTT TTTTGCTTCA
2641 ACCAGTCCTG GATAGACAAG ACAACATGAT GTTGTGCTGT GTGCTCCCAA TCCCCAGGGC
2701 GTTGTGAGGA AAACATGCTC ATCTGTGTTA CCATTTTATG AATCAGCAAC GATACTTCTC
2761 CCAAAAAAAA AAAAAAAAA
```

FIGURE 2

```
   1  AGAAACACCT CCATTTTAGA TTTTTTTTTT GTTCTTTTCG GACGGTGGGT
  51  CGTGGAGAGA TTAGCGTCTA GTTTTCTTAA AAGAACAGGC CATTTAGGCC
 101  CTGCTTTACA AAAGGCTCAA CCAGTCCAAA ACGTCTGCTA GGATCACCAG
 151  CTGCAAAGTT AAGCGCGAGA CCACCAAAAC AGGCGCATTC GAACTGGACA
 201  GACGCTCACG CAGGAGCCCA GCACCACAGG CTTGAGCCTG ACAGCGGACG
 251  TGAGTGCGTG ACACATGGGG TCATCTATGG GCGTCGGAGC AAGGAAGAGA
 301  GACGCACATG AACACCATGA TGATGCTATC AGGCCTGATG GAGGGAGCAA
 351  CCATGCACCT TTTCCCCTCT GGAAATTCAT AGCTCACACT TTTTTTTAAT
 401  GGAAGCAAGA GTTGGCAAAC ACATGCATTT TCAAACAAGG AAAATTAATT
 451  CTCAAACCAC CATGACATGC AATTCTCAAA CCATGCACCG ACGAGTCCAT
 501  GCGAGGTGGA AACGAAGAAC TGAAAATCAA CATCCCAGTT GTCGAGTCGA
 551  GAAGAGGATG ACACTGAAAG TATGCGTATT ACGATTTCAT TTACATACAT
 601  GTACAAATAC ATAATGTACC CTACAATTTG TTTTTTGGAG CAGAGTGGTG
 651  TGGTCTTTTT TTTTTACACG AAAATGCCAT AGCTGGCCCG CATGCGTGCA
 701  GATCGGATGA TCGGTCGGAG ACGACGGACA ATCAGACACT CACCAACTGC
 751  TTTTGTCTGG GACACAATAA ATGTTTTGT AAACAAAATA AATACTTATA
 801  AACGAGGGTA CTAGAGGCCG CTAACGGCAT GGCCAGGTAA ACGCGCTCCC
 851  AGCCGTTGGT TTGCGATCTC GTCCTCCCGC ACGCAGCGTC GCCTCCACCG
 901  TCCGTCCGTC GCTGCCACCT CTGCTGTGCG CGCGCACGAA GGGAGGAAGA
 951  ACGAACGCCG CACACACACT CACACACGGC ACACTCCCCG TGGGTCCCCT
1001  TTCCGGCTTG GCGTCTATCT CCTCTCCCCC GCCCATCCCC ATGCACTGCA
1051  CCGTACCCGC CAGCTTCCAC CCCCGCCGCA CACGTTGCTC CCCCTTCTCA
1101  TCGCTTCTCA ATTAATATCT CCATCACTCG GGTTCCGCGC TGCATTTCGG
1151  CCGGCGGGTT GAGTGAGATC TGGGCGACTG GCTGACTCAA TCACTACGCG
1201  GGGATGGCGA CGTTCGCGGT GTCCGGCGCG ACTCTCGGTG TGGCGCGGGC
1251  CGGCGTCGGA GTGGCGCGGG CCGGCTCGGA GCGGAGGGGC GGGGCGGACT
1301  TGCCGTCGCT GCTCCTCAGG AAGAAGGACT CCTCTCGTAC GCCTCGCTCT
1351  CTCGAATCTC CCCCGTCTGG CTTTGGCTCC CCTTCTCTCT CCTCTGCGCG
1401  CGCATGGCCT GTTCGATGCT GTTCCCCAAT TGATCTCCAT GAGTGAGAGA
1451  GATAGCTGGA TTAGGCGATC GCGCTTCCTG AACCTGTATT TTTTCCCCCG
1501  CGGGGAAATG CGTTAGTGTC ACCCAGGCCC TGGTGTTACC ACGGCTTTGA
1551  TCATTCCTCG TTTCATTCTG ATATATATTT TCTCATTCTT TTTCTTCCTG
1601  TTCTTGCTGT AACTGCAAGT TGTGGCGTTT TTTCACTATT GTAGTCATCC
1651  TTGCATTTTG CAGGCGCCGT CCTGAGCCGC GCGGCCTCTC CAGGGAAGGT
1701  CCTGGTGCCT GACGGCGAGA GnGACGACTT GGCAAGTCCG GCGCAACCTG
1751  AAGAATTACA GGTACACACA CTCGTGCCGG TAAATCTTCA TACAATCGTT
1801  ATTCACTTAC CAAATGCCGG ATGAAACCAA CCACGGATGC GTCAGGTTTC
1851  GAGCTTCTTC TATCAGCATT GTGCAGTACT GCACTGCCTT GTTCATTTTG
1901  TTAGCCTTGG CCCCGTGCTG GCTCTTGGGC CACTGAAAAA ATCAGATGGA
1951  TGTGCATTCT AGCAAGAACT TCACAACATA ATGCACCGTT TGGGGTTTCG
2001  TCAGTCTGCT CTACAATTGC TATTTTTCGT GCTGTAGATA CCTGAAGATA
2051  TCGAGGAGCA AACGGCGGAA GTGAACATGA CAGGGGGGAC TGCAGAGAAA
2101  CTTCAATCTT CAGAACCGAC TCAGGGCATT GTGGAAACAA TCACTGATGG
2151  TGTAACCAAA GGAGTTAAGG AACTAGTCGT GGGGGAGAAA CCGCGAGTTG
2201  TCCCAAAACC AGGAGATGGG CAGAAAATAT ACGAGATTGA CCCAACACTG
2251  AAAGATTTTC GGAGCCATCT TGACTACCGG TAATGCCTAC CCGCTGCTTT
2301  CGCTCATTTT GAATTAAGGT CCTTTCATCA TGCAAATTTG GGAACATCA
2351  AAGAGACAAA GACTAGGGAC CACCATTTCA TACAGATCCC TTCGTGGTCT
2401  GAGAATATGC TGGGAAGTAA ATGTATAATT GATGGCTACA ATTTGCTCAA
2451  AATTGCAATA CGAATAACTG TCTCCGATCA TTACAATTAA AGAGTGGCAA
2501  ACTGATGAAA ATGTGGTGGA TGGGTTATAG ATTTTACTTT GCTAATTCCT
2551  CTACCAAATT CCTAGGGGGG AAATCTACCA GTTGGGAAAC TTAGTTTCTT
2601  ATCTTTGTGG CCTTTTTGTT TTGGGGAAAA CACATTGCTA AATTCGAATG
```

FIGURE 3

```
2651  ATTTTGGGTA TACCTCGGTG GATTCAACAG ATACAGCGAA TACAAGAGAA
2701  TTCGTGCTGC TATTGACCAA CATGAAGGTG GATTGGAAGC ATTTTCTCGT
2751  GGTTATGAAA AGCTTGGATT TACCCGCAGG TAAATTTAAA GCTTTATTAT
2801  TATGAAACGC CTCCACTAGT CTAATTGCAT ATCTTATAAG AAAATTTATA
2851  ATTCCTGTTT TCCCCTCTCT TTTTTCCAGT GCTGAAGGTA TCGTCTAATT
2901  GCATATCTTA TAAGAAAATT TATATTCCTG TTTTCCCCTA TTTTCCAGTG
2951  CTGAAGGTAT CACTTACCGA GAATGGGCTC CCTGGAGCGC ATGTTATGTT
3001  CTTTTAAGTT CCTTAACGAG ACACCTTCCA ATTTATTGTT AATGGTCACT
3051  ATTCACCAAC TAGCTTACTG GACTTACAAA TTAGCTTACT GAATACTGAC
3101  CAGTTACTAT AAATTTATGA TCTGGCTTTT GCACCCTGTT ACAGTCTGCA
3151  GCATTAGTAG GTGACTTCAA CAATTGGAAT CCAAATGCAG ATACTATGAC
3201  CAGAGTATGT CTACAGCTTG GCAATTTTCC ACCTTTGCTT CATAACTACT
3251  GATACATCTA TTTGTATTTA TTTAGCTGTT TGCACATTCC TTAAAGTTGA
3301  GCCTCAACTA CATCATATCA AAATGGTATA ATTTGTCAGT GTCTTAAGCT
3351  TCAGCCCAAA GATTCTACTG AATTTAGTCC ATCTTTTTGA GATTGAAAAT
3401  GAGTATATTA AGGATGAATG AATACGTGCA ACACTCCCAT CTGCATTATG
3451  TGTGCTTTTC CATCTACAAT GAGCATATTT CCATGCTATC AGTGAAGGTT
3501  TGCTCCTATT GATGCAGATA TTTGATATGG TCTTTTCAGG ATGATTATGG
3551  TGTTTGGGAG ATTTTCCTCC CTAACAACGC TGATGGATCC TCAGCTATTC
3601  CTCATGGCTC ACGTGTAAAG GTAAGCTGGC CAATTATTTA GTCGAGGATG
3651  TAGCATTTTC GAACTCTGCC TACTAAGGGT CCCTTTTCCT CTCTGTTTTT
3701  TAGATACGGA TGGATACTCC ATCCGGTGTG AAGGATTCAA TTTCTGCTTG
3751  GATCAAGTTC TCTGTGCAGG CTCCAGGTGA AATACCTTTC AATGGCATAT
3801  ATTATGATCC ACCTGAAGAG GTAAGTATCG ATCTACATTA CATTATTAAA
3851  TGAAATTTCC AGTGTTACAG TTTTTTAATA CCCACTTCTT ACTGACATGT
3901  GAGTCAAGAC AATACTTTTG AATTTGGAAG TGACATATGC ATTAATTCAC
3951  CTTCTAAGGG CTAAGGGGCA ACCAACCTTG GTGATGTGTG TATGCTTGTG
4001  TGTGACATAA GATCTTATAG CTCTTTTATG TGTTCTCTGT TGGTTAGGAT
4051  ATTCCATTTT GGCCTTTTGT GACCATTTAC TAAGGATATT TACATGCAAA
4101  TGCAGGAGAA GTATGTCTTC CAACATCTCA ACTAAACGAC CAGAGTCACT
4151  AAGGATTTAT GAATCACACA TTGGAATGAG CAGCCCGGTA TGTCAATAAG
4201  TTATTTCACC TGTTTCTGGT CTGATGGTTT ATTCTATGGA TTTTCTAGTT
4251  CTGTTATGTA CTGTTAACAT ATTACATGGT GCATTCACTT GACAACCTCG
4301  ATTTTATTTT CTAATGTCTT CATATTGGCA AGTGCAAAAC TTTGCTTCCT
4351  CTTTGTCTGC TTGTTCTTTT GTCTTCTGTA AGATTTCCAT TGCATTTGGA
4401  GGCAGTGGGC ATGTGAAAGT CATATCTATT TTTTTTTTGT CAGAGCATAG
4451  TTATATGAAT TCCATTGTTG TTGCAATAGC TCGGTATAAT GTAACCATGT
4501  TACTAGCTTA AGATTTCCCA CTTAGGATGT AAGAAATATT GCATTGGAGC
4551  GTCTCCAGCA AGCCATTTCC TACCTTATTA ATGAGAGAGA GACAAGGGGG
4601  GGGGGGGGGG GGGGGTTCCC TTCATTATTC TGCGAGCGAT TCAAAAACTT
4651  CCATTGTTCT GAGGTGTACG TACTGCAGGG ATCTCCCATT ATGAAGAGGA
4701  TATAGTTAAT TCTTTGTAAC CTACTTGGAA ACTTGAGTCT TGAGGCATCG
4751  CTAATATATA CTATCATCAC AATACTTAGA GGATGCATCT GAAnATTTTA
4801  GTGTGATCTT GCACAGGAAC CGAAGATAAA TTCATATGCT AATTTTAGGG
4851  ATGAGGTGTT GCCAAGAATT AAAAGGCTTG GATACAATGC AGTGCAGATA
4901  ATGGCAATCC AGGAGCATTC ATACTATGCA AGCTTTGGGT ATTCACACAA
4951  TCCATTTTTT TCTGTATACA CnTCTTCACC CATTTGGAGC TATTACATCC
5001  TAATGCTTCA TGCACATAAA ATATTTGGAT ATAATCCTTT ATTAGATATA
5051  TAGTACAACT ACACTTAGTA TTCTGAnnAA nAAGATCATT TTATTGTTGT
5101  TGGCTTGTTC CAGGTACCAT GTTACTAATT TTTTGCACC AAGTAGCCGT
5151  TTTGGAACTC CAGAGGACTT AAAATCCTTG ATCGATAGAG CACATGAGCT
5201  TGGTTTGCTT GTTCTTATGG ATATTGTTCA TAGGTAATTA GTCCAATTTA
5251  ATTTTAGCTG TTTTACTGTT TATCTGGTAT TCTAAAGGGA AATTCAGGCA
5301  ATTATGATAC ATTGTCAAAA GCTAAGAGTG GCGAAAGTGA AATGTCAAAA
```

```
5351  TCTAGAGTGG CATAAGGAAA ATTGGCAAAA ACTAGAGTGG CAAAAATAAA
5401  ATTTTCCCAT CCTAAATGGC AGGGCCCTAT CGCCGAATAT TTTTCCATTC
5451  TATATAATTG TGCTACGTGA CTTCTTTTTT CTCAGATGTA TTAAACCAGT
5501  TGGACATGAA ATGTATTTGG TACATGTAGT AAACTGACAG TTCCATAGAA
5551  TATCGTTTTG TAATGGCAAC ACAATTTGAT GCCATAGATG TGGATTGAGA
5601  AGTTCAGATG CTATCAATAG AATTAATCAA CTGGCCATGT ACTCGTGGCA
5651  CTACATATAG TTTGCAAGTT GGAAAACTGA CAGCAATACC TCACTGATAA
5701  GTGGCCAGGC CCCACTTGCC AGCTTCATAC TAGATGTTAC TTCCCTGTTG
5751  AATTCATTTG AACATATTAC TTAAAGTTCT TCATTTGTCC TAAGTCAAAC
5801  TTCTTTAAGT TTGACCAAGT CTATTGGAAA ATATATCAAC ATCTACAACA
5851  CCAAATTACT TTGATCAGAT TAACAATTTT TATTTTATTA TATTAGCACA
5901  TCTTTGATGT TGTAGATATC AGCACATTTT TCTATAGCT TGGTCAAATA
5951  TAGAGAAGTT TGACTTAGGA CAAATCTAGA ACTTCAATCA ATTTGGATCA
6001  GAGGGAACAT CAAATAATAT AGATAGATGT CAACACTTCA ACAAAAAAAT
6051  CAGACCTTGT CACCATATAT GCATCAGACC ATCTGTTTGC TTTAGCCACT
6101  TGCTTTCATA TTTATGTGTT TGTACCTAAT CTACTTTCC TTCTACTTGG
6151  TTTGGTTGAT TCTATTTCAG TTGCATTGCT TCATCAATGA TTTTGTGTAC
6201  CCTGCAGTCA TTCGTCAAAT AATACCCTTG ACGGTTTGAA TGGTTTCGAT
6251  GGCACTGATA CACATTACTT CCACGGTGGT CCACGCGGCC ATCATTGGAT
6301  GTGGGATTCT CGTCTATTCA ACTATGGGAG TTGGGAAGTA TGTAGCTCTG
6351  ACTTCTGTCA CCATATTTGG CTAACTGTTC CTGTTAATCT GTTCTTACAC
6401  ATGTTGATAT TCTATTCTTA TGCAGGTATT GAGATTCTTA CTGTCAAACG
6451  CGAGATGGTG GCTTGAAGAA TATAAGTTTG ATGGATTTCG ATTTGATGGG
6501  GTGACCTCCA TGATGTATAC TCACCATGGA TTACAAGTAA GTCATCAAGT
6551  GGTTTCAGTA ACTTTTTTAG GGCACTGAAA CAATTGCTAT GCATCATAAC
6601  ATGTATCATG ATCAGGACTT GTGCTACGGA GTCTTAGATA GTTCCCTAGT
6651  ATGCTTGTAC AATTTTACCT GATGAGATCA TGGAAGATTG GAAGTGATTA
6701  TTATTTATTT TCTTTCTAAG TTTGTTTCTT GTTCTAGATG ACATTTACTG
6751  GGAACTATGG CGAATATTTT GGATTTGCTA CTGATGTTGA TGCGGTAGTT
6801  TACTTGATGC TGGTCAACGA TCTAATTCAT GGACTTTATC CTGATGCTGT
6851  ATCCATTGGT GAAGATGTAA GTGCTTACAG TATTTATGAT TTTTAACTAG
6901  TTAAGTAGTT TTATTTTGGG GATCAGTCTG TTACACTTTT TGTTAGGGGT
6951  AAAATCTCTC TTTTCATAAC AATGCTAATT TATACCTTGT ATGATAATGC
7001  ATCACTTAnG TAATTTGAAA AGTGCAAGGG CATTCAAGCT TACGAGCATA
7051  TTTTTTGATG GCTGTAATTT ATTTGATAGT ATGCTTGTTT GGGTTTTTCA
7101  ATAAGTGGGA GTGTGTGACT AATGTTGTAT TATTTATTTA ATTGCGGAAG
7151  AAATGGGCAA CCTTGTCAAT TGCTTCAGAA GGCTAACTTT GATTCCATAA
7201  ACGCTTTGGA AATGAGAGGC TATTCCCAAG GACATGAATT ATACTTCAGT
7251  GTGTTCTGTA CATGTATTTG TAATAGTGGT TTAACTTAAA TTCCTGCACT
7301  GCTATGGAAT CTCACTGTAT GTTGTnAGTG TACACATCCA CAAACAAGTA
7351  ATCCTGAGCT TTCAACTCAT GAGAAAATAn GAnGTCCGCT TCTGCCAGCA
7401  TTAACTGTTC ACAGTTCTAA TTTGTGTAAC TGTGAAATTG TTCAGGTCAG
7451  TGGAATGCCT ACATTTTGCA TCCCTGTTCC AGATGGTGGT GTTGGTTTTG
7501  ACTACCGCCT GCATATGGCT GTAGCAGATA AATGGATTGA ACTCCTCAAG
7551  TAAGTGCAGG AATATTGGTG ATTACATGCG CACAATGATC TAGATTACAT
7601  TTTCTAAATG GTAAAAGGA AAATATGTAT GTGAATATCT AGACATTTGC
7651  CTGTTATCAG CTTGAATACG AGAAGTCAAA TACATGATTT AAATAGCAAA
7701  TCTCGGAAAT GTAATGGCTA GTGTCTTTAT GCTGGGCAGT GTACATTGCG
7751  CTGTAGCAGG CCAGTCAACA CAGTTAGCAA TATTTTCAGA AACAATATTA
7801  TTTATATCCG TATATGAnGA AAGTTAGTAT ATAAACTGTG GTCATTAATT
7851  GTGTTCACCT TTTGTCCTGT TTAAGGATGG GCAGTAGGTA ATAAATTTAG
7901  CCAGATAAAA TAAATCGTTA TTAGGTTTAC AAAAGGAATA TACAGGGTCA
7951  TGTAGCATAT CTAGTTGTAA TTAATGAAAA GGCTGACAAA AGGCTCGGTA
8001  AAAAAAACTT TATGATGATC CAGATAGATA TGCAGGAACG CGACTAAAGC
```

FIGURE 3
-continued-

```
 8051  TCAAATACTT ATTGCTACTA CACAGCTGCC AATCTGTCAT GATCTGTGTT
 8101  CTGCTTTGTG CTATTTAGAT TTAAATACTA ACTCGATACA TTGGCAATAA
 8151  TAAACTTAAC TATTCAACCA ATTTGGTGGA TACCAGAnAT TTCTGCCCTC
 8201  TTGTTAGTAA TGATGTGCTC CCTGCTGCTG TTCTCTGCCG TTACAAAAGC
 8251  TGTTTTCAGT TTTTTGCATC ATTATTTTTG TGTGTGAGTA GTTAAGCAT
 8301  GTTTTTTGAA GCTGTGAGCT GTTGGTACTT AATACATTCT TGGAAGTGTC
 8351  CAAATATGCT GCAGTGTAAT TTAGCATTTC TTTAACACAG GCAAAGTGAC
 8401  GAATCTTGGA AAATGGGCGA TATTGTGCAC ACCCTAACAA ATAGAAGGTG
 8451  GCTTGAGAAG TGTGTAACTT ATGCAGAAAG TCATGATCAA GCACTAGTTG
 8501  GTGACAAGAC TATTGCATTC TGGTTGATGG ATAAGGTACT AGCTGTTACT
 8551  TTTGGACAAA AGAATTACTC CCTCCCGTTC CTAAATATAA GTCTTTGTAG
 8601  AGATTCCACT ATGGACCACA TAGTATATAG ATGCATTTTA GAGTGTAGAT
 8651  TCACTCATTT TGCTTCGTAT GTAGTCCATA GTGAAATCTC TACAGAGACT
 8701  TATATTTAGG AACGGAGGGA GTACATAATT GATTTGTCTC ATCAGATTGC
 8751  TAGTGTTTTC TTGTGATAAA GATTGGCTGC CTCACCCATC ACCAGCTATT
 8801  TCCCAACTGT TACTTGAGCA GAATTTGCTG AAAACGTACC ATGTGGTACT
 8851  GTGGCGGCTT GTGAACTTTG ACAGTTATGT TGCAATTTTC TGTTCTTATT
 8901  TATTTGATTG CTTATGTTAC CGTTCATTTG CTCATTCCTT TCCGAGACCA
 8951  GCCAAAGTCA CGTGTTAGCT GTGTGATCTG TTATCTGAAT CTTGAGCAAA
 9001  TTTTATTAAT AGGCTAAAAT CCAACGAATT ATTTGCTTGA ATTTAAATAT
 9051  ACAGACGTAT AGTCACCTGG CTCTTTCTTA GATGATTACC ATAGTGCCTG
 9101  AAGGCTGAAA TAGTTTTGGT GTTTCTTGGA TGCCGCCTAA AGGAGTGATT
 9151  TTTATTGGAT AGATTCCTGG CCGAGTCTTC GTTACAACAT AACATTTTGG
 9201  AGATATGCTT AGTAACAGCT CTGGGAAGTT TGGTCACAAG TCTGCATCTA
 9251  CACGCTCCTT GAGGTTTTAT TATGGCGCCA TCTTTGTAAC TAGTGGCACC
 9301  TGTAAGGAAA CACATTCAAA AGGAAACGGT CACATCATTC TAATCAGGAC
 9351  CACCATACTA AGAGCAAGAT TCTGTTCCAA TTTTATGAGT TTTTGGGACT
 9401  CCAAAGGGAA CAAAAGTGTC TCATATTGTG CTTATAACTA CAGTTGTTTT
 9451  TATACCAGTG TAGTTTTATT CCAGGACAGT TGATACTTGG TACTGTGCTG
 9501  TAAATTATTT ATCCGACATA GAACAGCATG AACATATCAA GCTCTCTTTG
 9551  TGCAGGATAT GTATGATTTC ATGGCTCTGG ATAGGCTTCA ACTCTTCGCA
 9601  TTGATCGTGG CATAGCATTA CATAAAATGA TCAGGCTTGT CACCATGGGT
 9651  TTAGGTGGTG AAGGCTATCT TAACTTCATG GGAAATGAGT TTGGGCATCC
 9701  TGGTCAGTCT TTACAACATT ATTGCATTCT GCATGATTGT GATTTACTGT
 9751  AATTTGAACC ATGCTTTTCT TTCACATTGT ATGTATTATG TAATCTGTTG
 9801  CTTCCAAGGA GGAAGTTAAC TTCTATTTAC TTGGCAGAAT GGATAGATTT
 9851  TCCAAGAGGC CCACAAACTC TTCCAACCGG CAAAGTTCTc CCCTGGAAAT
 9901  AACAATAGTT ATGATAAATG CCGCCGTAGA TTTGATCTTG TAAGTTTTAG
 9951  CTGTGCTATT ACATTCCCTC ACTAGATCTT TATTGGCCAT TTATTTCTTG
10001  ATGAAATCAT AATGTTTGTT AGGAAAGATC AACATTGCTT TTGTAGTTTT
10051  GTAGACGTTA ACATAAGTAT GTGTTGAGAG TTGTTGATCA TTAAAAATAT
10101  CATGATTTTT TGCAGGGAGA TGCAGATTTT CTTAGATATC GTGGTATGCA
10151  AGAGTTCGAT CAGGCAATGC AGCATCTTGA GGAAAAATAT GGGGTATGTC
10201  ACTGGTTTGT CTTTGTTGCA TAACAAGTCA CAGTTTAACG TCAGTCTCTT
10251  CAAGTGGTAA AAAAGTGTA GAATTAATTC CTGTAATGAG ATGAAAACTG
10301  TGCAAAGGCG GAGCTGGAAT TGCTTTTCAC CAAAACTATT TTCTTAAGTG
10351  CTTGTGTATT GATACATATA CCAGCACTGA CAATGTAACT GCAGTTTATG
10401  ACATCTGAGC ACCAGTATGT TTCACGGAAA CATGAGGAAG ATAAGGTGAT
10451  CATCCTCnAA AAGAGGAGAT TTGGTATTTG TTTTCAACTT CCACTGGAGC
10501  AATAGCTTTT TTGACTACCG TGTTGGGTGT TCCAAGCCTG GGAAGTACAA
10551  GGTATGCTTG CCTTTTCATT GTCCACCCTT CACCAGTAGG GTTAGTGGGG
10601  GCTTCTACAA CTTTTAATTC CACATGGATA GAGTTTGTTG GTCGTGCAGC
10651  TATCAATATA AGAATAGGG TAATTTGTAA AGAAAGAAT TTGCTCGAGC
10701  TGTTGTAGCC ATAGGAAGGT TGTTCTTAAC AGCCCCGAAG CACATACCAT
```

```
10751   TCATTCATAT tATCTACTTA AGTGTTTGTT TCAATCTTTA TGCTCAGTTG
10801   GACTCGGTCT AATACTAGAA CTATTTTCCG AATCTACCCT AACCATCCTA
10851   GCAGTTTTAG AGCAGCCCCA TTTGGACAAT TGGCTGGGTT TTTGTTAGTT
10901   GTGACAGTTT CTGCTATTTC TTAATCAGGT GGCCTTGGAC TCTGACGATG
10951   CACTCTTTGG TGGATTCAGC AGGCTTGATC ATGATGTCGA CTACTTCACA
11001   ACCGTAAGTC TGGGCTCAAG CGTCACTTGA CTCGTCTTGA CTCAACTGCT
11051   TACAAATCTG AATCAACTTC CCAATTGCTG ATGCCCTTGC AGGAACATCC
11101   GCATGACAAC AGGCCGCGCT CTTTCTCGGT GTACACTCCG AGCAGAACTG
11151   CGGTCGTGTA TGCCCTTACA GAGTAAGAAC CAGCAGCGGC TTGTTACAAG
11201   GCAAAGAGAG AACTCCAGAG AGCTCGTGGA TCGTGAGCGA AGCGACGGGC
11251   AACGGCGCGA GGCTGCTCCA AGCGCCATGA CTGGGAGGGG ATCGTGCCTC
11301   TTCCCCAGAT GCCAGGAGGA GCAGATGGAT AGGTAGCTTG TTGGTGAGCG
11351   CTCGAAAGAA AATGGACGGG CCTGGGTGTT TGTTGTGCTG CACTGAACCC
11401   TCCTCCTATC TTGCACATTC CCGGTTGTTT TTGTACATAT AACTAATAAT
11451   TGCCCGTGCG CTCAACGTGA AAATC
```

FIGURE 3
-continued-

```
   1  AAGCTTTGTA GCCTTGCACG GGCTCCCCAA CAAACTGCCT CACTCGATTG
  51  TCAAAAAAGT AAAAATGATT GTAGAAAAAA AAACTGACTC ACTCGTCACT
 101  ACCCTACCGT CCTACATGAC ACCTGGCCGC AAGACGACGC CGTCCTCCTG
 151  CCGCGCGCGT CCGCGATCAC ACCACCGCAA AAACCAAAAC CTCTTCGCCG
 201  GTGCGTCCCA CGCTACCATC CATGCAGCCG TCCGCCCGCG CGCGCGTTGC
 251  CCGCACCACC CGCTGGCGGC CACCACGCCG CCACTCTCGC GTGAAGGCTC
 301  CGTCCGCTTC CTCCTAGTTC CACTCTCTCT CCGTGCTAGC AGTATATAGC
 351  ATCCGCCCTC CGCCCCCTCC CAATCTTAGA ACACCCCTCC CTTTGCCTCC
 401  TCATTTCGCT CGCGTGGGTT TAAGCAGGAG ACGAGGCGGG GTCAGTTGGG
 451  CAGTTAGGTT GGATCCGATC CGGCTGCGGC GGCGGCGACG GGATGGCTGC
 501  GCCGGCATTC GCAGTTTCCG CGGCGGGGCT GGCCCGGCCG TCGGCTCCTC
 551  GATCCGGCGG GGCAGAGCGG AGGGGCGCG GGTGGAGCT GCAGTCGCCA
 601  TCGCTGCTCT TCGGCCGCAA CAAGGGCACC CGTTCACCCC GTAATTATTT
 651  GCGCCACCTT TCTCACTCAC ATTCTCTCGT GTATTCTGTC GTGCTCGCCC
 701  TTCGCCGACG ACGCGTGCCG ATTCCGTATC GGGCTGCGGT GTTCAGCGAT
 751  CTTACGTCGG TTCCCTCCTG GTGTGGTGAT GTCTGTAGGT GCCGTCGGCG
 801  TCGGAGGTTC TGGATGGCGC GTGGTCATGC GCGCGGGGG GCCGTCCGGG
 851  GAGGTGATGA TCCCTGACGG CGGTAGTGGC GGAACACCGC CTTCCATCGA
 901  CGGTCCCGTT CAGTTCGATT CTGATGATCT GAAGGTAGTT TTTTTTTGC
 951  ATCGATCTGA AGGTACTTGA CATATACTAC TGTATTACCC TGAGTAAATA
1001  CTGCCACCAT ATTTTTATGG TTCGCTTGAA ATACCTGTTT ACTTGCTACG
1051  GTTTTCACTT TCATTGAGAC GTCGGACGAA ATTCACTGAA TTCCTATAAT
1101  TTGGTAGACA CCGAAATATA TACTACTCCT TCCGTCCCAT AATATAAGAG
1151  CGTTTTGGC ACCTTATATT ATAGGGCGGA GGGAGTACCT TTTAGGTCAA
1201  AATATTGTGG TAGTTTCAAT TGTATACAAG AATTCAAATA TTTTTTTTAA
1251  AAAAAAATCA ACTAATTGGT TGAGTTTCAA GTGAAGCGTT TTGGTCCTTT
1301  GGCTGAGATG TAAACCGAAA TCACTGAAAT TCATAGTAGC CGAAACTTTA
1351  ATAGAACTGA AACTCAAAAT CTGCTATCCG GCGAAATTCT AAAGATTTGC
1401  TTATTTCACA CGTAGGTTGC AGTACACCCT CTTTCTAATT TATTGGGGAA
1451  GGGGTATTAT TATCTTGTTA GTACCTGCCT GCATGACAAT TGAAATCTAA
1501  GACAAAACAC CATATGCGAG CCTACACAC GGTAGGTTGG TTTACAACTA
1551  TGTGTGCCAC AGTCGTCTG AACTTTTGT CCTTCACATC GTGTTAGGTT
1601  CCATTCATTG ATGATGAAAC AAGCCTACAG GATGGAGGTG AAGATAGTAT
1651  TTGGTCTTCA GAGACAAATC AGGTTAGTGA AGAAATTGAT GCTGAAGACA
1701  CGAGCAGAAT GGACAAAGAA TCATCTACGA GGGAGAAATT ACGCATTCTG
1751  CCACCACCGG GAAATGGACA GCAAATATAC GAGATTGACC CAACGCTCCG
1801  AGACTTTAAG TACCATCTTG AGTATCGGTA TGCTTCGCTT CTATTGTGTG
1851  CACTTTAAAA ACAATTTACA GTCTTTGATA AGATGTGAAT GGCTGCTTGC
1901  TGTGACACGA AACTCTTGAA GTTCGTAGTC ACTCTTGTGT GTTCATGGTT
1951  CTGAGGTAAC ATGGTAACCG AACAAAAATA GGAAAGTGGC AAGCACTGCA
2001  ATGTGAGCTA CTGATAACCA CCCATTGTAA TTGGGTACAC TGATTAATAT
2051  ATATGTCTTC ATGGGCTCTA TTTTTTTTCA ATATCTATGC CAATTGAACA
2101  ACAATGCTTT GTGGACGGGT GTTCTTTTAC CCTCTTCTTC TATCAATAGA
2151  TGATATGCAT ACTCATGCGT ATCCTACAAA AAATTGAACA ACAATGCCAC
2201  TTTCCCCCGT GTTGCTTTTG TAAGGATGAA ACACATATGT CCAGATCAAA
2251  CTATACTAGC AGTCTAACTG TGCCTTAATG GATCAAAAAC AGATATAGCC
2301  TATACAGGAG AATACGTTCA GACATTGATG AACACGAAGG AGGCATGGAT
2351  GTATTTTCCC GCGGTTACGA GAAGTTTGGA TTTATGCGCA GGTGAAATTT
2401  CTTGACTAAA TAACTATGTA TCTACCTTTT CTTTGTACTC TATCAACATT
2451  CCTCTTCCCA TGCAGCGCTG AAGGTATCAC TTACCGAGAA TGGGCTCCTG
2501  GAGCAGATGT ACGTTCTTCT AACCATCTGA TCGTTTACCT GACTATACTA
2551  ATTCTATCTT TCAACTAATT GTGAATAATT ACTGCTCATC AGCTATCCTA
2601  AGGTTGGGGA TTTTGCACCT CCCAGATGAA CAGCATATTA AGTCGCACAA
2651  CTAGCATTAT TAAGAACTAA CTCCTGCTTC CAATTGCAGT CTGCAGCATT
2701  AGTTGGCGAC TTCAACAATT GGGATCCAAA TGCAGACCAT ATGAGCAAAG
2751  TATGCATGTA GTTTCACAAA TATATCATAT TTTCTTTGTA GATTTTTTTT
```

FIGURE 4

```
2801  TTTAGATCGG  CTTATCTATT  TAAATGTGGT  TGAATATACA  CCTTATATGT
2851  ACGTTGAGCT  GTAAATATAG  TTGGAAGTGT  TTAGGAGTAT  TAAATTCACT
2901  GGACTCTATT  CTTTCACTTG  CCTGTTGCAC  GAGCCCATTA  CTAGATATCA
2951  ATGTTGATGA  TGCTTTTGTT  GTATGAGGTC  GAAGTGAAAC  ATGCATGTTA
3001  CCCTTTTATA  TAAGTAAGGT  TGCACATGTA  TTTTTTATGA  TCTAAACATT
3051  ATTTACTGAT  TTTGTTCTTG  CAAGACACTA  AGCAGTTTTA  CATAATAATG
3101  GCGTTGGAGC  AGGCCGACTG  CACATCTGAA  CTGTAGCTCC  ATGTGGTTGA
3151  TATAGATTAC  AAATGCTCAT  ATTCAATGTA  ACTGTTTTCA  GAATGACCTT
3201  GGTGTTTGGG  AGATTTTTCT  GCCAAACAAT  GCAGATGGTT  CGCCACCAAT
3251  TCCTCACGGC  TCACGGGTGA  AGGTTGTTTT  CTTCTCCTTG  CCAACGGTGT
3301  TAGGCTCAGG  AACATGTCCT  GTATTACTCA  GAAGCTCTTT  TGAACATCTA
3351  GGTGAGAATG  GATACTCCAT  CTGGGATAAA  GGATTCAATT  CCTGCTTGGA
3401  TCAAGTACTC  CGTGCAGACT  CCAGGAGATA  TACCATACAA  TGGAATATAT
3451  TATGATCCTC  CCGAAGAGGT  ATTTTACTTC  ATCTTCTGTG  CTTTTAGATT
3501  TCAGATATTT  TTATTAGAAG  AAAATTATGA  TTTTTTCCCT  CACGAACCTT
3551  CCCAATTGCT  ATTTCAAGCT  GTCCTACTTA  TTTGCTGCTG  GCATCTTATT
3601  TTTCTATTCT  CTAACCAGTT  ATGAAATTCC  TTACATGCAT  ATGCAGGAGA
3651  AGTATGTATT  CAAGCATCCT  CAACCTAAAC  GACCAAAATC  ATTGCGGATA
3701  TATGAAACAC  ATGTTGGCAT  GAGTAGCCCG  GTATTTCATC  TTTACCATGT
3751  ATTCCATAAA  TGAAGTTAGC  TATATGCAGT  TCAAATTTAT  TTACAGGTTG
3801  TTACAATGGT  ATTTTGTGT  TGGTGCCCTT  CTTTCGTTTT  ATAAGTAAAA
3851  AACTTATCAT  AAATTTATTT  GTTATGCCGC  TTGGTTAATA  CAATCTGAAA
3901  AATGTAACTG  TGGACAATCT  AGAACTAGAT  AATACAAATC  TGAAAAAACA
3951  TGCTGGAATA  GTGTCATTTC  AGTCAACTAG  GATGTTTTGA  ATGCTCAAGA
4001  GAAGTACTAG  TGTGTAGCAT  CAAAAGCTGG  TGTCCATTTG  TTCAAATGTT
4051  TAATTAACAC  TATAGTGAAA  ACAAGTAATT  GCACAAAGAA  ACAAGTAATT
4101  GCCCAAGTTC  ATATGTTTTT  TCACTATATT  ACATGTTTCA  TCAACAATTT
4151  AATTAACCTC  ATTCCTTACA  AACATTGTA  TTTACATTTG  TTCCTACATA
4201  TATAGTTATT  TTATATATCA  ACTTTATAAA  TCATGACTGT  TATAATTAAA
4251  ACCGATGGTA  TATCAACGAT  TGAGATAATT  TGGCATATGT  GGATGAATTT
4301  TGTGGCTTGT  TATGCTCTTG  TTTTAATAAC  ATAATAAATA  GATTATGCTT
4351  GTTGGTAGCC  TTTTTACATT  AACACATGGG  CAATTACTTG  TTTCTTTGTG
4401  CAACCAGGAA  CCAAAGATCG  ACACATATGC  AAACTTCAGG  GATGAGGTGC
4451  TTCCAAGAAT  TAAAAGACTT  GGATACAATG  CAGTGCAAAT  AATGGCAATC
4501  CAAGAGCACT  CATACTATGG  AAGCTTTGGG  TAGTTCTCTG  GGTCGATTTC
4551  TGGTTCTTTT  AGTTATCTTT  TGTCCATAGA  ACATATTTCA  ACTTTAGCAA
4601  CTATACTATT  ATATTAACTT  TTCAGCTATT  GTCTTNCTTT  TTCTTATGTG
4651  AGAGACTGCT  GCNTCTTGCT  ACTTCCTGTG  TTCTCATTCA  GAGTANACAT
4701  CTTATGANTA  GACAACTCTA  TGTNGACATT  CCGGAAGTAT  NCACTGGCTG
4751  ATTCGGTCTA  AAATAACATA  CTGCTCAGAT  AGCCACATAA  CAGTACGATT
4801  ACACACATAA  TGACCATGTT  TGCATAGAGT  GGCGGTAGTA  TGTTCCTCAC
4851  CATACTAGCA  TAATGACTTG  TTATATAAGA  GTATATCATA  TTAACTTCTT
4901  TTCCAATGAC  ATGGAAGCTG  TAACAACTTT  CAAATCATTT  TTGTCTTTTA
4951  AGTGCTGCTT  TTTTCCTGTT  TGACAATTAA  TACAATACCA  CTTTTATGTG
5001  TTTTTACTTC  TATTGCAGGT  ACCATGTTAC  CAATTTCTTT  GCACCAAGTA
5051  GCCGTTTTGG  GTCCCCAGAA  GATTTAAAAT  CTTTGATTGA  TAGAGCTCAC
5101  GAGCTTGGCT  TGGTTGTCCT  CATGGATGTT  GTTCACAGGT  ACTTAATGTA
5151  ATTTGAGGTT  GGCGTGTTAA  GTTCACATTA  ATCTTAATTC  TTTATTTCAA
5201  TTCCTATGGC  CTCTCTCCTA  GATTGGAACA  GTAAAAGCAT  CATCCAGTTT
5251  GTATAAATTG  CTAAAGAAC  ATTTTACATG  TTAAGTATTT  TCAATTACTA
5301  TGAAACATAT  AAATTTACAT  ACTTATTGAT  TTTACGACAG  AAGTACCGAT
5351  CTCACAAGAT  GAACAATTGG  TTGATCACAT  ATCATTTCAT  ACTACAATAC
5401  AAGAAAATGA  ATAGAGAACG  AGTTAATATT  AGCCTTGGTA  AAATCAGCAA
5451  CTTGTTTGGA  AATAAAGTAT  AGTGATGCCA  GTGCAAANAA  CAAGGCATCA
5501  AGTTGGTTTC  AGCTCCCACG  GTCGGTGCTA  GCTGTCAAGG  GTAATTTGCA
5551  CGTAGTCGCA  CATAGATTTG  TGTGGGAGTG  GAAAGTAACC  ACAGATTGTC
```

```
5601  CGAGGAACAC  GGGACACACG  TCTTAGCCAC  AGGTTTGGGC  TCCCCTTGAT
5651  GCGGGTAGTA  GCTTTACTCC  TTATATGAAA  TTATCTCAAG  ATAGATTTCA
5701  ATTTGGGGTT  ACACTTANGA  ACTCANCAAG  TTAAGGATCA  ACTCNCTGAG
5751  TTCTATACGA  CTGATCTTTG  ACCGAGATAT  CTTGATCAGG  CTAAGTANCA
5801  AAATCCAGGC  CTTGAGATGT  TGAACATGTC  CTTCATTTTG  GGCTGGGTGC
5851  CCTTGGGCAT  AAGGTGTNGT  CCTTCCTTCA  TGTGCTTCTT  GCAGCGTATG
5901  ACATAAACNT  CCTCTGAGTT  GGTANATGCA  CGGTTCCCTT  TGAGGAAATC
5951  AGGGGTAGTC  GCATCTNGGG  AAAGTTGGTC  ACCCANGCAT  GGATCCTCNG
6001  CGCACACCGG  GCAAACACGG  TGAAACCACT  TCTCCTCGAC  ACTAGCTAAC
6051  TTGACATTCA  AGCAAACTAA  GAATATAACT  TTATNTCTAA  ATGAACCGGA
6101  CACCCTCCTT  GTGCCTGCAC  CTACAGAGTA  CAATGCCAGT  TTTGGACTGA
6151  ACTCTTGTGT  TCATGTATGT  GCTAATNACA  TAGGTTCTAA  CCATGATTCT
6201  AAATAGCGCG  TTATAACTCC  ACTATAGTAA  TGCTATAGCG  TTTANAAGAT
6251  CCCGCACTAA  GGGACCTTAG  TCCAAATACA  TGATCAAACA  TTTTACATAG
6301  CGCGCTATAG  CTATTTAAAA  CTATGGTCAC  CCGCTAAGAG  GCATAACTCG
6351  CTATTTAAAA  CTATGGTTCT  AACTTTTAAT  CTATTTTATG  TCTTGGTCCA
6401  AAGCCCCTTT  TTGTTCTATA  GCTTACCTT   TGGGTTGAGA  TCACCCTTAA
6451  CCCATTGGTA  ATCCTGGTTG  ATTTACTCCA  TCCTTTCTTG  CGTAGCTTTA
6501  CTTTTGGTTT  TTTGTTTCTC  ACAGTCACGC  GTCAAATAAT  ACCTTGGACG
```

A
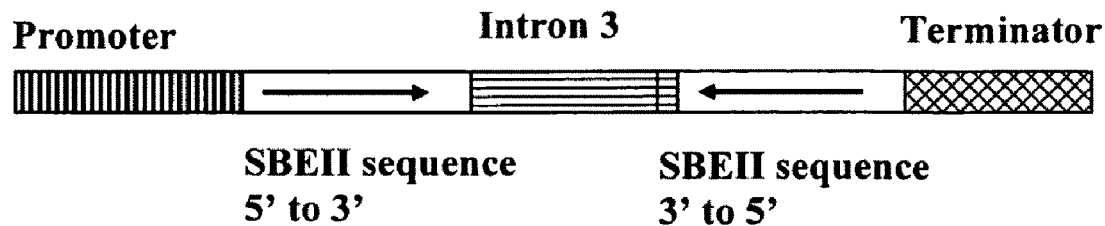
B
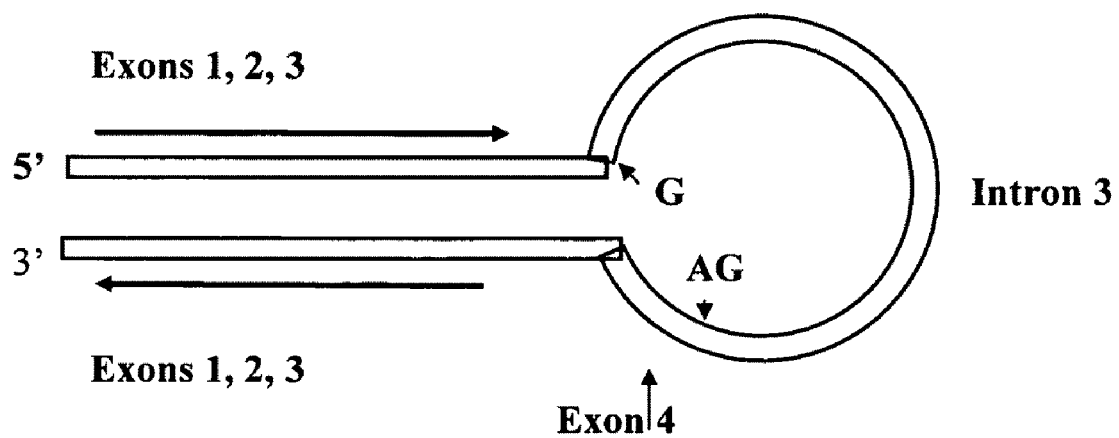
FIGURE 5

BARLEY WITH ALTERED BRANCHING ENZYME ACTIVITY AND STARCH AND STARCH CONTAINING PRODUCTS WITH AN INCREASED AMYLOSE CONTENT

This application is a divisional of U.S. Ser. No. 10/434,893, filed May 9, 2003, now U.S. Pat. No. 7,521,593, issued Apr. 21, 2009, which claims priority of Australian Application No. PS2198, filed May 9, 2002, the disclosures of each of which are hereby incorporated herein by reference into this application.

FIELD OF THE INVENTION

This invention relates to a barley plant with a reduced starch branching enzyme IIa (SBEIIa) activity in the endosperm, leading to a kernel starch with an increase in relative amylose content. The invention also relates to grain and starch and food and non-food products obtained therefrom.

BACKGROUND OF THE INVENTION

In cereals, starch makes up approximately 45-65% of the weight of the mature grain. The starch is composed of two types of molecule, amylose and amylopectin. Amylose is an essentially linear molecule composed of α-1,4 linked glucosidic chains, while amylopectin is highly branched with α-1,6 glucosidic bonds linking linear chains.

The synthesis of starch in the endosperm of higher plants is carried out by a suite of enzymes that catalyse four key steps. Firstly, ADP-glucose pyrophosphorylase activates the monomer precursor of starch through the synthesis of ADP-glucose from G-1-P and ATP. Secondly, the activated glucosyl donor, ADP-glucose, is transferred to the non-reducing end of a pre-existing α1-4 linkage by starch synthases. Thirdly, starch branching enzymes introduce branch points through the cleavage of a region of α-1,4 linked glucan followed by transfer of the cleaved chain to an acceptor chain, forming a new α-1,6 linkage. Starch branching enzymes are the only enzymes that can introduce the α-1,6 linkages into α-polyglucans and therefore play an essential role in the formation of amylopectin. Finally, starch debranching enzymes remove some of the branch linkages although the mechanism through which they act is unresolved (Myers et al., 2000).

While it is clear that at least these four activities are required for normal starch granule synthesis in higher plants, multiple isoforms of each of the four activities are found in the endosperm of higher plants and specific roles have been proposed for individual isoforms on the basis of mutational analysis (Wang et al, 1998, Buleon et al., 1998) or through the modification of gene expression levels using transgenic approaches (Abel et al., 1996, Jobling et al., 1999, Scwall et al., 2000). However, the precise contributions of each isoform of each activity to starch biosynthesis are still not known, and it is not known whether these contributions differ markedly between species. In the cereal endosperm, two isoforms of ADP-glucose pyrophosphorylase are present, one form within the amyloplast, and one form in the cytoplasm (Denyer et al., 1996, Thorbjornsen et al., 1996). Each form is composed of two subunit types. The shrunken (sh2) and brittle (bt2) mutants in maize represent lesions in large and small subunits respectively (Girouz and Hannah, 1994). Four classes of starch synthase are found in the cereal endosperm, an isoform exclusively localised within the starch granule, granule-bound starch synthase (GBSS), two forms that are partitioned between the granule and the soluble fraction (SSI, Li et al., 1999a, SSII, Li et al., 1999b) and a fourth form that is entirely located in the soluble fraction, SSIII (Cao et al, 2000, Li et al., 1999b, Li et al, 2000). GBSS has been shown to be essential for amylose synthesis (Shure et al., 1983), and mutations in SSII and SSIII have been shown to alter amylopectin structure (Gao et al, 1998, Craig et al., 1998). No mutations defining a role for SSI activity have been described.

Three forms of branching enzyme are expressed in the cereal endosperm, branching enzyme I (SBEI), branching enzyme IIa (SBEIIa) and branching enzyme IIb (SBEIIb) (Hedman and Boyer, 1982, Boyer and Preiss, 1978, Mizuno et al., 1992, Sun et al., 1997). In maize and rice, high amylose phenotypes have been shown to result from lesions in the SBEIIb gene, also known as the amylose extender (ae) gene (Boyer and Preiss, 1981, Mizuno et al., 1993; Nishi et al., 2001). In these SBEIIb mutants, endosperm starch grains showed an abnormal morphology, amylose content was significantly elevated, the branch frequency of the residual amylopectin was reduced and the proportion of short chains (<DP17, especially DP8-12) was lower. Moreover, the gelatinisation temperature of the starch was increased. In addition, there was a significant pool of material that was defined as "intermediate" between amylose and amylopectin (Boyer et al., 1980, Takeda, et al., 1993b). In contrast, maize plants mutant in the SBEIIa gene due a mutator (Mu) insertional element and consequently lacking in SBEIIa protein expression were indistinguishable from wild-type plants in the branching of endosperm starch (Blauth et al., 2001), although they were altered in leaf starch. Similarly, rice plants deficient in SBEIIa activity exhibited no significant change in the amylopectin-chain profile in endosperm (Nakamura. 2002).

In maize, the dull1 mutation causes decreased starch content and increased amylose levels in endosperm, with the extent of the change depended on the genetic background, and increased degree of branching in the remaining amylopectin (Shannon and Garwood, 1984). The gene corresponding to the mutation was identified and isolated by a transposon-tagging strategy using the transposon mutator (Mu) and shown to encode the enzyme designated starch synthase II (SSII) (Gao et al., 1998). The enzyme is now recognized as a member of the SSIII family in cereals. Mutant endosperm had reduced levels of SBEIIa activity associated with the dull1 mutation. No corresponding mutation has been reported in other cereals. It is not known if these findings are relevant to other cereals, for example barley.

WO94/09144 suggests the use of sense and antisense genes to alter the natural ratios of starch synthase (SS) and SBE in maize. However, no data are presented to substantiate the proposed molecular strategies and there is no suggestion of specifically reducing the activity of SBEIIa.

In potato, down regulation of SBEI alone causes minimal affects on starch structure (Filpse et al., 1996), although further work identified some qualitative changes (Safford et al., 1998). However, in potato the down regulation of SBEII and SBEI in combination increased the relative amylose content much more than the down-regulation of SBEII alone (Schwall et al., 2000).

Two types of debranching enzymes are present in higher plants and are defined on the basis of their substrate specificities, isoamylase type debranching enzymes, and pullulanase type debranching enzymes (Myers et al., 2000). Sugary-1 mutations in maize and rice are associated with deficiency of both debranching enzymes (James et al., 1995, Kubo et al., 1999) however the causal mutation maps to the same location as the isoamylase-type debranching enzyme gene. In the Chlamydomonas sta-7 mutant (Mouille et al., 1996), the analog of the maize sugary-1 mutation, isoamylase activity alone is down regulated. Starch biosynthesis genes that have been cloned from cereals are listed in Table 1.

Starch is widely used in the food, paper and chemical industries. The physical structure of starch can have an important impact on the nutritional and handling properties of starch for food or non-food or industrial products. Certain characteristics can be taken as an indication of starch structure including the distribution of amylopectin chain length, the degree of crystallinity and the presence of forms of crystallinity such as the V-complex form of starch crystallinity. Amylopectin chain length may be an indicator of altered crystallinity and altered gelatinisation and is also thought to have a correlation with reduced retrogradation of amylopectin. Additionally, varied amylopectin chain length distribution is thought to reflect organoleptic properties of food in which the starch is included in significant amounts. Reduced crystallinity of a starch may also be indicative of a reduced gelatinisation temperature of starch and is thought to be associated with enhanced organoleptic properties.

The relatively high gelatinisation temperature of most high amylose starches is a disadvantage for certain food applications. Gelatinisation temperature is reflective of the comminution energy required to process such foods. Higher temperatures are normally required to process grain or flour to manufacture foods from such grains or starches. Therefore, products having high amylose starches are generally more expensive. In addition, consumers may need to use longer times and higher temperatures to prepare the manufactured foods or to make foods from flour having high amylose starches. High amylose starches having reduced or normal gelatinisation temperatures would be advantageous in many food applications.

Starch composition, in particular the form called resistant starch, has important implications for bowel health, in particular health of the large bowel. Accordingly, high amylose starches have been developed in certain grains such as maize for use in foods as a means of promoting bowel health. The beneficial effects of resistant starch result from the provision of a nutrient to the large bowel wherein the intestinal microflora are given an energy source which is fermented to form inter alia short chain fatty acids. These short chain fatty acids provide nutrients for the colonocytes, enhance the uptake of certain nutrients across the large bowel and promote physiological activity of the colon. Generally if resistant starches or other dietary fibre is not provided the colon is metabolically relatively inactive.

Another nutritional component of the grains and in particular of barley is β-glucan. β-glucan consists of glucose units bonded by β (1-4) and/or β (1-3) glycosidic linkages and are not degraded by human digestive enzymes, making them suitable as a source of dietary fibre. β-glucans can be partially digested by endogenous colonic bacteria which fermentation process gives rise to short chain fatty acids (predominantly acetate, propionate and butyrate) which are beneficial to mucosal cells lining the intestine and colon (Sakata and Engelhard, 1983). Ingestion of β-glucan also has the effect of increasing bile acid excretion leading to a reduction in total serum cholesterol and low density lipoproteins (LDL) with a lowering of the risk of coronary disease. Similarly β-glucan acts by attenuating excursions in postprandial blood glucose concentration. It is thought that these effects may also be based on the increase of viscosity in the contents of the stomach and intestines.

Whilst modified starches or β glucans, for example, can be utilised in foods that provide functionality not normally afforded by unmodified sources, such processing has a tendency to either alter other components of value or carry the perception of being undesirable due to processes involved in modification. Therefore it is preferable to provide sources of constituents that can be used in unmodified form in foods.

Barley (*Hordeum vulgare*) is the fourth largest cereal grain crop produced worldwide and is relatively underutilized in terms of human consumption aside from its use to produce alcoholic beverage. On average, barley grain contains about 64% starch, 11% protein and 5% β-glucan (normally 3-6%). The remaining 20% includes moisture, fiber and other minor components.

Known variation in barley starch structure is limited relative to the variation available in maize. Mutants in SBEIIb, corresponding to the amylose-extender phenotypes in maize or rice, have not been characterized in barley. The phenotype conferred by SBEIIa or SBEIIb mutations in barley is unknown. The most highly characterised mutations are waxy and a high amylose mutation identified as AC38. High Amylose Glacier (AC38) has relatively modest increases in amylose content to a maximum of about 45% of total starch. Double mutants with a waxy phenotype have also been constructed and analyzed (Schondelmaier et al., 1992; Fujita et al, 1999).

Other mutants of barley having high amylose starch contents have been identified. Chemically induced mutants in the SSIIa gene had higher levels of amylose in kernel starch, to about 65-70% (WO 02/37955 A1). The mutants M292 and M342 also showed substantially reduced average grain weight as a consequence of reduced starch synthesis, from a mean weight of about 51 mg for the parent line Himalaya to 32 and 35 mg for M292 and M342, respectively. Although the mutants retained the length and width of the wild-type grain, they were flattened from 2.8 mm average thickness for Himalaya to 1.6-1.8 mm thickness and had an essentially unfilled central region, which resulted in poorer milling characteristics. The ratio of grain length (L) to thickness (T) was found to be a useful diagnostic parameter for the mutant alleles, with mutants and wild-type seeds having an L:T ratio of >3.5 and <3.5 respectively. The starch content of the mutant lines was reduced from 49.0% for Himalaya to 17.7 and 21.9% for M292 and M342, respectively. It was shown that while there was a decrease in amylose content per grain from 6.2 mg per caryopsis to 4.0 and 4.8 mg in M292 and M342, respectively, there was a dramatic reduction in amylopectin content per caryopsis from 18.7 in Himalaya to 1.6 and 2.9 mg in the mutants. This showed that the high relative amylose level was a result of decreased amylopectin production. Grain β-glucan levels were increased in the mutants to above 10%. The starch showed reduced gelatinisation temperatures. The SSIIa mutants had an altered distribution of SBEIIa and SBEIIb activities between the starch granule and soluble fractions of the endosperm, however, they were essentially unaltered in the level of these activities in the endosperm as a whole (WO 02/37955; Morell et al., 2003).

Whilst elevated amylose starches of these types are useful, a barley starch with higher amylose contents is preferred, in particular if associated with improved starch synthesis and other characteristics, for example a reduced need for post-harvest modification. Such starch products are also relatively resistant to digestion and bring a greater health benefit.

General

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps. The present invention is not to be limited in scope by the specific embodiments described herein, which are intended for the purposes of exemplification only. Functionally-equivalent products, compositions and methods are clearly within the scope of the invention, as described herein.

Bibliographic details of the publications referred to by author in this specification are collected at the end of the description. The references mentioned herein are hereby incorporated by reference in their entirety. Reference herein to prior art, including any one or more prior art documents, is not to be taken as an acknowledgment, or suggestion, that said prior art is common general knowledge in Australia or forms a part of the common general knowledge in Australia.

As used herein, the term "derived from" shall be taken to indicate that a particular integer or group of integers has originated from the species specified, but has not necessarily been obtained directly from the specified source.

The designation of nucleotide residues referred to herein are those recommended by the IUPAC-IUB Biochemical Nomenclature Commission, wherein A represents Adenine, C represents Cytosine, G represents Guanine, T represents Thymidine.

SUMMARY OF THE INVENTION

In a first aspect the invention might be said to reside in grain obtained from a barley plant, the barley plant having a reduced level of SBEIIa enzyme activity in the endosperm, starch of said grain having a relative amylose content of at least 40% (w/w). The relative amylose content might preferably be higher than 50% or 75%, and preferably the grain is non-shrunken.

In a second aspect the invention might be said to reside in a barley grain comprising starch having a relative amylose content of at least 75% (w/w).

In a third aspect the invention might be said to reside in flour or wholemeal obtained from the grain of the first or second aspects of the invention, or food products incorporating such flour or wholemeal.

In a fourth aspect the invention might be said to reside in starch obtained from grain of a barley plant, the barley plant having a reduced level of SBEIIa enzyme activity in the endosperm, said starch being unmodified and having a relative amylose content of at least 40% (w/w). In a specific form of the fourth aspect the barley plant additionally has a reduced level of SBEIIb enzyme activity in the endosperm.

In a fifth aspect the invention might be said to reside in a composition comprising the starch according to the fourth aspect of the invention and another food ingredient or water.

In sixth aspect the invention might be said to reside in a composition comprising starch granules of barley endosperm and another food ingredient or water, wherein the starch of the starch granules comprises at least 75% (w/w) amylose.

In a seventh aspect the invention might be said to reside in a barley plant having a reduced level of SBEIIa enzyme activity, wherein starch in grain of the barley plant has a relative amylose content of at least 40% (w/w) or preferably at least 50% or at least 75%.

In an eight aspect the invention might be said to reside in a method of producing a barley plant with a reduced level of SBEIIa enzyme activity in the endosperm, starch of grain of the barley plant having an amylose content of at least 40% (w/w), the method comprising the steps of, a) introducing a genetic variation into a parent barley plant; and b) identifying progeny plants or seed of the parent barley plant that have reduced SBEIIa activity.

In a ninth aspect the invention might be said to reside in a method of producing a barley plant having reduced activity of both SBEIIa and SBEIIb enzyme activities in the endosperm which comprises: a) mutagenizing seed from a plant having reduced activity of SBEIIa enzyme activity; or b) mutagenizing seed from a plant having reduced activity of SBEIIb enzyme activity; or c) crossing a plant having reduced SEBEIIa enzyme activity with a plant having reduced SBEIIb enzyme activity; and identifying a barley plant having reduced activity of both SBEIIa and SBEIIb.

BRIEF DESCRIPTION OF THE DRAWINGS

FIG. 1. Nucleotide sequence of the barley SBEIIa cDNA (SEQ ID No. 1).

FIG. 2. Nucleotide sequence of the barley SBEIIb cDNA (SEQ ID No. 2).

FIG. 3. Sequence of the Starch Branching Enzyme IIa gene (SEQ ID No. 3) (wSBE II-D1) from *A. tauschii*, corresponding to the D genome SBEIIa gene of hexaploid wheat (*T. aestivum*).

FIG. 4. Partial wheat SBEIIb gene sequence (SEQ ID No. 4) (wbe2b genomic).

FIG. 5. Schematic of duplex-RNA constructs. A. The order of the gene elements used were promoter, SBEIIa or SBEIIb gene sequence (exons 1, 2 and 3) in sense orientation, intron (intron 3), SBEIIa or SBEIIb gene sequence (exons 1, 2, 3 and 4) in antisense orientation, and transcription terminator/polyadenylation sequence. B. The transcript of the ds-SBEIIa and ds-SBEIIb genes forms a "hairpin" RNA structure with a double-stranded region formed by hybridization between the sense and antisense sequences. The intron sequence bordered by the G and AG nucleotides is spliced out.

FIG. 11A, seed with wild type SBEIIa expression (line IIa4.2.3). FIG. 11B, seed which lack SBEIIa expression (line IIa4.2.5). A significant morphological alteration was observed in starch from seeds lacking SBEIIa but not for SBEIIb.

DETAILED DESCRIPTION OF THE INVENTION

Alteration of SBEIIa in Barley

Figure 6:
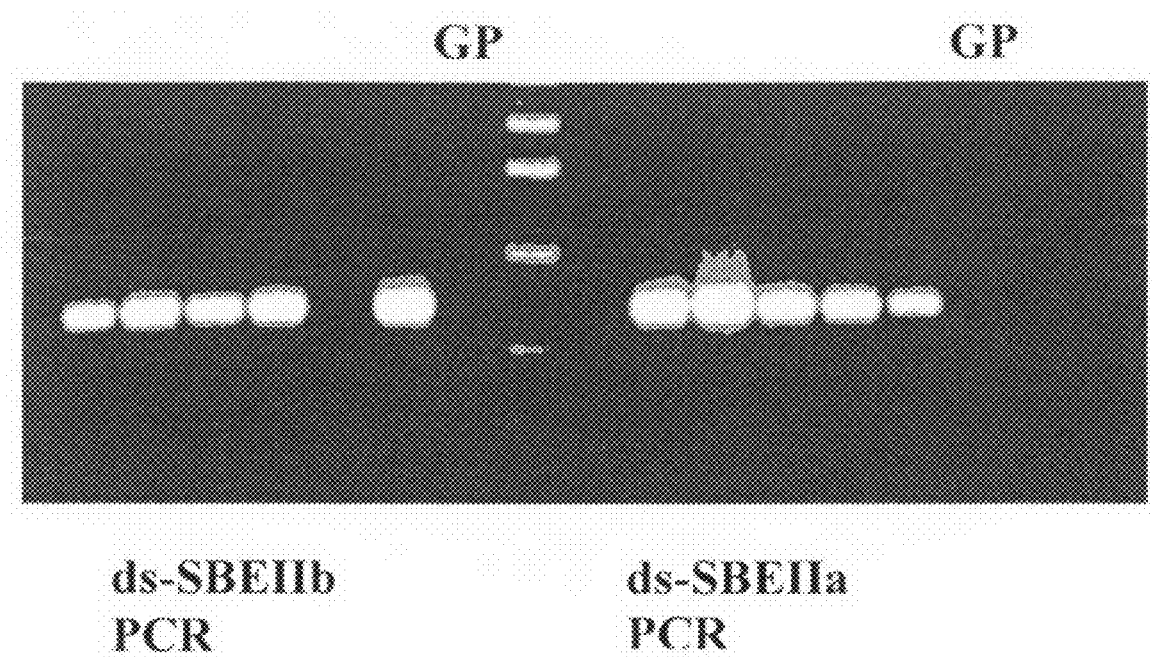
FIG. 6. PCR analysis of ds-SBEIIa and ds-SBEIIb transgenic lines of barley. The primer pairs BX17F/AR2bkpnR for SBEIIb and BX17F/AR2akpnR for SBEIIa that amplifies the first and second fragments of respective constructs which included the exons 1, 2, 3 and intron 3 (sense orientation) were used to identify positive transgenic lines. GP is for the untransformed Golden Promise. The central lane shows molecular size markers.

The invention is based on the finding that a reduction in SBEIIa activity in barley endosperm results in modified starch production, particularly high amylose accumulation in the barley grain. This unexpected result is in contrast to the findings in maize and rice where mutation in SBEIIa did not alter the amylopectin profile (Blauth et al., 20001, Nakamura, 2000). Preferably, there is an alteration in one or more additional starch biosynthetic enzyme activities, and more preferably a reduction in SBEIIb as well as SBEIIa. Preferably also the grain of this barley plant is non-shrunken.

Method of Producing a Barley Plant

In an aspect, the invention provides a method of reducing starch branching enzyme IIa (SBEIIa) activity in the endosperm of barley. The reduction in activity may be by at least 40% or perhaps preferably by at least 50% compared to the level of activity in the endosperm of unmodified (control) barley, more preferably by at least 75%, and even more preferably by at least 90% or 95%. The method may comprise the alteration of the expression of the SBEIIa gene of barley, or it may comprise the mutation of the SBEIIa gene in barley, whereby the SBEIIa activity in endosperm is reduced.

The method may comprise the step of determining the activity of SBEIIa in barley endosperm, preferably by measuring the level of the protein, for example by immunodetection, or the level of its corresponding mRNA by methods well known in the art, such as Northern blot hybridization analysis or reverse transcription polymerase chain reaction (RT-PCR). The method may further comprise the step of selecting or screening for a barley plant or grain having reduced SBEIIa activity in its endosperm. The selection step may be based on the reduced level of the SBEIIa activity or protein, or it may be based on the phenotype of the grain of the barley plant such as increased amylose content or decreased amylopectin content or a visual phenotype, for example shrunken grain.

SBE activity may be measured by enzyme assay, for example by the phosphorylase stimulation assay (Boyer and Preiss, 1978). This assay measures the stimulation by SBE of the incorporation of glucose 1-phosphate into methanol-insoluble polymer (α-D-glucan) by phosphorylase a. SBE activity can be measured by the iodine stain assay, which measures the decrease in the absorbance of a glucan-polyiodine complex resulting from branching of glucan polymers. SBE activity can also be assayed by the branch linkage assay which measures the generation of reducing ends from reduced amylose as substrate, following isoamylase digestion (Takeda et al., 1993a). Preferably, the activity is measured in the absence of SBEI or SBEIIb activity. Isoforms of SBE show different substrate specificities, for example SBEI exhibits higher activity in branching amylose, while SBEIIa and SBEIIb show higher rates of branching with an amylopectin substrate. The isoforms may also be distinguished on the basis of the length of the glucan chain that is transferred.

In a further aspect, the invention provides a method of reducing the activity of multiple starch biosynthesis enzymatic activities in barley endosperm, wherein one of the activities is SBEIIa. Preferably, the activities of both SBEIIa and SBEIIb are reduced, and even more preferably SBEI activity is also reduced. Other starch biosynthesis enzymatic activities that may be reduced in combination with SBEIIa are: SSI, SSII, SSIII. Starch debranching enzymes may also be altered, for example the activity of isoamylase or pullulanase. In a further embodiment, the activities of starch biosynthesis enzymatic activities may be altered in the plant in tissues other than endosperm, for example the activity of SBEI or SBEII may be increased in leaves to compensate for some loss of activity caused by a transgene encoding an SBEIIa-inhibitory molecule intended primarily for expression in the endosperm. Alternatively, starch synthesis may be further improved by the overexpression of one or more starch biosynthetic enzymes in combination with a reduction in SBEIIa. Genes encoding such enzymes may be from any of a variety of sources, for example from bacterial or other sources other than barley, and may be modified to alter the catalytic properties, for example alteration of the temperature dependence of the enzymes (WO94/09144).

In a further aspect, the invention provides a method of increasing the level of amylose (as a percentage of starch) in barley grain, comprising the step of reducing the activity of SBEIIa in barley endosperm. The amylose content is preferably at least 50%, more preferably at least 60% and even more preferably at least 65, 75% or 70%. In further preferred embodiments of the invention, the method provides for amylose contents of at least 80% or 90%, as exemplified herein.

The high amylose phenotype may be achieved by partial or full disruption to the expression of the SBEIIa gene, or the SBEIIa and SBEIIb genes. The extent to which the gene is inhibited will in some degree determine the characteristics of the starch made in the barley grain. Any of a range of gel electrophoresis techniques carried out on the proteins extracted from the modified barley endosperm will reveal the nature and extent of modification to the SBEIIa and/or SBEIIb activity. Modification may occur as a reduction in SBEIIa and/or SBEIIb activity, complete abolition of enzyme activity, or an alteration in the distribution of the SBEIIb or other enzymes within the endosperm. To carry out these tests, starch may be extracted from the barley endosperm and the proteins therein analyzed, for example as outlined in Rahman et al, 1995. Techniques well known in the art such as SDS-PAGE and immunoblotting are carried out on the soluble and the starch granule fractions and identify the plants or grain where modifications have occurred to the SBEIIa and/or SBEIIb enzymes.

Barley Plants

In a further aspect, the invention provides a barley (*Hordeum vulgare*) plant with a reduced level of SBEIIa activity in the endosperm during at least some of the development of the grain, the barley plant being capable of bearing grain having starch comprising a high relative amylose content. Preferably, the level of SBEIIa is reduced in the endosperm by at least 50%, more preferably by at least 75% and most preferably by at least 90% or 95% compared to the wild-type. The term "wild-type" has its normal meaning in the field of genetics and includes barley cultivars or genotypes which are not modified as taught herein.

The invention also provides progeny plants and grain which have the desired characteristics of the parent.

The invention also encompasses barley plants that have altered SBEIIb or other starch biosynthetic enzyme activities in addition to reduced SBEIIa activity. Plants having reduced SBEIIa and SBEIIb activities may be produced by crossing a plant reduced for SBEIIa with a plant reduced for SBEIIb, or by introducing a transgene encoding a molecule that inhibits expression of both SBEIIa and SBEIIb genes. The invention also encompasses the mutation(s) in other genetic backgrounds. The original altered (mutant) plants may be crossed with plants containing a more desirable genetic background. After the initial crossing, a suitable number of backcrosses may be carried out to remove the less desirable background. The desired genetic background may include a suitable combination of genes providing commercial yield and other characteristics such as agronomic performance, abiotic stress resistance or hull-less grain. The genetic background might also include other altered starch biosynthesis or modification genes, for example the amylose extender phenotype or the amo1 mutation in High Amylose Glacier barley (gene unknown), the waxy mutation (found for example in the Waxiro variety), the mutant gene in the high amylose variety MK6827 (available from the USDA ARS National Small Grain Germplasm Research Facility Aberdeen, Id. 831290 USA) or the high amylose varieties M292 and M342 (mutation in the SSIIa gene) or modifier genes. Additionally it may be desirable to combine other double and triple mutations with combinations of the above lines and in crosses with other barley lines that have a shrunken endosperm where the causal gene is not known.

Grain

The invention also provides barley grain comprising an altered starch compared to wild-type. The altered starch is at least partly a consequence of reduced SBEIIa activity during development of endosperm of the barley grain. The grain comprises increased amylose levels as a percentage of total starch and a reduced amylopectin content compared to wild-type, which has approximately 25% amylose and 75% amylopectin. Preferably, both SBEIIa and SBEIIb activities are reduced during development of the endosperm. Even more preferably, the activity of SBEI is also reduced. The amylose levels, as measured by methods well understood in the art, are preferable at least 50% of the total starch, more preferably at least 60% and even more preferably at least 65%, 70%, 75%, 80% or 90%. Increased amylose levels may be evidenced by abnormal starch granule morphology or loss of birefringence of the granules when observed under a light microscope or other methods. Preferably the amylose level is measured by an iodometric method, which may be spectrophotometric (for example, Morrison and Laignelet, 1983) or by high-performance liquid chromatography (HPLC, for example, Batey and Curtin, 1996).

The grain of the barley plant may have an elevated level of β glucan, which may be associated with increased carbon flow into this polymer rather than into amylopectin synthesis. Alternatively, the grain may have normal levels of β glucan, for example in the range 3.0-6.0% of the mature grain weight. More preferably, the grain comprises both elevated amylose and normal levels of β glucan. Such a combination is unexpected, based on the composition of starch in grain from SSIIa mutant barley (WO 02/37955). The grain may comprise starch that has altered gelatinisation temperatures and/or altered swelling characteristics during and following gelatinisation. The grain also, preferably, has a non-shrunken phenotype.

The invention also provides flour or meal produced from the grain. These may be unprocessed or processed, for example by fractionation or bleaching. The invention further provides barley grain useful for food production obtained from a barley plant having an altered level of a SBEIIa activity in the endosperm, starch of said grain having a high amylose content and a reduced amylopectin content. Additionally the invention encompasses grain that has been processed in other ways, so that the grain may have been milled, ground, pearled, kibbled or cracked.

Starch

In another aspect, the invention provides starch obtained from the grain of the barley plant as described above, the plant having a reduced level of SBEIIa activity in the endosperm, the starch having a high amylose content and a reduced amylopectin content. Preferably both SBEIIa and SBEIIb activities are reduced, and more preferably the activity of SBEI is also reduced. In another aspect, the invention provides starch obtained from the grain of the barley plant, comprising at least 50% amylose, preferably at least 60% amylose, and even more preferably at least 65%, 70%, 75%, 80% or 90% amylose.

Purified starch may be obtained from grain by a milling process, for example a wet milling process, which involves the separation of the starch from protein, oil and fibre. The initial product of the milling process is a mixture or composition of starch granules, and the invention therefore encompasses such granules. The starch of the granules comprises at least 50%, preferably 70%, 75% or 80% amylose.

The starch may comprise an elevated level of resistant starch, with an altered structure indicated by specific physical characteristics including one or more of the group consisting of physical inaccessibility to digestive enzymes which may be by reason of having a high β-glucan content, altered starch granule morphology, the presence of appreciable starch associated lipid, altered crystallinity, and altered amylopectin chain length distribution. The high amylose content also contributes to the level of resistant starch.

The invention also provides starch from grain of the exemplified barley plant comprising increased amounts of dietary fibre, preferably in combination with the elevated level of resistant starch. This increase is also at least in part a result of the high relative level of amylose.

Methods of Reducing Gene Activity: Transgenes

The activity of SBEIIa and optionally other starch biosynthesis or modification genes are preferably altered by introducing a genetic variation into the plant which might be by means of the introduction of a transgene into the barley plant. A "genetic variation" means any alteration in the genome which, in this context, affects the activity of SBEIIa, and includes mutations such as point mutations, substitutions, inversions, translocations and preferably deletions, as well as introduction of transgenes. A "transgene" as referred to herein has the normal meaning in the art of biotechnology and includes a genetic sequence which has been produced or altered by recombinant DNA or RNA technology and which has been introduced into the organism or cell of interest. The transgene may include genetic sequence derived from the organism or cell, for example an antisense sequence. The transgene typically includes an exogenous nucleic acid which is not derived from said organism or cell. "Transgenic" refers to the organism or cell containing a transgene. "Non-transgenic" refers to the absence of any transgene in the genome. A transgene is preferably integrated into the genome of the organism or cell, for stable inheritance.

The method of reducing SBEIIa activity may comprise the step of introducing a transgene into a regenerable cell of barley and regenerating a transgenic barley plant from the transformed cell. The branching enzymes involved in synthesis of amylopectin include SBEI, SBEIIa and SBEIIb and the invention encompasses a reduced expression of SBEIIa alone or in combination with alteration of SBEIIb or SBEI expression. Therefore, the transgene(s) may inactivate more than one of these genes. Moreover, the inactivation of SBEIIb and/or SBEI may be direct, in that the transgene (e.g. encoding duplex RNA, antisense, or ribozyme RNA, see below) directly targets the SBEIIb or SBEI gene expression, or it may indirectly result in the alteration in the expression of SBEIIb or SBEI. For example, the transgene RNA may target only the SBEIIa gene/RNA in terms of sequence identity or basepairing but also result in reduction of SBEIIb or SBEI by altering protein stability or distribution. Additionally forms of the present invention reside in the combination of an altered activity of SBEIIa and an alteration of one or more other amylopectin synthesis enzymes, which enzymes may include SSI, SSII, SSIII, and debranching enzymes such as isoamylase or pullulanase. Expression of any or all of these may be altered by introduction of a transgene.

Several DNA sequences are known for amylopectin synthesis genes in barley, any of which can be the basis for designing transgenes for inactivation of the genes in barley. These include SBEIIa (GenBank accession numbers AF064562 and AF064560), SBEIIb (GenBank accession numbers AF064563 and AF064561). Homologs of the SBEI gene of barley can be isolated by utilising sequences based on DNA sequences from other grains, for example by techniques such as those set out in WO99/14314 to Li et al., for *Triticum*. The *Triticum tauschii* sequence for SBEI, which is highly homologous to the wheat D genome SBEI gene and has a high degree of similarity to the barley gene, can be found in published Patent specification WO 99/14314 or referenced cited therein, which document is incorporated herein by reference. The sequence for SBEI of wheat can be accessed in the GenBank database under accession number AF076679. Homologues of other amylopectin synthesising genes from wheat or other closely related species can also be used to modify gene expression levels in barley. Such genes or fragments thereof can be obtained by methods well known in the art, including PCR amplification or hybridization to labeled probes.

"Stringent hybridization conditions" as used herein means that hybridization will generally occur if there is at least 90% and preferably at least 95% sequence identity between the probe and the target sequence. Examples of stringent hybridization conditions are overnight incubation in a solution comprising 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

The region(s) of the homologues used in preparing the transgene construct should have at least 85% identity to the corresponding barley gene, preferably at least 90% and even more preferably 95-100% identity in the appropriate region. It is also preferred that the transgene specifically target the amylopectin synthesis genes expressed in the endosperm of barley and have less or minimal effect on amylopectin synthesis elsewhere in the plant. This may be achieved by use of suitable regulatory sequences such as endosperm-specific promoters in the transgene.

Antisense

Known genetic engineering or transgenic approaches to altering, in particular specifically reducing, gene activity in plants are well known in the art. These methods of introducing genetic variation into the barley plant include the expression of a suitable antisense molecule that is complementary to the RNA of the target gene and can hybridize with it. Antisense molecules are thought to interfere with the translation or processing or stability of the mRNA of the target gene, thereby inactivating its expression. Methods of devising antisense sequences are well known in the art and examples of these are can be found in U.S. Pat. No. 5,190,131, European patent specification 0467349-A1, European patent specification 0223399-A1 and European patent specification 0240208, which are incorporated herein by reference. The use of antisense techniques in plants has been reviewed by Bourque (1995) and Senior (1998). Bourque lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior (1998) states that antisense methods are now a very well established technique for manipulating gene expression.

Antisense molecules for barley SBEIIa, SBEIIb, SBEI or other amylopectin biosynthesis genes can be based on the barley mRNA sequences or based on homologies with DNA or mRNA sequences derived from other species, for example wheat. These antisense sequences may correspond to the structural genes or for sequences that effect control over the gene expression or splicing event. For example, the antisense sequence may correspond to the targeted coding region of the barley SBEIIa or other gene, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition. The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of homology of the antisense sequence to the targeted transcript should be at least 85%, preferably at least 90% and more preferably 95-100%. The antisense RNA molecule may of course comprise unrelated sequences which may function to stabilize the molecule.

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of homology to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches.

Double Stranded RNA-Mediated Gene Silencing

A further method that might be employed to introduce genetic variation into the barley plant is duplex or double stranded RNA mediated gene silencing. This method also involves PTGS. In this method a DNA is introduced that directs the synthesis of an at least partly double stranded RNA product(s). The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule triggers a response from an endogenous plant system that destroys both the double stranded RNA and also the homologous RNA transcript from the target plant gene, efficiently reducing or eliminating the activity of the target gene. Reference is made to Australian Patent specification 99/292514-A and Patent specification WO 99/53050 for methods of implementing this technique. The length of the sense and antisense sequences that hybridise should each be at least 19 contiguous nucleotides, preferably at least 50 nucleotides, and more preferably at least 100, 200, 500 or 1000 nucleotides. The full-length sequence corresponding to the entire gene transcript may be used. The lengths are most preferably 100-2000 nucleotides. The degree of homology of the sense and antisense sequences to the targeted transcript should be at least 85%, preferably at least 90% and more preferably 95-100%. The RNA molecule may of course comprise unrelated sequences which may function to stabilize the molecule.

Ribozymes

Ribozymes may be used to introduce the genetic variation responsible for inactivation of the desired gene expression in barley. Ribozymes are RNA molecules with enzymatic or catalytic function that can cleave other RNA molecules at specific sites defined by one or often two hybridizing sequences. The cleavage of the RNA inactivates the expression of the target gene. The ribozymes may also act as an antisense molecule, which may contribute to the gene inactivation. The ribozymes contain one or more catalytic domains, preferably of the hammerhead or hairpin type, between the hybridizing sequences. Other ribozyme motifs may be used including RNAseP, Group I or II introns, and hepatitis delta virus types. Reference is made to European patent specification 0321201 and U.S. Pat. No. 6,221,661. The use of ribozymes to inactivate genes in transgenic plants has been demonstrated, for example by Wegener et al (1994).

Genetic Constructs/Vectors

The invention also provides isolated nucleic acid molecules including RNA and preferably DNA which encode the gene-inhibiting molecule. Preferably, the nucleic acid molecules encode the antisense, sense (co-suppression), double-stranded RNA or ribozyme molecules targeting the barley SBEIIa gene sequence and effective in inactivating its expression in endosperm of barley grain. The invention also provides genetic constructs comprising the isolated nucleic acid molecule, comprising one or more regulatory elements such as promoters, enhancers and transcription termination or polyadenylation sequences. Such elements are well known in the art. The genetic constructs may also comprise intron sequences which aid expression of the transgene in plants, particularly in monocotyledonous plants such as barley. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not.

The invention further provides vectors, for example plasmid vectors, comprising the genetic constructs. The term "vector" includes an expression vector, being capable of in vitro or in vivo expression, and a transformation vector, capable of being transferred from one cell or organism to another. The vectors comprise sequences that provide for replication in cells, for example in prokaryotic cells such as *E. coli* or *Agrobacterium*. Preferably, the vector is a binary vector comprising a T-DNA sequence, defined by at least one T-DNA border sequence, that can be introduced into barley cells. The invention further provides cells comprising the vectors, for example *Agrobacterium* or barley cells which may be regenerable cells such as the cells of the scutellum of immature embryos. Alternatively, the cells may be transformed barley cells comprising the transgene.

Promoters/Terminators

The transgene or other genetic construct of the invention may include a transcriptional initiation region (promoter) which may provide for regulated or constitutive expression in the endosperm of barley. The promoter may be tissue specific, conferring expression selectively or exclusively in the endosperm. The promoter may be selected from either endosperm-specific (such as High Molecular Weight Glutenin promoter, the wheat SSI promoter, wheat SBEII promoter, wheat GBSS promoter) or promoters not specific for the endosperm (such as ubiquitin promoter or CaMV35S or enhanced 35S promoters). The promoter may be modulated by factors such as temperature, light or stress. Ordinarily, the promoter would be provided 5' of the genetic sequence to be expressed. The construct may also contain other elements that enhance transcription such as the nos 3' or the ocs 3' polyadenylation regions or transcription terminators. The regions of DNA illustrated will be incorporated into vectors containing suitable selectable marker gene sequences and other elements, or into vectors that are co-transformed with vectors containing these sequences.

Transformation Methods for Barley

Methods for transformation of monocotyledonous plants such as barley for introducing genetic variation into the plant by introduction of an exogenous nucleic acid and for regeneration of plants from protoplasts or immature plant embryos are well known in the art, see for example, Wan and Lemaux (1994), Tingay et al (1997), Canadian Patent Application 2092588 by Nehra, Australian Patent Application No 61781/94 by National Research Council of Canada, Australian Patent No 667939 by Japan Tobacco Inc., International Patent Application PCT/US97/10621 by Monsanto Company, U.S. Pat. No. 5,589,617, and other methods are set out in Patent specification WO99/14314. Vectors carrying the desired nucleotide sequence or genetic construct and a selectable marker may be introduced into regenerable barley cells of tissue cultured plants or explants, or suitable plant systems such as protoplasts. The selectable marker gene may provide antibiotic or herbicide resistance to the barley cells, or allow the utilization of substrates such as mannose. The selectable marker preferably confers hygromycin resistance to the barley cells. The regenerable barley cells are preferably from the scutellum of immature embryos, mature embryos, callus derived from these, or the meristematic tissue.

The transformed plant may contain a selectable marker gene, or such gene may be removed during or after regeneration, for example by excision of the selectable marker gene out of the genome or by segregation of the selectable marker gene away from the SBEIIa-inhibiting transgene.

Plants where the transgene or mutation has been integrated into a chromosome can be screened for by, for example, using a suitable nucleic acid probe specific for the transgene or phenotypic observation. Any of several methods may be employed to determine the presence of a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed or mutant may also be identified i.e. distinguished from non-transformed or wild-type plants by their phenotype, for example conferred by the presence of a selectable marker gene, or the presence of a particular protein by immunological methods, or by the absence of a protein, for example that absence of the SBEIIa protein in the endosperm as detected by ELISA assay. An indication used in screening such plants might also be by observation of the phenotypic traits of the grain, for example by visual inspection or measurement of shrunken grain, or testing for elevated amylose content, or checking microscopically for the presence of birefringence.

Mutation

Introduction of the genetic variation leading to reduced activity of the SBEIIa enzyme or other enzyme in the barley endosperm may also be achieved by the appropriate mutations within the respective gene or regulatory sequences of the gene. The extent to which the gene is inhibited will to some degree determine the characteristics of the starch made. The mutations may be truncation or null mutants and these are known to have a significant impact on: the nature of the starch, however an altered amylopectin structure will also result from a leaky mutant that sufficiently reduces amylopectin synthesis enzyme activity to provide the characteristic of interest in the starch or grain of barley. Other chromosomal rearrangements may also be effective and these might include deletions, inversions, duplication or point mutations.

Mutagenesis can be achieved by chemical or radiation means, for example EMS or sodium azide (Zwar and Chandler, 1995) treatment of seed, or gamma irradiation. Isolation of mutants may be achieved by screening mutagenized plants or seed. For example, a mutagenized population of barley may be screened for high amylose content in the grain and/or longer than normal amylopectin chain length distribution, or loss of the SBEIIa protein by ELISA, or for altered grain morphology (Green et al., 1997). Screening is preferably done in a barley genotype which already lacks one of the SBE activities, for example in a SBEIIb-negative background. Such mutations may then be introduced into desirable genetic backgrounds by crossing the mutant with a plant of the desired genetic background and performing a suitable number of backcrosses to cross out the originally undesired parent background.

Mutations in the genes encoding the SBEIIa or other enzymes involved in amylopectin synthesis will generally cause increased relative amylose content. The amount of amylose per individual grain may be increased as a consequence of diverted carbon flow from amylopectin to amylose, or it may be decreased if there is a significant decrease in starch production per grain. In either case, the relative level of amylose as a percentage of starch increases.

Suitable for Food Production

In another aspect, the invention provides barley that is useful for food production, the grain being obtained from a barley plant having a reduced level of SBEIIa activity in the endosperm of developing grain, starch of said grain having a relatively high amylose content and a reduced amylopectin content. The barley plant of the present invention is preferably one having grain that is useful for food production and in particular for commercial food production. Such food production might include the making of flour or other products that might be an ingredient in commercial food production.

The desired genetic background of the barley will include considerations of agronomic yield and other characteristics. Such characteristics might include whether it is desired to have a winter or spring type of barley, agronomic performance, disease resistance and abiotic stress resistance. In Australia one might want to cross into barley cultivars such as Sloop, Schooner, Chebec, Franklin, Arapiles, Tantangara, Galleon, Gairdner or Picola. The examples provided are specific for an Australian production region, and other varieties will be suited for other growing regions. It is preferred that the barley variety of the invention provide a yield not less than 80% of the corresponding wild-type variety in at least some growing regions, more preferably not less than 90% and even more preferably not less than 95%. The yield can readily be measured in controlled field trials. It is also preferred that the barley plants are hull-less or "naked", because the presence of husks on barley grains introduces greater difficulty in processing the grain.

The starch content of the grain should be at least about 12% (w/w) or 15%, preferably at least 25%, more preferably at least 35% and even more preferably near to the wild-type levels of 45-50% (w/w). Lower starch contents than wild-type are likely a consequence of reduced amylopectin levels. The grain may still be useful for commercial food production because of the relatively high value of the high amylose products. Other desirable characteristics include the capacity to mill the grain. Whilst pearled barley may be produced from most forms of grain, certain configurations of grain are particularly resistant to milling. Another characteristic that might have an impact on commercial usefulness of grain is the coloration of the product produced from the grain. Where the husk or other portion of the grain exhibits significant coloration other than the normal this may limit its commercial applications to niche applications such as being a component of bread containing coloured whole or kibbled grains. Typically in barley the significant coloration is purple, and that may be a bright and strong coloration which is highly undesirable in most food products. Another aspect that might make a barley plant of higher value is the degree of starch extraction from the grain, the higher extraction rates being more useful. Grain shape is also another feature the can impact on the commercial usefulness of a plant, thus grain shape can have an impact on the ease or otherwise with which the grain can be milled. For example, the barley grain of the high amylose MK6827 plant has a very elongated grain morphology which makes it difficult to mill and process. A convenient measure of this elongate shape and associated usefulness is the ratio of the length of the grain to the thickness of the grain (L/T ratio). This ratio is often dictated by the nature of the starch. It is preferred that this ratio is less than 5.5, more preferably ranging from about 4 to about 5, and most preferably less than 3.5 on average.

A fuller grain may be desirable in terms of achieving greater yields and certain benefits of the invention might be achieved, such as the production of starch with high levels of amylose, or in the alternative starch with altered chain length distributions. Thus the grain preferably has a non-shrunken phenotype. Other aspects of the invention may, however, be better achieved by a grain that is less filled. Thus the proportion of aleurone layer or germ to starch may be higher in less filled grain, thereby providing for a barley flour or other product that is higher in the beneficial constituents of the aleurone layer. The high aleurone layer product might thus be higher in certain vitamins such as folate, or it might be higher in certain minerals such as calcium, and that combined with higher resistant starch levels and/or higher β glucan levels might provide synergistic effects such as providing for enhanced uptake of minerals in the large bowel.

In order to maximise the amount of amylose, it may be desirable for the barley plant to also have other phenotypic characteristics in addition to a reduced activity of SBEIIa. The genetic background might therefore include additionally the amo1 mutation in AC38 (causal gene unknown) or the waxy mutation (found for example in the Waxiro variety). Additionally it might be desired to make double mutations in other barley mutants available with shrunken endosperms where the causal gene is not known.

Starch is readily isolated from barley grain using standard methods, for example the method of Schulman et al. (1991). On an industrial scale, wet or dry milling can be used. The starch obtained from the grain of barley plant of the invention has a high relative amylose content. Barley plants having at least 35-45% amylose in the starch are considered to be high amylose. The present invention however provides for barley with an amylose content that is greater than 50% (w/w), preferably at least 60%, and more preferably at least 70%, 75%, 80% or 90%.

It will be understood that the relative level of amylose referred to is in relation to total starch content, and thus the remainder of the starch might be predominantly of an intermediate type of starch or it might be predominantly amylopectin or a mixture of both.

β Glucan

It is known that there is a wide variation in β glucan levels in barley in the range of about 4% to about 18% by weight of the barley, but more typically from 4% to about 8% (for example, Izydorcyk et al., 2000). Enhanced barley strains have been developed, for example, which have between about 15% and about 18% by weight β-glucan but has a waxy phenotype.

The levels of β glucan contemplated by this invention may depend on the genetic background in which the amylopectin synthesis enzyme activity, including SBEIIa, is reduced. The exemplified embodiment shows relatively normal β glucan synthesis, however other forms of the invention may contemplate an elevated relative level of β glucan. Thus the grain of the barley plant preferably has a β glucan content of between about 3 to 6% (w/w) of total non-hulled grain weight. Other forms of the invention may however exhibit β-glucan content of greater than 6% or higher, for example, 6-8%. Levels of β glucan in a waxy mutant has been measured as being as high as 15 to 18%, for example variety Prowashonupana, sold commercially under the name Sustagrain™, (ConAgra™ Specially Grain Products Company, Omaha, Neb. USA) and the present invention may contemplate levels as high, or higher, than that.

Gelatinisation Temperature

Gelatinisation is the collapse (disruption) of molecular order within the starch granule with concomitant and irreversible changes in properties such as granular swelling, crystallite melting, loss of birefringence, viscosity development and starch solubilisation. High amylose starch from ae (amylose extender) mutants of maize showed a higher gelatinisation temperature than normal maize (Fuwa et al., 1999, Krueger et al., 1987). On the other hand, starch from barley sex6 mutants that lack starch synthase IIa activity had lower gelatinisation temperatures and the enthalpy for the gelatinisation peak was reduced when compared to that from control plants (Morell et al., 2003).

In another aspect of the invention, the starch may have an altered gelatinisation temperature as measured by differential scanning calorimetry. This may be either increased or reduced compared to starch from wild-type plants. The altered gelatinisation temperature may be in addition to the relatively high amylose content. Where the gelatinisation temperature is reduced, it may be reduced when compared to starch produced by other barley varieties with elevated amylose content, or it may be reduced when compared with starch produced from barley with normal levels of amylose. Alternative forms of the invention contemplate gelatinisation temperatures that are unaltered or are raised relative to wild-type barley starch. The gelatinisation temperature of wild-type barley starch is typically about 56° C. for the temperature of the first peak as measured by differential scanning calorimetry.

Swelling Volume

The starch may also be characterized by its swelling rate in heated excess water compared to wild-type starch. Swelling volume is typically measured by mixing either a starch or flour with excess water and heating to elevated temperatures, typically greater than 90° C. The sample is then collected by centrifugation and the swelling volume is expressed as the mass of the sedimented material divided by the dry weight of the sample. A low swelling characteristic is useful where it is desired to increase the starch content of a food preparation, in particular a hydrated food preparation.

Crystallinity

The starch structure of the barley of selected forms of the present invention may also differ in that the degree of crystallinity is reduced compared to normal starch isolated from barley. The reduced crystallinity of a starch is also thought to be associated with enhance organoleptic properties and contributes to a smoother mouth feel. Thus the starch may additionally exhibit reduced crystallinity resulting from reduced levels of activity of one or more amylopectin synthesis enzymes Crystallinity is typically investigated by X-ray crystallography.

Distribution of Amylopectin Chain Lengths

One measurement of an altered amylopectin structure is the distribution of chain lengths, or the degree of polymerization, of the starch. The chain length distribution may be determined by using fluorophore-assisted carbohydrate electrophoresis (FACE) following isoamylase de-branching. The amylopectin of the starch of the invention may have a distribution of chain length in the range from 5 to 60 that is greater than the distribution of starch from wild-type plants upon debranching. Starch with longer chain lengths will also have a commensurate decrease in frequency of branching. Thus the starch may also have a distribution of longer amylopectin chain lengths in the amylopectin still present.

Food Characteristics

Starch is the major source of carbohydrate in the human diet, and the grain of the invention and products derived from it can be used to prepare food. The food may be consumed by man or animals, for example in livestock production or in pet-food. The grain derived from the altered barley plant can readily be used in food processing procedures, and therefore the invention includes milled, ground, kibbled, pearled or rolled grain or products obtained from the processed or whole grain of the barley plant referred to above, including flour. These products may be then used in various food products, for example farinaceous products such as breads, cakes, biscuits and the like, or food additives such as thickeners or binding agents, or to make malted or other barley drinks, noodles and quick soups. The grain or products derived from the grain of the invention are particularly desired in breakfast cereals. The high amylose starches of the invention can also be used to form high strength gels which are useful in the confectionery industry, or allow lower molding and curing times. They may also be used as a coating, for example to reduce oil absorption in deep-fried potato or other foods.

Dietary Fibre

Dietary fibre, in this specification, is the carbohydrate and carbohydrate digestion products that are not absorbed in the small intestine of healthy humans but enter the large bowel. This includes resistant starch, β-glucan and other soluble and insoluble carbohydrate polymers. It is intended to comprise that portion of carbohydrates that are fermentable, at least partially, in the large bowel by the resident microflora.

The starch of the invention preferably contains relatively high levels of dietary fibre, more particularly amylose and optionally an elevated level of β-glucan. The dietary fibre content of the grain of the present invention may or may not result solely from the increased relative endospermal amylose content. The β-glucan may be present at elevated levels and as such may contribute significantly to the dietary fibre level.

Aspects of this invention might also arise from the combination of aleurone layer and germ in combination with high levels of dietary fibre. Specifically, this may arise where higher relative levels of aleurone or germ are present in the grain. Firstly, barley has a significantly higher aleurone layer than other commercial grains, being a result of having a three cell aleurone layer. Secondly, where the barley grain is slightly shrunken the endosperm is present in reduced amounts and the aleurone layer and the germ are present in relatively elevated amounts. Thus the barley has a relatively high level of certain beneficial elements or vitamins in combination with elevated resistant, such elements include divalent cations such as bioavailable $Ca^{++}$ and vitamins such as folate or antioxidant such as tocopherols and tocotrienols. Calcium is required for growth and deposition of bone and other calcified tissue and in lowering the risk of osteoporosis later in life. Folic acid is found to be protective against neural tube defects when consumed periconceptually and decreases the risk of cardiovascular disease, thereby enhancing the effects of the combination of resistant starch and β-glucan. Folic acid also is thought to have an effect of lowering the risk of certain cancers. Tocopherol and tocotrienols carry the benefits of antioxidants and are believed to lower the risk of cancer and heart disease, and also have the effect of reducing the undesirable effects of oxidation of components of a food such as fatty acids which can result in rancidity. One specific form of milled product might be one where the aleurone layer is included in the milled product. Particular milling process might be undertaken to enhance the amount of aleurone layer in the milled product. Such a method is referred to in Fenech et al. (1999). Thus any product derived from grain milled or otherwise processed to include aleurone layer and germ will have the additional nutritional benefits, without the requirement of adding these elements from separate sources.

Resistant Starch

Resistant starch is defined as the sum of starch and products of starch digestion not absorbed in the small intestine of healthy humans but entering into the large bowel. Thus, resistant starch excludes products digested and absorbed in the small intestine. Resistant starches include physically inaccessible starch (RS1 form), resistant granules (RS2), retrograded starches (RS3), and chemically modified starches (RS4).

The altered starch structure and in particular the high amylose levels of the starch of the invention give rise to an increase in resistant starch when consumed in food. Resistant starch may also increase if β-glucan is present at elevated levels, which is likely to exert protective effects by association of the β glucan with the starch granule. The starch may be in an RS1 form, being somewhat inaccessible to digestion. Starch-lipid association as measured by V-complex crystallinity is also likely to contribute to the level of resistant starch. In this case the resistance is likely to arise because of the physically inaccessible of the starch by virtue of the presence of the lipid and accordingly this might be regarded as an RS1 starch. The starch of the exemplified barley plant may be resistant to digestion by reason of the structure of the starch granule and accordingly may have RS2 starch. Each of these characteristics might be present separately or in combination.

It will be understood that one benefit of the present invention is that it provides for products that are of particular nutritional benefit, and moreover it does so without the need to modify the starch or other constituents of the barley grain. However it may be desired to make modifications to the starch, β-glucan or other constituent of the grain, and the invention encompasses such a modified constituent. Methods of modification are well known and include the extraction of the starch or β-glucan or other constituent by conventional methods and modification of the starches to increase the resistant form. The starch or β-glucan may be modified by treatment with heat and/or moisture, physically (for example ball milling), enzymatically (using for example α- or β-amylase, pullulanase or the like), chemical hydrolysis (wet or dry using liquid or gaseous reagents), oxidation, cross bonding with difunctional reagents (for example sodium trimetaphosphate, phosphorous oxychloride), or carboxymethylation.

Glycemic Index

Glycemic Index (GI) is a comparison of the effect of a test food with the effect of white bread or glucose on excursions in blood glucose concentration. The Glycemic Index is a measure of the likely effect of the food concerned on post prandial serum glucose concentration and demand for insulin for blood glucose homeostasis. One important product provided by the invention as a result of the high amylose and optionally high β-glucan content is a low calorific product with a reduced glycemic index. A low calorific product might be based on inclusion of flour produced from milled barley grain. It might be desired, however, to first pearl the grain removing perhaps 10% or 20% by weight of the grain, thereby removing the aleurone layer and at the greater reduction removing also the germ. The effect of the pearling step is to reduce the lipid content and therefore reducing the calorific value of the food. Such foods will have the effect of being filling, enhancing bowel health, reducing the post-prandial serum glucose and lipid concentration as well as providing for a low calorific food product. Use of the pearled product would result in a reduction in nutritional benefits provided by the aleurone layer and the germ. The flour produced from the pearled product is likely to have an enhanced appearance because a product made in that way tends to be whiter.

Non-Food Applications

The present invention provides modified or improved starches having elevated levels of amylose or reduced levels of amylopectin whose properties satisfy any of various industrial requirements. Starch is widely used in non-food industries, including the paper, textile, corrugating and adhesive industries (Young, 1984). The physical properties of unmodified starch limits its usefulness in some applications and often imposes a requirement for chemical modification that can be expensive or have other disadvantages.

The invention provides starch for which less post-harvest modification may be required, in particular due to the reduced amylopectin content in combination with other physical properties. For example, the pasting temperature, resistance to shearing stresses, film strength and/or water resistance of starches and product made from the grain of this invention may be altered. The starch may also be used to prepare a biodegradable loose-fill packing material that can be used as a replacement for polystyrene.

It will be understood that whilst various indications have been given as to aspects of the present invention, the invention may reside in combinations of two or more aspects of the present invention.

EXAMPLES

Example 1

Materials and Methods

Callus Inducing Medium

BCI-DM medium containing Dicamba (2.5 mg/l) was used for callus induction from barley embryo. Composition for one litre of medium:

| | |
|---|---|
| MS salt Macro (10x stock): | 100 ml |
| MS micro (100x stock): | 10 ml |
| Iron (200x stock): | 5 ml |
| EDTA (200x stock): | 5 ml |
| Maltose: | 15.0 g |
| Thiamine-HCl (1 mg/ml): | 1 ml |
| Myo-inositol: | 250 mg |
| Casein hydrolysate: | 1 g |
| Dicamba (1 mg/ml): | 2.5 ml |
| Proline: | 345 mg |

The pH was adjusted to 5.8 and 3.5 g/l of Phytagel added. After autoclaving the medium, 150 mg/l of Timentin and 50 mg/l of Hygromycin were added.

Barley Regeneration Medium

Barley calli are regenerated in FHG medium containing BAP (1 mg/l)

| | |
|---|---|
| FHG-I Macro (10x stock): | 100 ml |
| FHG-II Micro (100x stock): | 10 ml |
| Thiamine-HCl (1 mg/ml): | 1 ml |
| Iron (200x stock): | 5 ml |
| EDTA (200x stock): | 5 ml |
| BAP (1 mg/ml): | 1 ml |
| Inositol: | 100 mg |
| Glutamine: | 730 mg |
| Maltose: | 62 g |

The pH was adjusted to 5.8 and then 3.5 g/l of phytagel added. After autoclaving the medium, 150 mg/l of Timentin and 20 mg/l of hygromycin were added.

Carbohydrate Determination and Analysis

Starch was isolated from barley grain using the method of Schulman et al. (1991). Starch content was determined using the total starch analysis kit supplied by Megazyme (Bray, Co Wicklow, Republic of Ireland). The starch content is then compared to control plants. Subtraction of the starch weight from the total grain weight to give a total non-starch content of the grain determines whether the reduction in total weight is due to a reduction in starch content.

Determination of the amylose content or the amylose/amylopectin ratio was performed by an HPLC method for separating debranched starches or by an iodine binding method, as described by Batey and Curtin (1996). Briefly, starch was defatted by dissolving it in DMSO and reprecipitation with ethanol. After redissolving the starch in DMSO and the addition of water, further dilution, and addition of an iodine/potassium iodide solution, the absorbance of the solution was measured at 605 nm. The amylose content was determined from a standard curve obtained from mixtures of amylose and amylopectin covering the range 0-100% amylose. Analysis of the amylose/amylopectin ratio of non-debranched starches may also be carried out according to Case et al., (1998).

β-Glucan levels were determined using the kit supplied by Megazyme (Bray, Co Wicklow, Republic of Ireland).

Starches were debranched and chain length distributions analyzed using fluorophore assisted carbohydrate electrophoresis (FACE) using a capillary electrophoresis unit according to Morell et al (1998).

Differential Scanning Calorimetry (DSC)

DSC measures the changes to gelatinisation temperatures that have occurred in the starch by changes in amylose and amylopectin ratio. Gelatinisation was measured in a Pyris 1 differential scanning calorimeter (Perkin Elmer, Norwalk Conn., USA). Starch was mixed with water in the ratio of 2 parts water:1 part starch and this mixture (40-50 mg, accurately weighed) placed in a stainless steel pan and sealed. The sample was scanned at 10° C. per minute from 20° C. to 140° C. with an empty stainless steel pan as a reference. Gelatinisation temperatures and enthalpy were determined using the Pyris software.

RVA Analysis

Viscosity was measured on a Rapid-Visco-Analyser (RVA, Newport Scientific Pty Ltd, Warriewood, Sydney) using conditions as a reported by Batey et al., 1997 for wholemeal flours. In order to inhibit α-amylases, silver nitrate was included in all assays at a concentration of 12 mM. The parameters measured were peak viscosity (the maximum hot paste viscosity), holding strength, final viscosity and pasting temperature.

Flour Swelling

Flour swelling volume was determined according to the method of Konik-Rose et al (2001). Increased uptake of water was measured by weighing the sample prior to and after mixing the sample in water at defined temperatures and following collection of the gelatinized material.

Example 2

Isolation of SBE Genes from Barley

Construction of Barley cDNA and Genomic Libraries

Barley cDNA and genomic libraries were made by standard methods in phage vectors (Sambrook et al, 1989). A cDNA library was made in the ZipLox vector (Life Technology) according to the protocols supplied with the reagents. The titre of the library was 2×10$^6$ pfu tested with Y1090 (ZL) strain of E. coli. The barley genomic library, obtained from E. Lagudah (CSIRO), was made from DNA from the variety Morex. The DNA was digested with MboI and ligated to EcoRI/BamHI digested EMBL3 cos vector. Cloned fragments could be released with SalI digestion.

Isolation of SBEIIa and SBEIIb Gene Sequences from a H. vulgare Genomic Library

Conditions for library screening were hybridisation at 25% formamide, 5×SSC, 0.1% SDS, 10×Denhardts solution, 100 µg/ml salmon sperm DNA at 42° C. for 16 hr, followed by washing with 2×SSC, 0.1% SDS at 65° C. for 3×1 hr (medium stringency). Clones containing the SBEIIa and SBEIIb genes or substantial portions thereof were isolated and sequenced. DNA sequence comparisons to those of the Accession Nos. listed in Table 1 confirmed that both genes of interest had been isolated from barley. SBEIIa and SBEIIb cDNA sequences may also be obtained using reverse transcription-PCR (RT-PCR) with specific primers, a technique well known in the art. Barley SBEIIa and SBEIIb cDNA sequences are shown in FIGS. 1 and 2, and wheat SBEIIa and SBEIIb genomic sequences shown in FIGS. 3 and 4.

when transcribed as part of the RNA in the transformed plant, would be spliced out to form a tight "hairpin" duplex structure. The inclusion of an intron has been found to increase the efficiency of gene silencing conferred by duplex-RNA constructs (Smith et al, 2000). The desired nucleic acid was linked to a high molecular weight glutenin (HMWG) promoter sequence (promoter of the DX5 subunit gene, Accession No. X12928, Anderson et al., 1989) and terminator sequence from the nopaline synthase gene from *Agrobacterium* (nos3').

Duplex-RNA constructs containing SBEIIa or SBEIIb sense/antisense fragments, obtained from wheat SBEIIa and SBEIIb genes in view of the high degree of sequence identity between the wheat and barley genes, were initially generated in the vector pDV03000 and then cut out and ligated to the barley transformation vector pWBVec8. The constructs are shown schematically in FIG. 5. The vector pWBVec8 contains a number of restriction enzyme sites for incorporation of desired DNA sequences.

The SBEIIa duplex-RNA construct contained 1536 bp of nucleotide sequence amplified by PCR from the wheat SBEIIa gene (GenBank Accession number AF338431, see

TABLE 1

Starch branching enzyme genes characterized from cereals

| Species | SBE isoform | Type of clone | Accession No. | Reference |
|---|---|---|---|---|
| Maize | SBE I | cDNA | U17897 | Fisher et al., 1995 |
| | | genomic | AF072724 | Kim et al., 1998a |
| | SBE IIb | cDNA | L08065 | Fisher et al., 1993 |
| | | genomic | AF072725 | Kim et al., 1998 |
| | SBE IIa | cDNA | U65948 | Gao et al., 1997 |
| Wheat | SBE II | cDNA | Y11282 | Nair et al., 1997 |
| | SBE I | cDNA and | AJ237897 SBE I gene) | Baga et al., 1999 |
| | | genomic | AF002821 (SBE I pseudogene) | Rahman et al., 1997, Rahman et al., 1999 |
| | | | AF076680 (SBE I gene) | |
| | | | AF076679 (SBE I cDNA) | |
| | SBE I | cDNA | Y12320 | Repellin et al., 1997 |
| | SBE IIa | cDNA and | AF338432 (cDNA) | Rahman et al., 2001 |
| | | genomic | AF338431 (gene) | |
| Rice | SBE I | cDNA | D10752 | Nakamura and Yamanouchi, 1992 |
| | SBE I | genomic | D10838 | Kawasaki et al., 1993 |
| | SBE3 | cDNA | D16201 | Mizuno et al., 1993 |
| Barley | SBE IIa and SBE IIb | cDNA and genomic | AF064563 (SBE IIb gene) | Sun et al., 1998 |
| | | | AF064561 (SBE IIb cDNA) | |
| | | | AF064562 (SBE IIa gene) | |
| | | | AF064560 (SBE IIa cDNA) | |

Example 3

Constructs for Transformation Experiments to Alter Barley SBEIIA and SBEIIB Expression Duplex-RNA (dsRNA) constructs were made to reduce the expression of either the SBEIIa or SBEIIb genes of barley. In such constructs, the desired nucleic acid sequence corresponding to part of the SBEIIa or SBEIIb genes occurred in both the sense and antisense orientations relative to the promoter so that the expressed RNA comprised complementary regions that were able to basepair and form a duplex or double-stranded RNA. A spacer region between the sense and antisense sequences comprised an intron sequence which, FIG. 3). This included; a 468 bp sequence that comprises the whole of exons 1 and 2 and part of exon 3 (nucleotide positions 1058 to 1336, 1664 to 1761 and 2038 to 2219 in FIG. 3), with EcoRI and KpnI restriction sites on either side (fragment 1), a 512 bp sequence consisting of part of exons 3 and 4 and the whole of intron 3 of SBEIIa (nucleotide positions 2220 to 2731 in FIG. 3) with KpnI and SacI sites on either side (fragment 2) and a 528 bp fragment consisting of the complete exons 1, 2 and 3 of SBEIIa (nucleotide positions 1058 to 1336, 1664 to 1761 and 2038 to 2279 in FIG. 3) with BamHI and SacI sites on either side (fragment 3). Fragments 1, 2 and 3 were then ligated so that the sequence of fragment 3 was ligated to fragment 2 in the antisense orientation relative to fragment 1. The gene construct in the vector pDV03000 was designated pDV03-IIa and the duplex-RNA gene designated ds-SBEIIa.

The strategy for the SBEIIb duplex-RNA construct was similar. The SBEIIb construct contained a fragment of 1607 bp amplified by PCR from the wheat SBEIIb gene (sequence is outlined in FIG. 4). This included; a 471 bp sequence that comprises the whole of exons 1 and 2 and part of exon 3 (nucleotide positions 489 to 640, 789 to 934 and 1598 to 1769 in FIG. 4), with EcoRI and KpnI restriction sites on either side (fragment 1), a 589 bp sequence consisting of part of exons 3 and 4 and the whole of intron 3 of SBEIIb (nucleotide positions 1770 to 2364 in FIG. 4) with KpnI and SacI sites on either side (fragment 2) and a 528 bp fragment consisting of the complete exons 1, 2 and 3 of SBEIIb (nucleotide positions 489 to 640, 789 to 934 and 1598 to 1827 in FIG. 4) with BamHI and SacI sites on either side (fragment 3). Fragments 1, 2 and 3 were then ligated so that the sequence of fragment 3 was ligated to fragment 2 in the antisense orientation relative to fragment 1. The SBEIIb duplex-RNA gene construct in the vector pDV03000 was designated pDV03-IIb and the duplex-RNA gene designated ds-SBEIIb.

The promoter-sense/antisense-terminator cassettes were inserted into the binary vector pWBVec8 using the restriction enzymes ApaI and NotI. The SBEIIa construct in pWBVec8 was designated pVec8-IIa and the SBEIIb construct in pWBVec8 was designated pVec8-IIb. The constructs are shown schematically in FIG. 5.

The identity between the wheat SBEIIa sequences used and the corresponding barley SBEIIa sequence was 93% using the program Gap to compare the sequences. Similarly, the identity between the wheat SBEIIb sequence and the corresponding barley SBEIIb sequence was 92%. Duplex-RNA technology is effective for silencing the expression of genes having sequences with identities over about 85% with respect to the duplex region, and so the expectation was that the duplex constructed with the wheat sequences would be effective against the barley sequences.

Example 4

Transformation of Barley

Methods for the transformation of barley, mediated by *Agrobacterium tumefaciens* or by biolistics, have been described (Tingay et al., 1997; Wan et al, 1994) and can be used to transfer DNA constructs generating transgenic plants. In this example, the gene constructs in binary vectors, made as described above, were introduced into a highly virulent *Agrobacterium* strain by tri-parental conjugation, which was then used to introduce the T-DNA containing the inhibitory gene (ds-SBEIIa or ds-SBEIIb) and the selectable marker gene (encoding hygromycin resistance, expressed from the CaMV35S promoter) into regenerable cells of the scutellum of immature barley embryos, as follows.

Developing barley seeds from the variety Golden Promise, 12-15 days after antithesis, were removed from the growing spike of greenhouse grown plants, and sterilised for ten minutes in 20% (v/v) bleach followed by rinsing once with 95% ethanol and seven times with sterile water. Embryos (approx 1.5 to 2.5 mm in size) were then removed from the seeds under aseptic conditions and the axis cut from each embryo. The embryos were placed cut side down on a petri dish containing callus induction medium. The *Agrobacterium* transconjugants (strain AGL1) were grown in MG/L broth (containing 5 g mannitol, 1 g L-glutamic acid, 0.2 g $KH_2PO_4$, 0.1 g NaCl, 0.1 g $MgSO_4.7H_2O$, 5 g tryptone, 2.5 g yeast extract and 1 µg biotin per litre, pH 7.0) containing spectinomycin (50 mg/l) and rifampicin (20 mg/l) with aeration at 28° C., to a concentration of approximately $2-3\times10^8$ cells/ml, and then approx 300 µl of the cell suspension was added to the embryos in a petri dish. After 2 min, excess liquid was tipped from the plate and the embryos were flipped so that the cut side (axil side of the scutellum) was upwards. The embryos were then transferred to a fresh plate of callus inducing medium and placed in the dark for 2-3 days at 24° C. The embryos were transferred to callus inducing medium with selection (50 µg/ml hygromycin and 150 µg/ml timentin). Embryos remain on this media for 2 weeks in the dark at 24° C. Healthy callus was then divided and placed on fresh selection media and incubated for a further two weeks at 24° C. in the dark. Following this, the embryos were incubated at 24° C. in the light for 2 weeks on regeneration medium containing cytokinin and transferred to rooting media containing cytokinin and auxin for three 2 week periods. Juvenile plants were then transferred to soil mixture and kept on a misting bench for two weeks and finally transferred to a glasshouse. A total of 400 embryos using pVec8-IIb and 300 embryos using pVec8-IIa were treated by this method and 18 plants from 7 calli for the IIb transformation and 18 plants from 14 calli for the IIa transformation survived on selection medium, suggesting that they were successfully transformed with the gene construct. Not all of the plants that were transformed with the selectable marker gene would be expected to integrate the SBEIIa or SBEIIb inhibitory gene; these could readily be distinguished as described in the following examples.

Example 5

Analysis of Barley Plants and Grain Transformed with Duplex-RNA Constructs

The presence or absence of the transgene(s) in barley plants or progeny seed or plants was determined or confirmed by PCR techniques or Southern blot hybridisation analysis. DNA was prepared from leaf samples from putative transformed plants by standard methods.

PCR Analysis of Transformed Barley Plants—Detection of Transgenes.

The forward and reverse primers used for screening the presence of the ds-SBEIIa transgene were BX17 3' (5'-CAA CCA TGT CCT GAA CCT TCA CC-3') SEQ ID No. 5 and AR2akpnR (5'-GGT ACC CCA TCT CCT GGT TTT GGG ACA AC-3') SEQ ID No. 6, respectively. This primer pair amplified a 569 bp product, corresponding to a position within the HMWG promoter sequence of the transgene to the nucleotide position 2219 in FIG. 3, from those plants containing the ds-SBEIIa transgene. The primers used for screening for the presence of the ds-SBEIIb transgene were BX17 3' (as above) and AR2bkpnR (5'-GGT ACC GTC CAT TTC CCG GTG GTG GCA G-3') SEQ ID No. 7. This primer pair amplified a 571 bp product, corresponding to a position within the HMWG promoter to nucleotide position 1768 in FIG. 4, from those lines containing the ds-SBEIIb transgene. PCR amplification was conducted in a 20 µl reaction containing 2.5 units Hotstar Taq, 1× buffer supplied with the enzyme containing 1.5 mM $MgCl_2$, 0.125 mM each deoxynucleotide triphosphate (dNTPs), 1 µM each of the forward and reverse primers and 100 ng DNA. The PCR programme included an initial denaturation step of 95° C. for 5 min, followed by 36 cycles of 95° C. for 30 sec, 59° C. for 1 min and 72° C. for 2 min, finished with 72° C. for 5 min.

Positive barley transformants were identified for both of the SBEIIa and SBEIIb constructs (FIG. 6). The data is summarized in Table 2.

TABLE 2

Summary of PCR and Southern hybridization results of SBEIIa and SBEIIb transgenic lines of barley.

| SBEIIb transgenic line No. | Transform. event no.[a] | PCR | Southern | SBEIIa transgenic line No. | Transform. event no.[a] | PCR | Southern |
|---|---|---|---|---|---|---|---|
| IIb1.1 | 1 | − | − | IIa1.1 | 1 | − | − |
| IIb1.2 | 1 | − | − | IIa2.1 | 2 | − | − |
| IIb1.3 | 1 | + | + (vf) | IIa3.1 | 3 | + | − |
| IIb2.1 | 2 | + | + | IIa3.2 | 3 | + | − |
| IIb2.2 | 2 | + | + | IIa4.1 | 4.1 | + | + |
| IIb3.1 | 3 | + | + | IIa4.2 | 4.2 | + | + |
| IIb4.1 | 4 | + | + | IIa5.1 | 5 | + | nr |
| IIb4.2 | 4 | + | + | IIa5.2 | 5 | + | + |
| IIb4.3 | 4 | + | + | IIa6.1 | 6 | + | + |
| IIb4.4 | 4 | + | + | IIa6.2 | 6 | + | + |
| IIb4.5 | 4 | + | + | IIa7.1 | 7 | − | − |
| IIb4.6 | 4 | − | + | IIa9.1 | 9 | + | nr |
| IIb5.1 | 5 | + | + (f) | IIa10.1 | 10 | + | nr |
| IIb8.1 | 8 | + | − | IIa11.1 | 11 | − | − |
| IIb8.3 | 8 | + | − | IIa13.2 | 13 | + | nr |
| IIb8.4 | 8 | + | + (f) | IIa13.3 | 13 | + | nr |
| IIb9.1 | 9 | + | + | IIa15.1 | 15 | + | nr |
|  |  |  |  | IIa16.1 | 16 | − | − |

[a]Transformation event Nos. with the same number were isolated from the same callus and may be identical or independent. Different numbers: independent transformants.
(f): faint;
(vf): very faint;
nr: no result Southern Blot Hybridization Analysis of Transformed Barley.

Figure 7:
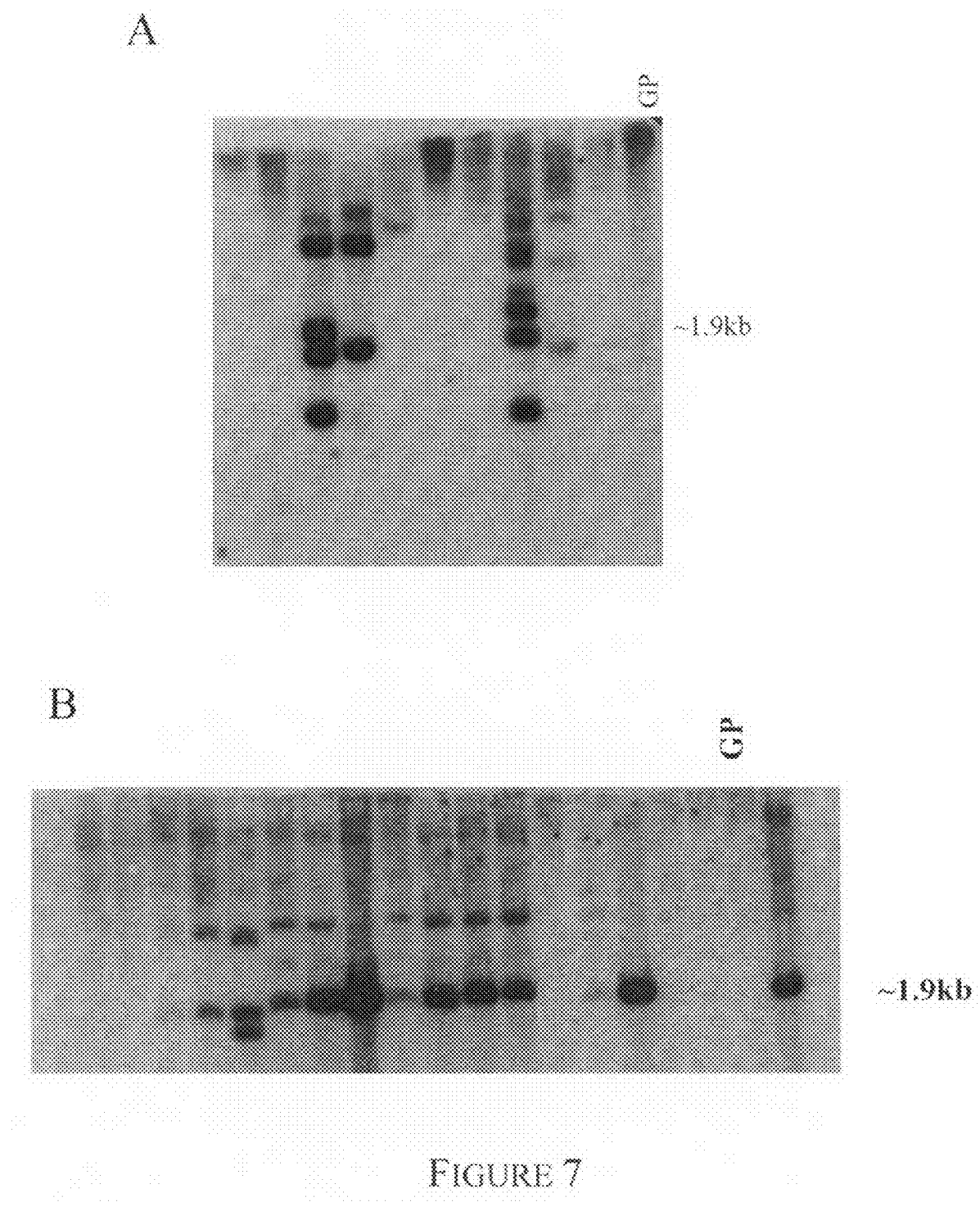
FIG. 7. Southern blot analysis of ds-SBEIIa and ds-SBEIIb transgenic lines of barley. A. Barley ds-SBEIIa positive transgenes as shown by Southern blot hybridization. The expected band size is 1836 bp. B. Barley ds-SBEIIb positive transgenes as shown by Southern. The expected band size is 1907 bp. GP is Golden Promise (negative control).

Southern blot hybridization analysis was carried out on DNA from the ds-SBEIIa and ds-SBEIIb transgenic plants and their progeny to confirm the PCR results. EcoRI digested DNA, prepared from the plants by standard methods, was electrophoresed on 1% agarose gels and blotted on to Hybond N+ nylon membrane (Amersham). Radio-labelled probes were generated from the intron 3 region of the SBEIIa (positions 2220 to 2731 see FIG. 3) and SBEIIb (positions 2019 to 2391 see FIG. 4) genes. These segments are part of the respective ds-SBEIIa and ds-SBEIIb constructs (Example 3) and were radioactively labeled using the Megaprime DNA labeling system (Amersham Pharmacia Biotech UK Ltd) and used for hybridization. The hybridization was carried out in 25% (v/v) formamide, 5×SSC, 0.1% SDS, 10×Denhardt's solution, 100 µg/ml salmon sperm DNA at 42° C. for 16 hr followed by washing in 2×SSC, 0.1% SDS at 65° C. for 3×1 hr. Autoradiography of the membranes revealed positive hybridizing bands in lanes corresponding to plants that were positive for the constructs (FIG. 7). The endogenous barley SBEIIa and SBEIIb gene fragments were not detected in the hybridization because of sequence divergence with the wheat intron 3 probe used.

The results of the PCR and Southern hybridization analyses are summarized in Table 2. In general, the PCR and Southern hybridization results correlated well. Discrepancies may have been due to false negatives and would readily be resolved by repeated assays. Plants that were positive for the transgenes as demonstrated by both methods included 4 independent transformation events for ds-SBEIIa Southern (IIa 4.1, IIa 4.2, IIa 5 and IIa 6) and 5 independent events for ds-SBEIIb (Event no. IIb 2, IIb3, IIb4, IIb5 and IIb 9).
Analysis of Barley Endosperm Proteins by Polyacrylamide Gel Electrophoresis (PAGE).

To determine the effect of the ds-SBEIIa and ds-SBEIIb transgenes on the barley SBEIIa and SBEIIb gene expression in the transformed plants, specific protein expression in endosperm tissue of developing grains was detected by non-denaturing PAGE and Western blot analysis. Since the T1 seeds (seeds from T0 plants) were expected to be segregating for the transgenes, endosperm from each of ten individual developing T1 grains from each T0 plant, at 20 days after flowering, were analyzed for SBEIIa and SBEIIb protein expression. To preserve the T1 plants, embryos were rescued from the developing grains and cultured to regenerate the T1 plants. Endosperm dissected away from all maternal tissues (0.2 g) was homogenized in 600 µl of 50 mM KPi buffer (42 mM $K_2HPO_4$ and 8 mM $KH_2PO_4$), pH 7.5 containing 5 mM EDTA, 20% glycerol, 5 mM DTT and 1 mM Pefabloc. The ground samples were centrifuged for 10 min at 13,000 g and the supernatant aliquoted and frozen at −80° C. until use. Protein levels were measured with Coomassie reagent with BSA as a standard. Total soluble proteins, equivalent to 20 µg, extracted from each endosperm, were loaded per lane and electrophoresed in 8% non-denaturing polyacrylamide gels containing 0.34 M Tris-HCl (pH 8.8), acrylamide (8.0%), ammonium persulphate (0.06%) and TEMED (0.1%). Following electrophoresis, the proteins were transferred to a nitrocellulose membrane according to Morell et al., (1997) and immunoreacted with SBEIIa or SBEIIb specific antibodies. The antibody used for detection of SBEIIa was 3KLH, from rabbits, which had been raised against the synthetic peptide AASPGKVLVPDESDDLGC SEQ ID No. 8 (the sequence from the N-terminus of SBEIIa), and was diluted 1:5000 for use. The antibody used for detection of SBEIIb was R6, raised against the synthetic peptide AGGPSGEV-MIGC SEQ ID No. 9 (the deduced sequence from the N-terminus of SBEIIb) and diluted 1:6000 before use. The secondary antibody used was GAR-HRP conjugate (1:3000 dilution), and immunoreactive bands were revealed using an Amersham ECL-detection system.

Figure 8:
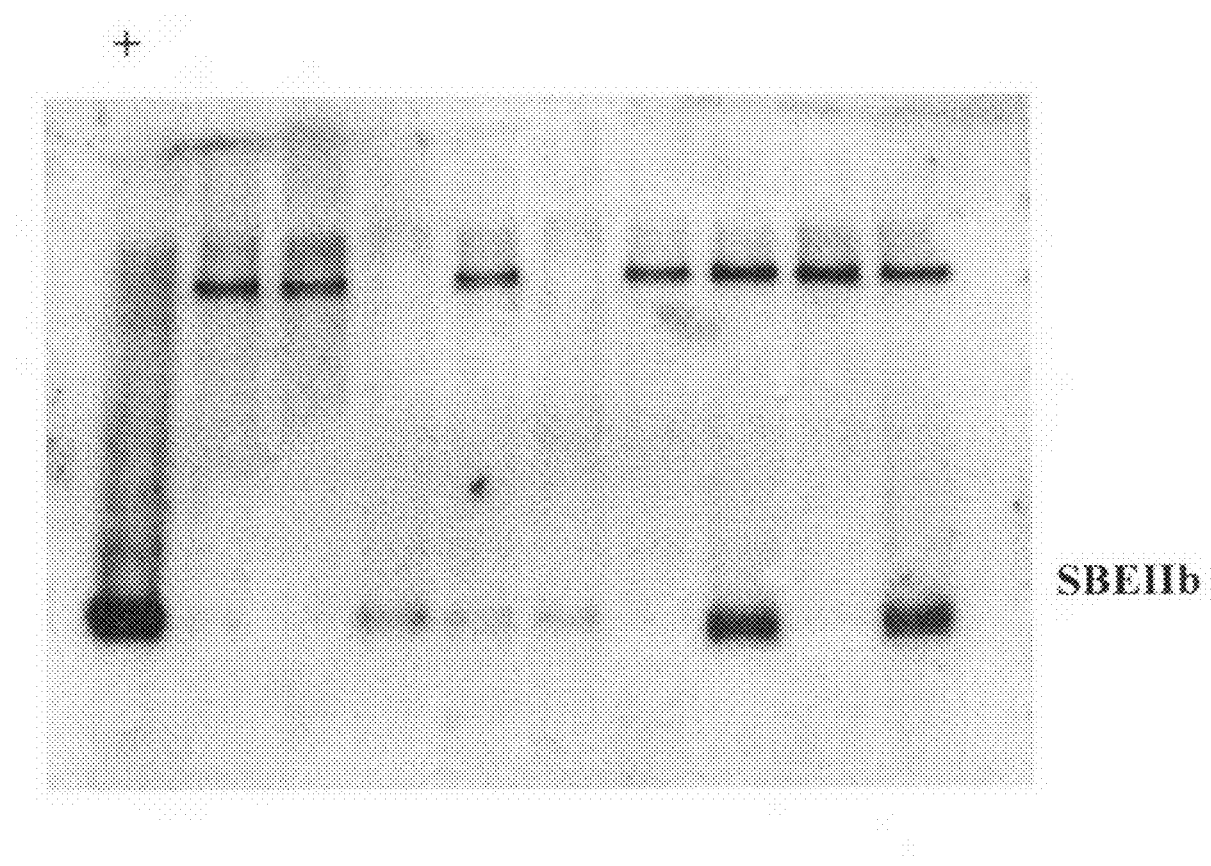
FIG. 8. Western blot analysis of ds-SBEIIa and ds-SBEIIb transgenic lines of barley. Ten T1 seeds (seeds from T0 plants) of lines IIb 4.3 and IIb4.4 were analyzed for SBEIIb expression by Western blot analysis using non-denaturing PAGE and an SBEIIb specific antibody. Lane 1 (+) is for the positive control, variety Glacier.
Figure 9:
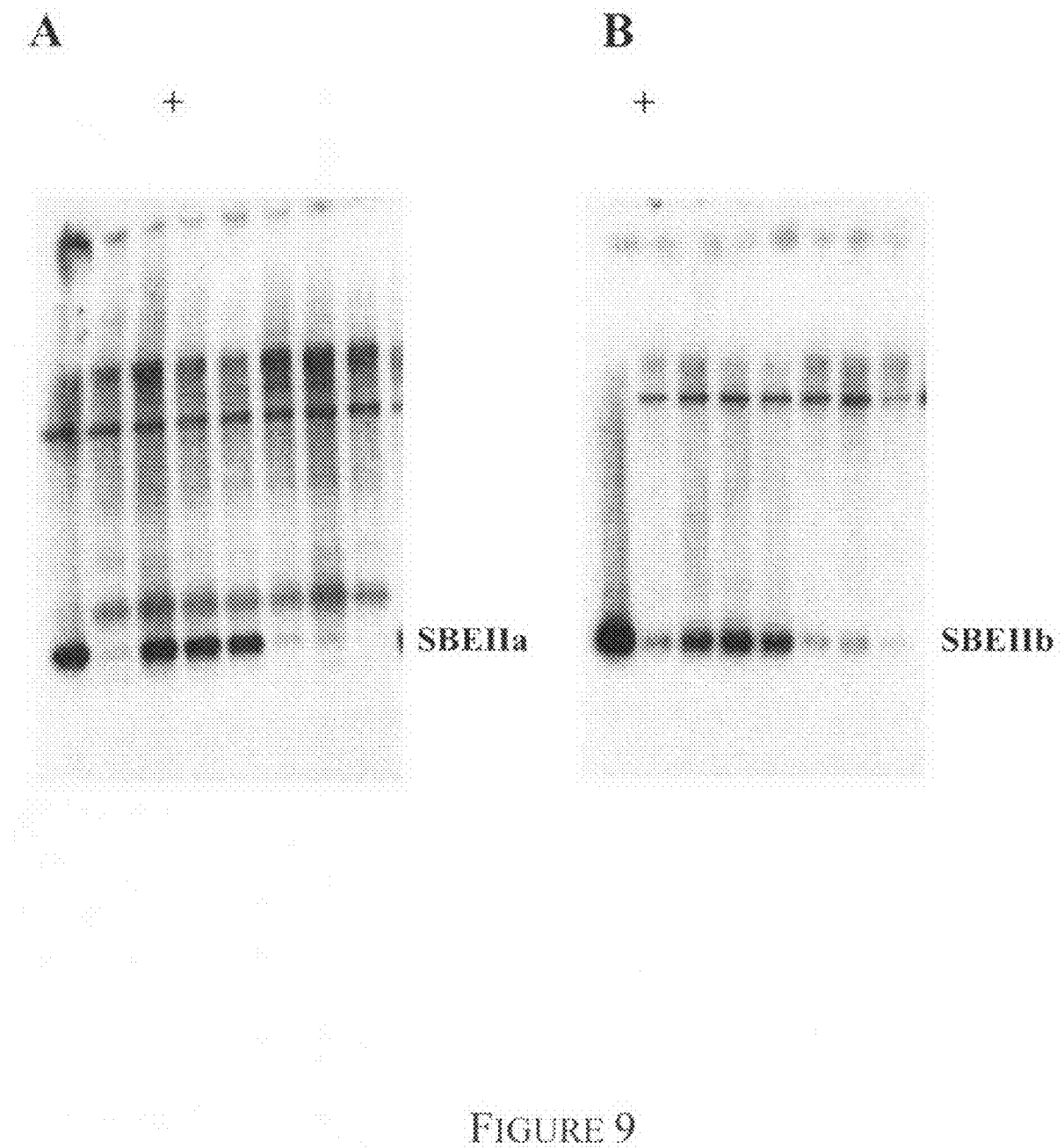
FIG. 9. Western blot analysis of ds-SBEIIa and ds-SBEIIb transgenic lines of barley. T1 seeds (seeds from T0 plants) of line IIa 4.1 were analyzed for A. SBEIIa or B. SBEIIb expression by Western blot analysis using non-denaturing PAGE and SBEIIa or SBEIIb specific antibodies. The lanes on both the gels represent the same seeds. Lane 1 (+) in each panel is for the positive control, variety Glacier.

The protein expression in the developing T1 seeds from plants transformed with the ds-SBEIIa or ds-SBEIIb genes appeared to be segregating in a 1:2:1 ratio of strong bands: moderate-weak bands:no bands for some of the transformed lines (for example, see FIGS. 8 and 9). This ratio corresponds to the expected segregation ratio of homozygotes (wild type=null for transgene): heterozygotes: homozygous for the transgene. The T1 plants from the rescued embryos are grown to produce T2 seed which are screened by PCR and protein expression analysis to confirm the genetic status of the T1 seed with respect to the transgene.

These data indicate that the duplex-RNA constructs are effective in reducing the expression of the SBEIIa and SBEIIb genes in endosperm of barley.

Figure 10:
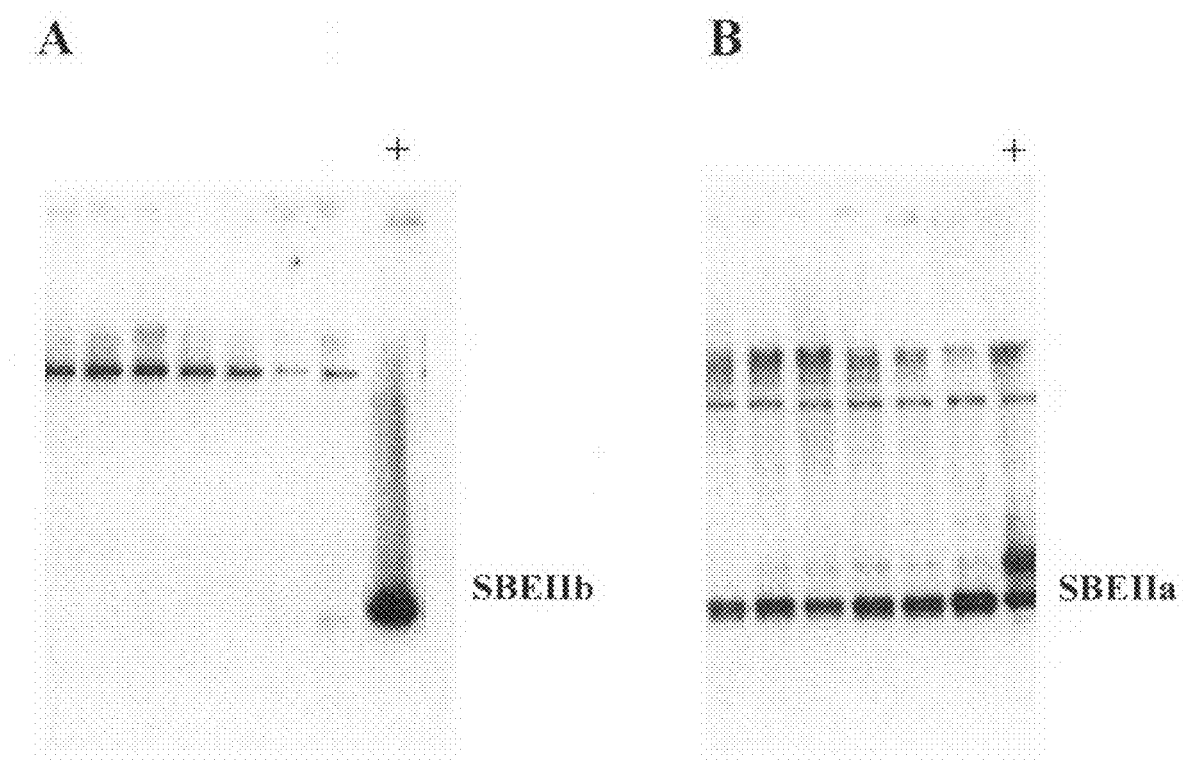
FIG. 10 Western blot analysis of ds-SBEIIa and ds-SBEIIb transgenic lines of barley. T1 seeds (seeds from T0 plants) of line IIb 4.1 were analyzed for A. SBEIIb or B. SBEIIa expression by Western blot analysis using non-denaturing PAGE and SBEIIb or SBEIIa specific antibodies. The lanes on both the gels represent the same seeds. The last lane (+) in each panel is for the positive control, variety Glacier.

The expression of the SBEIIb gene in transgenic seeds containing the ds-SBEIIa transgene, and the expression of the SBEIIa gene in seeds containing the ds-SBEIIb were also analyzed by the Western blot method. Unexpectedly, transgenic seeds comprising ds-SBEIIa, for example from the transformation event IIa 4.1, were much reduced for SBEIIb. See FIG. 9 which shows only a low level of expression of SBEIIb in seeds from line IIa 4.1.8 (note the very weak bands in 4 of the 7 lanes). This line contained the ds-SBEIIa transgene and had negligible SBEIIa expression. However, the converse effect was not observed in seeds transgenic for ds-SBEIIb. The SBEIIa expression was unaltered in the seeds in which SBEIIb was completely silenced by ds-SBEIIb (FIG. 10) namely, for transgenic lines from the transformation events IIb 4 and IIb 2. The region including exons 1-3 was used for both ds-SBEIIa and ds-SBEIIb duplex constructs. Alignment of the sequences of SBEIIa and SBEIIb in this region revealed only ~70% identity. The longest stretch of 100% identity was a region of 21 bp in the exon 2. Although it is still possible that expression of SBEIIb was suppressed by the ds-SBEIIa construct due to sequence homology, it is also possible that the activity of SBEIIb was reduced by the ds-SBEIIa transgene by some other mechanism.

The expression levels of the SBEIIa and SBEIIb genes can also be specifically determined at the mRNA levels through standard techniques such as Northern hybridisation or RT-PCR methods, for example by using probes from non conserved regions or primer pairs which hybridize to unique sites in one of the genes but not the other, for example in the 3' untranslated regions. Such regions or sites can readily be identified by comparison of the two gene sequences.

Example 6

Analysis of Grain Composition and Content, Including Starch

The grain composition and content, particularly for starch, may be measured using standard techniques such as those described in Example 1.

Figure 11:
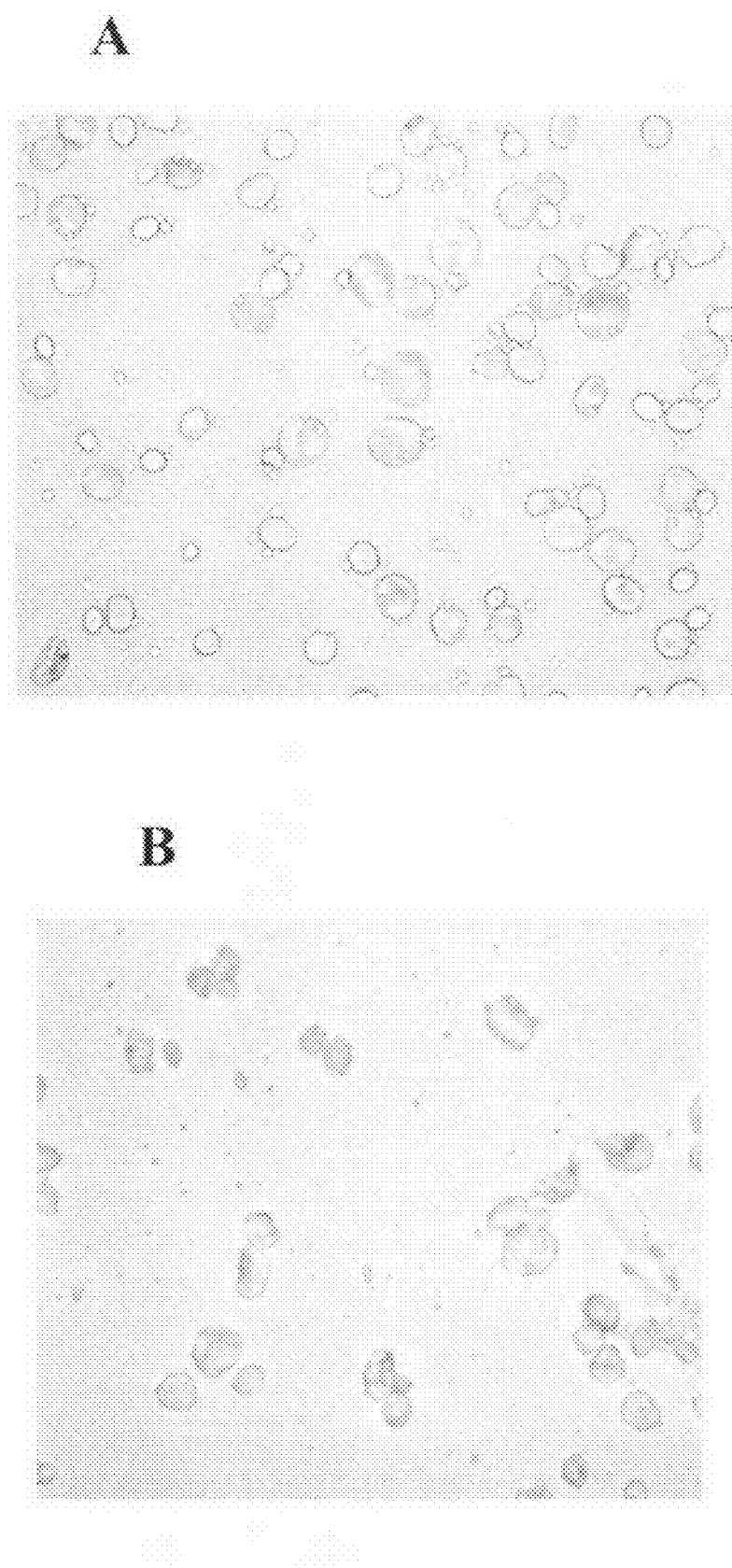
FIG. 11. Starch granule morphology of ds-SBEIIa transgenic barley. Starch granules from single seeds were visualized through light microscopy for both ds-SBEIIa and ds-SBEIIb transgenic seeds.
Figure 12:
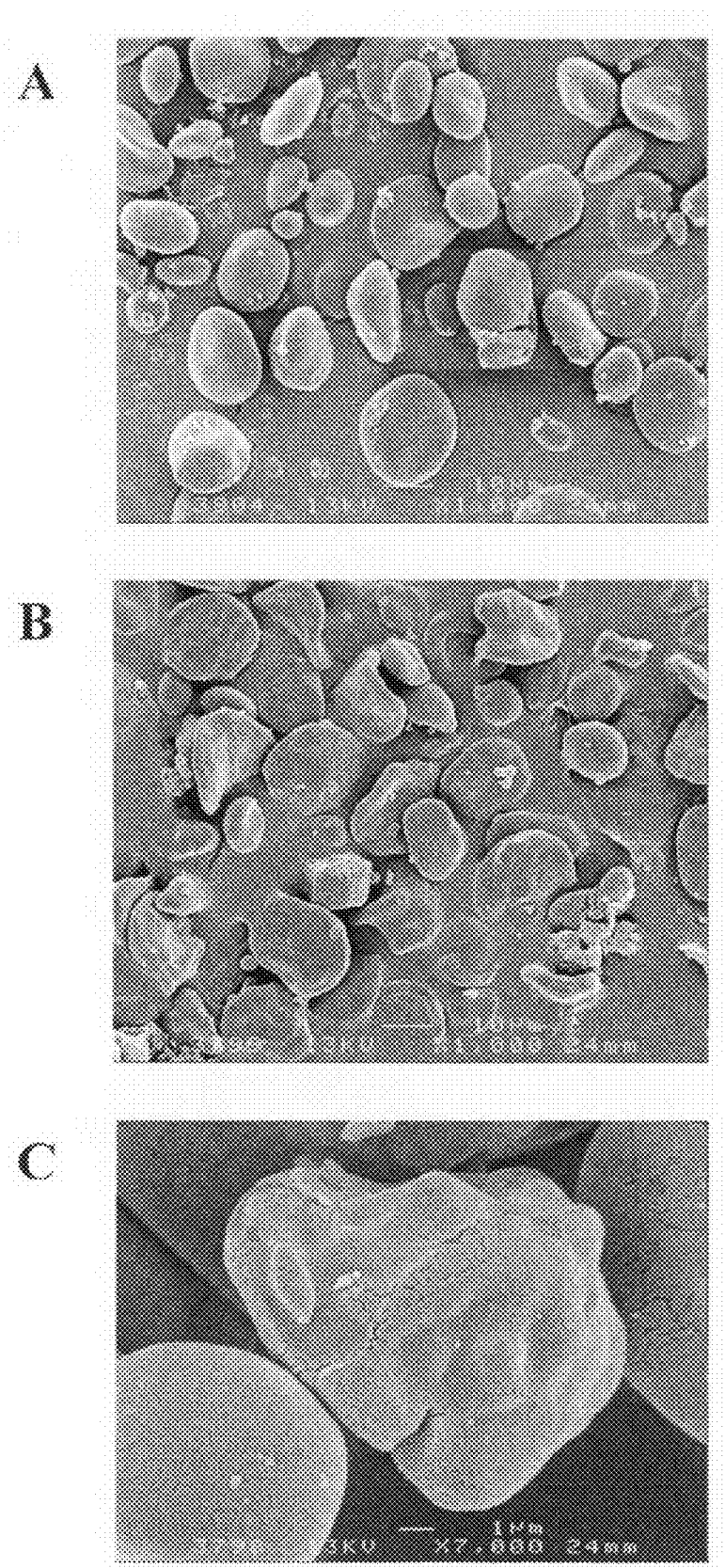
FIG. 12. Scanning electron microscopy (SEM) of starch granules. A. wild-type starch granules (line IIa 4.2.3), B. and C. from a ds-SBEIIa transgenic endosperm (line IIa 4.2.5). Starch granules from ds-SBEIIb (SBEIIb inactivated) seed did not appear to be morphologically altered compared to wild-type

After extraction of the soluble proteins as described above, the starch granules from individual endosperm samples from developing seeds containing the ds-SBEIIa transgene were visualized under a light microscope. A significant alteration in starch granule morphology was observed (see for Example FIG. 11) in developing endosperm that were reduced in SBEIIa expression for three of the five transformation events examined: IIa 4.1, IIa 4.2 and IIa 13, but not for events IIa 5 or IIa 6 which may have had a lesser degree of gene inactivation. For example, starch from IIa 4.2.5 seeds, which had no SBEIIa band in the protein immunoblot, was highly distorted compared to the normal granules in IIa 4.2.3 seeds, which had a strong SBEIIa band in the protein immunoblot (Table 3). Light microscopy results were confirmed by scanning electron microscopy (SEM), which may also be used to view starch granules directly. To do this, purified starch was sputtered with gold and scanned at 15 kV at room temperature. Seeds reduced for SBEIIa expression showed a distorted irregular shape that was visible under the scanning electron microscope, for example the distortion of granules in IIa 4.2.5 seeds compared to IIa 4.2.3 seeds (FIG. 12).

In contrast to the plants containing ds-SBEIIa, the plants transformed with ds-SBEIIb showed endosperm starch granules with normal morphology when examined by microscopy, for example line IIb 4.1 (see Table 3). This suggests that reduction of SBEIIb expression alone did not substantially alter starch granule morphology.

TABLE 3

Starch granule morphology of T1 endosperm tissues of barley ds-SBEIIa and ds-SBEIIb transgenic lines

| No | Transgenic line | Protein band on immunoblot | Starch granule morphology (light microscopy) |
|---|---|---|---|
| 1 | IIa 4.1.8 | No band | Distorted |
| 2 | IIa 4.1.4 | Strong band | normal |
| 3 | IIa 4.1.3 | Strong band | normal |
| 4 | IIa 4.2.1 | No band | Distorted |
| 5 | IIa 4.2.9 | No band | distorted |
| 6 | IIa 4.2.5 | No band | distorted |
| 7 | IIa 6.2.8 | No band | normal |
| 8 | IIa 5.2.3 | No band | normal |
| 9 | IIa 6.2.2 | Strong band | normal |
| 10 | IIa 4.2.3 | Strong band | normal |
| 11 | IIa 13.1.9 | No band | normal |
| 12 | IIa 13.1.10 | Weak band | normal |
| 13 | IIa 13.1.3 | Strong band | normal |
| 14 | IIa 13.2.4 | No band | Some distortion |
| 15 | IIa 13.1.6 | Weak band | normal |
| 16 | IIb 4.1.9 | No band | normal |
| 17 | IIb 4.1.8 | No band | normal |
| 18 | IIb 4.1.2 | No band | normal |

Birefringence is the ability of a substance to refract light in two directions; this produces a dark cross called a "maltese cross" on each starch granule when viewed with a polarizing microscope. Birefringence is an indicator of the degree of ordered structural organization of the polymers within the granules (Thomas and Atwell, 1999). Starch granules from endosperm of IIa 4.2.5 seeds (reduced for SBEIIa activity) under polarized light indicated that there is a significant loss of birefringence in these granules compared to that from IIa 4.2.3 seeds (wild type) On average, 44.8% of the granules in IIa 4.2.5 seeds were without birefringence in contrast to 2.2% in IIa 4.2.3 seeds (Table 4). Loss of birefringence in starch granules is generally well correlated with increased amylose content.

TABLE 4

Birefringence of starch granules from T1 endosperm of ds-SBEIIa barley transgenic lines

| Line | Microscopic field | No. of granules showing no BF | No. of granules showing partial BF | No. of granules showing full BF |
|---|---|---|---|---|
| A4.2.5 (SBEIIa negative) | 1 | 38 | 19 | 12 |
| | 2 | 48 | 22 | 9 |
| | 2 | 26 | 25 | 35 |
| | 4 | 17 | 12 | 25 |
| Total | | 129 (44.8%) | 78 (27.1%) | 81 28.1%) |
| A4.2.3 | 1 | 5 | 8 | 205 |

TABLE 4-continued

Birefringence of starch granules from T1 endosperm of ds-SBEIIa barley transgenic lines

| Line | Microscopic field | No. of granules showing no BF | No. of granules showing partial BF | No. of granules showing full BF |
|---|---|---|---|---|
| (control) | 2 | 3 | 9 | 104 |
| | 3 | 3 | 5 | 200 |
| | 4 | 2 | 2 | 85 |
| Total | | 13 (2.1%) | 24 (3.8%) | 593 (94.1%) |

BF: Birefringence

Grain weight analysis of transgenic seeds, from plants grown in the greenhouse, from the line IIa 4.2 containing ds-SBEIIa, revealed that there was no significant reduction in grain weight and therefore starch production, even in the seeds with highly distorted starch granules (Table 5). This is in contrast to the reduced grain weight observed in barley that is mutant in the SSIIa gene, which shows significantly reduced starch production (Morell et al, 2003). This suggests that the average grain weight and therefore the yield of field-grown barley with reduced SBEIIa activity in the endosperm is about normal.

TABLE 5

Grain weight of T1 seeds from the SBE IIa barley transgenic line IIa 4.2

| No. | Seed from line No.: | Starch granule morphology | Grain weight (mg) |
|---|---|---|---|
| 1 | IIa 4.2.1 | Normal | 46.4 |
| 2 | IIa 4.2.2 | Highly distorted | 39.3 |
| 3 | IIa 4.2.3 | Distorted | 39.0 |
| 4 | IIa 4.2.4 | Distorted | 40.8 |
| 5 | IIa 4.2.5 | Highly distorted | 37.3 |
| 6 | IIa 4.2.6 | Normal | 41.8 |
| 7 | IIa 4.2.7 | Normal | 35.0 |
| 8 | IIa 4.2.8 | Highly distorted | 41.5 |
| 9 | IIa 4.2.9 | Highly distorted | 41.1 |
| 10 | IIa 4.2.10 | Highly distorted | 38.6 |

Amylose and Amylopectin Levels in Transgenic Barley Grain.

Seed with starch granules having a distorted shape have been reported in high amylose barley (Morell et al, 2003) and in low amylopectin (LAPS) maize having about 90% amylose in starch (Sidebottom et al., 1998). Amylose content may be determined by size exclusion HPLC in 90% (w/v) DMSO, or by iodine blue value (iodometric method), as described in Example 1. From the grain weight and amylose content, the amount of amylose deposited per grain can be calculated and compared for transgenic and control lines.

Starch was isolated from barley grains of the T1 generation, segregating for ds-SBEIIa, or the T2 generation (probably homozygous for ds-SBEIIa) from plants transgenic for the ds-SBEIIa gene, or resulting from a cross between line IIa 4.2.5 and line IIb 4.3.8 (containing both ds-SBEIIa and ds-SBEIIb), and the amylose contents determined by the colorimetric method of Morrison and Laignelet (1983). The amylose content of starch from five pooled grain samples, listed below, was determined. The absorbance read at 650 nm was converted to percentage amylose content using the regression equation derived from standard samples (ranging from 0 to 100% amylose) made from potato amylose and amylopectin, $Y=137.38x-30.361$, where x is the absorbance at 650 nm and Y is the percentage amylose content.

Samples:
Pool 1: seven T1 seeds that showed severe starch granule distortion from the transgenic line IIa 4.1
Pool 2: six T1 seeds that showed some granule distortion from the transgenic line IIa 4.1
Pool 3: seven T1 seeds that had normal looking granules from the transgenic line IIa 4.1
Pool 4: six T2 seeds that showed severe granule distortion from the transgenic line IIa 4.2.5
Pool 5: five F1 seeds that showed severe starch granule distortion from the cross between IIa 4.2.5 and IIb 4.3.8 (ds-SBEIIb transgenic line).
Controls: Barley SSIIa mutant M292 (Morel et al., 2003), barley cv Himalaya and SSIIa wheat mutant (Yamamori et al. 2000).

Starch from grains from barley with reduced SBEIIa activity, based on the distorted starch granules, showed more than 80% amylose. The amylose content increased with the degree of distortion of the starch granules, compare pools 1, 2 and 3 (Table 6). The amylose contents for pools 1 and 2 were higher than for starch from the SSIIa mutant barley line M292 (Table 6). The amylose content was even higher (>90%) in the pool 5 consisting of F1 grains from the cross between the ds-SBEIIa and ds-SBEIIb transgenic lines. It is noted that the absorbance values obtained by this method may be influenced slightly by the structure of amylopectin.

TABLE 6

Amylose content in the grain of transgenic barley lines reduced for SBEIIa activity.

| | Amylose content (% of starch) | | | |
|---|---|---|---|---|
| Starch sample | Replication 1 | Replication 2 | Replication 3 | Mean |
| Pool 1 | 85.0 | 80.2 | 80.2 | 81.8 |
| Pool 2 | 60.6 | 52.1 | 51.7 | 54.8 |
| Pool 3 | 39.4 | 40.5 | 40.0 | 40.0 |
| Pool 4 | 84.4 | 84.6 | 88.3 | 85.8 |
| Pool 5 | 95.3 | 94.8 | 106.1 | 98.7 |
| M292 barley | 66.9 | 60.5 | 58.4 | 61.9 |
| Himalaya barley | 21.8 | 21.6 | 22.3 | 21.9 |
| SSIIa wheat mutant | 52.1 | 46.7 | 54.5 | 51.1 |

This implies that the amylopectin content in the starch of these grains is considerably reduced, from about 75% in wild-type to less than 20% or even less than 10%, since cereal starch is made up almost entirely of amylose and amylopectin.

Example 7

Mutation of SBEIIA Gene in Barley

Mutation of the SBEIIa gene in barley leading to non expression of SBEIIa can be achieved through either gamma ray irradiation or chemical mutagenesis, for example with ethyl methane sulfonate (EMS). For gamma ray induced mutation, seeds are irradiated at a dose of 20-50 kR from a $^{60}$Co source (Zikiryaeva and Kasimov, 1972). EMS mutagenesis is performed by treating the seeds with EMS (0.03%, v/v) as per Mullins et al., (1999). Mutant grains are identified on the basis of increased amylose content or altered starch grain morphology and confirmed by the methods described above. Mutants in SBEIIa can be re-mutagenized in a second round and the progeny screened for loss of SBEIIb activity in addition to SBEIIa, or the SBEIIa mutant can be crossed with an SBEIIb mutant to combine the mutations and produce a non-transgenic variety of barley substantially lacking SBEII activity in the endosperm.

Example 8

Cloning of the SBEI Gene and Constructs for Inhibition of SBEI Expression in Barley Isolation of the SBEI gene is achieved by hybridization of probes to the barley cDNA or genomic library or by PCR methods. The PCR primer design may be based on the homologous genes from wheat, for example, based on the DNA sequence set forth in Genbank AF076679. The primers used might be 5' ACGAAGATGCTCTGCCTCAC 3' SEQ ID No. 10 and 5' GTCCAACATCATAGCCATTT 3' SEQ ID No 11 which should result in a PCR product of about 1015 bp.

The SBEI gene sequences are used to construct inhibitory gene constructs in a similar fashion to those described above for SBEIIa and SBEIIb, and introduced into barley.

Example 9

Combination of SBEIIA Mutants with Other Starch Synthesis Mutants

Plants transgenic for ds-SBEIIa and reduced for SBEIIa activity were crossed with the barley lines M292 (SSIIa mutant) and High Amylose Glacier (HAG). The following crosses were established:

1) line IIa 4.1.10×HAG 2) line IIa 4.1.16×HAG 3) line IIa 4.1.20×M292

4) line IIa 4.1.19×HAG

The F1 plants are self-fertilized and lines homozygous for both mutations are identified by genetic and molecular analysis. Combining the ds-SBEIIa transgene with the SSIIa mutation is expected to yield starches with very high amylose content together with high β-glucan content. Combining the ds-SBEIIa transgene with the HAG mutation may yield further alteration in starch composition with improved functionality in addition to high amylose content.

Example 10

Characteristics of Field-Grown Barley

Kernel weights and β-glucan contents were measured for several field-grown varieties of barley including the M292 and M342 lines (ssIIa mutant, approx 60-65% amylose). It is noted from the results (Table 7) that M292 and M342 grain were reduced in kernel size and increased in β-glucan content relative to the wild-type varieties (3.0-6.0% β-glucan). The average weight of field-grown wild-type grain was in the range 35-45 g/1000 kernels, grown under these conditions. The β-glucan content in the grain of wild-type varieties was in the range 3-6%.

TABLE 7

Kernel weight and β-glucan levels in field-grown barley.

| Cultivar | 1000 kernel weight [a] (g) | % beta-glucan [a] |
|---|---|---|
| Tantangera | 34.90, 35.40 | 3.01, 3.37 |
| Sloop | 37.90, 41.90 | 3.04, 2.54 |
| Waxiro | 36.60, 37.10 | 5.14, 6.86 |
| Schooner | 42.60, 38.60 | 3.85, 3.73 |
| Gairdner | 44.80, 37.10 | 4.61, 4.19 |
| Namoi | 40.80, 40.80 | 5.19, 4.34 |
| Himalaya | 39.60, 37.90 | 6.04, 5.50 |
| M292 | 25.10, 28.70 | 10.01, 9.53 |
| M342 | 28.90, 30.30 | 8.02, 8.65 |
| Tantangera × M292 DH | 21.20, 20.40 | 9.08, 10.95 |

[a] Duplicate values are given, for separate plots in the field.

It will be apparent to those skilled in the art that various modifications and alterations to these methods may be made without departing from the scope of the invention.

REFERENCES

Abel et al., (1996). *The Plant Journal* 10, 981-991.
Anderson et al., (1989). *Nucl Acids Res* 17, 461-462.
Batey and Curtin. (1997). *Starch* 48, 338-344.
Batey et al., (1997). *Cereal Chemistry* 74, 497-501.
Biyashev et al., (1986). *Soviet Genetics* 22, 296-303.
Blauth et al., (2001). *Plant Physiology* 125, 1396-1405.
Bourque. (1995). *Plant Science* 105, 125-149.
Boyer and Preiss, (1978). *Carbohydrate Research* 61, 321-334.
Boyer and Preiss, (1981). *Plant Physiology* 67, 1141-1145.
Boye et al., (1980). *Starch* 32, 217-222.
Buleon et al., (1998). *International Journal of Biological Macromolecules* 23, 85-112.
Campbell et al., (1994). *Cereal Chemistry* 71, 464-468.
Cao et al., (2000). *Archives. of Biochemistry and Biophysics.* 373, 135-146.
Case et al., (1998). *Journal of Cereal Science* 27, 301-314.
Castillo, et al., (1994). *Bio/technology* 12, 1366-1371.
Cheetham and Tao, (1997). *Carbohydrate Polymers* 33, 251-261.
Cho, et al. (1999). *Plant Science* (Limerick) 148, 9-17.
Craig et al., (1998). *Plant Cell* 10, 413-426.
Denyer et al., (1996). *Plant Physiology* 112, 779-785.
Dunn et al., (1953) *Agronomic Journal* 45: 101
Eslick and Ries, (1976). *Barley Genetics Newsletter* 6, 21-22.
Fedak et al., (1972). *Canadian Journal of Genetics and Cytology* 14, 949-957.
Fenech et al., (1999) *J Nutr* 129, 1114-1119.
Filpse et al., (1996). *Planta* 198, 340.
Fontaine et al., (1993). *Journal of Biological Chemistry* 268, 16223-16230.
Fujita et al., (1999) *Breeding. Science* 49, 217-219.
Fuwa et al., (1999). *Starch/Starke.* 51, 147-151.
Gao et al., (1998). *Plant Cell* 10, 399-412.
Giroux and Hannah. (1994). *Molecular and General Genetics* 243, 400-408.
Gless, et al. (1998). *Journal of Plant Physiology* 152, 151-157.
Goering and DeHaas, (1974). *Cereal Chemistry* 51, 573-578.
Green et al., (1997). *Plant Physiology* 114, 203-212.
Gubler et al., (2000) *Plant Physiology* 122, 1457.
Hedman and Boyer, (1982). *Biochemical Genetics* 20, 483-492.
Ikawa et al., 1981 *Starch/Starke* 33 9-13.
James et al., (1995). *Plant Cell* 7, 417-429.

Jane et al., (1999). *Cereal Chemistry* 76, 629-637.
Jarvi and Eslick, R. F. (1975). *Crop Science* 15, 363-366.
Jobling et al., (1999). *Plant Journal* 18, 163-171.
Katz et al., (1993). *Carbohydrate polymers* 21, 133-136.
Knight et al., (1998). *Plant Journal* 14, 613-622.
Konik-Rose et al (2001) *Starch* 53, 14-20.
Krueger et al., (1987). *Cereal Chemistry* 64, 187-190.
Kubo et al., (1999). *Plant physiology.* 121, 399-409.
Li et al., (1999). *Plant physiology.* 120, 1147-1155.
Li, et al., (2000). *Plant Physiology* 123, 613-624.
Li et al., (1999). *Theoretical and Applied Genetics* 98, 1208-1216.
Maniatis et al., 1982 Molecular cloning: a laboratory manual Cold Spring Harbour Laboratory Press New York.
Mizuno et al., (1993). *Journal of Biological Chemistry* 268, 19084-19091.
Mizuno et al., (1992). *Journal of Biochemistry* 112, 643-651.
Morell et al., (1997). *Plant Physiology* 113, 201-208.
Morell et al., (1998). *Electrophoresis* 19, 2603-2611.
Morrison and Laignelet (1983). *Journal of Cereal Science* 1:9-20.
Mouille et al., (1996). *The Plant Cell.* 8, 1353-1366.
Mullins et al., (1999). *European Journal of Plant Pathology* 105: 465-475.
Myers et al., (2000). *Plant Physiology* 122, 989-997.
Nakamura. (2002). *Plant Cell Physiology* 43, 718-725.
Netsvetaev, (1990). *Nauchno-Tekh. Bull' VSGI, Odessa.* No. 1 75, 31-35.
Netsvetaev, (1992). *Cytology and Genetics (Kiev)* 26, 26-30.
Netsvetaev and Krestinkov. (1993). *Barley Genetics Newsletter* 22, 44-45.
Nishi et al., (2001). *Plant Physiology* 127, 459-472.
Ng et al., (1997). *Cereal Chemistry.* 74, 288-288.
Pena, et al., (1987). *Nature, UK* 325, 274-276.
Rahman et al., (1995). *Australian Journal of Plant Physiology* 22, 793-803.
Ramage and Eslick, (1975). *Barley Genetics Newsletter* 5, 114.
Ramage and Eslick, (1975). *Barley Genetics Newsletter* 6, 115.
Safford et al., (1998). *Carbohydrate Polymers* 35, 155-168.
Sakata and Engelhard, (1983). *Comp. Biochem Physiol.* 74a, 459-462.
Schulman and Kammiovirta, (1991). *Starch* 43, 387-389.
Schwall et al., (2000). *Nature Biotechnology* 18, 551-554.
Senior (1998). *Biotechnology and Genetic Engineering Reviews* 15, 79-119.
Shannon and Garwood, (1984). In *Starch: Chemistry and Technology*, Whistler et al., eds, Academic Press, Orlando, Fla., pp 25-86.
Shure et al., (1983). *Cell* 35, 225-233.
Sidebottom et al., (1998). *Journal of Cereal Science* 27, 279-287.
Somers et al., (1992). *Bio/technology* 10, 1589-1594.
Somers, et al. (1994). *Genetic engineering of oat.* 37-46.
Sun et al., (1997). *The New Phytologist* 137, 215-215.
Sundberg et al., (1998). Journal of the Science of Food and Agriculture. 76, 457-463.
Takeda et al., (1993a). *Carbohydrate Research* 240, 253-262.
Takeda et al., (1993b). *Carbohydrate Research* 246, 273-281.
Thomas and Atwell 1999 Starches Eagen Press, St Paul, Minn., USA pp: 13-24.
Thorbjornsen et al., (1996). *Plant Journal* 10, 243-250.
Tingay, et al., (1997). *Plant Journal* 11, 1369-1376.
Topping, (1999). *Asia Pacific Journal of Clinical Nutrition* 8, S22-S26.
Topping et al., (1997). *The Journal of Nutrition* 127, 615-615.
Walker and Merritt, (1968). *Nature* 221, 482-484.
Wan and Lemaux, (1994). *Plant Physiology* 104, 37-48.
Wang et al., (1998). *Journal of Experimental Botany* 49, 481-502.
Wang, et al., (1993). *Cereal Chemistry* 70, 521-525.
Wegener et al., 1994. Mol. Gen. Genet. 245, 465-470.
Yamamori, (1998). (Anon.), pp. 300-302. University Extension Press, University of Saskatchewan, Saskatoon.
Yamamori and Endo, (1996). *Theoretical and Applied Genetics* 93, 275-281.
Yamamori et al., (2000). *Theor. Appl. Genet.* 101, 21-29
Young. (1984). in Whistler et al. (eds), Academic Press, Orlando, Fla., chap 8.
Zhang, et al. (1999). *Plant Cell Reports.* 18, 959-966.
Zikiryaeva and Kasimov, (1972). *Uzbekskii Biologicheskii Zhurnal* 6, 18-20.
Zwar and Chandler, (1995). *Planta* 197, 39-48.

---

The invention claimed is:

1. A process for making a food product, comprising
   a) obtaining barley grain comprising a genetic variation which reduces the activity of SBEIIa by 40%, and a reduced level of SBEIIa and SBEIIb proteins in its endosperm, relative to barley grain of the Golden Promise variety, and starch comprising amylose, wherein the amylose content of the starch as measured by an iodometric method is at least 40% (w/w) of total starch content of the barley grain,
   b) optionally processing the barley grain to produce milled, ground, pearled, rolled, kibbled or cracked grain, flour, wholemeal or starch therefrom, and
   c) including the barley grain of a), or the milled, ground, pearled, rolled, kibbled or cracked grain, flour, wholemeal or starch of b) as an ingredient in the food product, to thereby make the food product.

2. The process of claim 1, wherein the barley grain has a starch content of at least 25% (w/w).

3. The process of claim 2, wherein the barley grain has a starch content of at least 35% (w/w).

4. The process of claim 3, wherein the barley grain has a starch content of 45-50% (w/w).

5. The process of claim 1, wherein the barley grain has an average length to thickness ratio of less than 3.5.

6. The process of claim 1, wherein the barley grain has an average weight of at least 36 mg.

7. The process of claim 1, wherein the amylose content of the starch is at least 50% (w/w).

8. The process of claim 1, wherein the amylose content of the starch is at least 60% (w/w).

9. The process of claim 1, wherein the barley grain does not exhibit purple coloration.

10. The process of claim 1, wherein the barley grain comprises 3-6% (w/w) β-glucan as a percentage of total non-hulled grain weight.

11. The process of claim 1 wherein the barley grain is non-shrunken.

12. The process of claim 1, wherein the starch has an increased gelatinization temperature relative to starch from barley grain of the Golden Promise variety, as measured by differential scanning calorimetry.

13. The process of claim 1, wherein the food product is bread, cake, biscuits, noodles, quick soup or breakfast cereal.

14. A process for making a food product, comprising
   a) obtaining barley grain comprising a genetic variation which reduces the activity of SBEIIa by 40%, and a reduced level of SBEIIa and SBEIIb proteins in its endosperm, relative to barley grain of the Golden Promise variety, and starch comprising amylose, wherein the amylose content of the starch as measured by an iodometric method is at least 75% (w/w) of total starch content of the barley grain,
   b) optionally processing the barley grain to produce milled, ground, pearled, rolled, kibbled or cracked grain, flour, wholemeal or starch therefrom, and
   c) including the barley grain of a), or the milled, ground, pearled, rolled, kibbled or cracked grain, flour, wholemeal or starch of b) as an ingredient in the food product, to thereby make the food product.

15. A food product comprising barley grain which is wholegrain or milled, ground, pearled, rolled, kibbled or cracked grain, barley flour or barley wholemeal, wherein the barley grain, barley flour or barley wholemeal comprises a genetic variation which reduces the activity of SBEIIa by 40%, and a reduced level of SBEIIa and SBEIIb proteins in its endosperm, relative to barley grain, barley flour or barley wholemeal, respectively, of the Golden Promise variety of barley grain, and starch comprising amylose, wherein the amylose content of the starch as measured by an iodometric method is at least 40% (w/w) of total starch content of the barley grain, barley flour or barley wholemeal.

16. The food product of claim 15, wherein the food product is bread, cake, biscuits, noodles, quick soup or breakfast cereal.

17. The process of claim 1, wherein the barley grain comprises 6-8% (w/w) β-glucan as a percentage of total non-hulled grain weight.

* * * * *

SEQUENCE LISTING

```
<160> NUMBER OF SEQ ID NOS: 11

<210> SEQ ID NO 1
<211> LENGTH: 2554
<212> TYPE: DNA
<213> ORGANISM: Hordeum vulgare
<220> FEATURE:
<223> OTHER INFORMATION: SSBEIIa cDNA

<400> SEQUENCE: 1
ggcgagatgg cggaagtaaa catgacaggg ggggctgcag aaaaacttga atcttcagaa      60
ccgactcagg gtattgcgga aacaatcact gatggtgtaa ccaaaggagt taaagaacta     120
gtcgttgggg agaaaccgca agttgtccca aaaccaggag atgggcaaaa aatatacgag     180
attgacccaa cgctgaaaga ttttcggagc catcttgact accgatacag cgaatacaag     240
agaattcgtg ctgctattga ccaacatgaa ggtggattgg aagttttttc tcgtggttat     300
gaaaagcttg gatttacccg cagtgctaaa ggtatcactt accgagaatg ggctcctgga     360
gcgcattctg cagcattagt aggtgacttc aacaattgga acccaaatgc agatactatg     420
```

-continued

```
accagagatg attatggtgt ttgggagatt ttcctcccta caatgctga tggatcccct    480
gctattcctc atggctcacg tgtaaagata cggatggata ctccatctgg tgtgaaggat    540
tcaatttctg cttggatcaa gttctctgtg caggctccag gtgaaatacc attcaatggc    600
atatattatg atccacctga agaggagaag tatgtcttcc aacatcctca acctaaacga    660
ccagagtcac taaggatata tgaatcacac attggaatga gcagcccgga accgaagata    720
aattcatatg ctaattttag ggatgaggtg ctgccaagaa ttaaaaggct tggatacaat    780
gcagtgcaga taatggcaat ccaggagcat tcatactatg cgagctttgg gtaccatgtt    840
actaattttt ttgcaccaag tagccgtttt ggaactccag aggacttaaa atccttgatc    900
gatagagcac atgagcttgg tttgcttgtt cttatggata ttgttcatag tcattcgtca    960
aataatacccc ttgacggttt gaatggtttc gatggcactg atacacatta cttccacggt   1020
ggtccacgtg gccatcattg gatgtgggat tctcgtctgt tcaactatgg gagttgggaa   1080
gtattaagat tcttactgtc aaacgcgaga tggtggcttg aagaatataa gtttgatgga   1140
tttcgatttg atgggtgac ttccatgatg tatactcacc atggattaca aatgacattt   1200
actgggaact atggcgagta ttttggattc gccactgatg ttgatgcggt ggtttactta   1260
atgctggtca acgatctaat tcatggactt tatccggatg ctgtatccat tggtgaagat   1320
gtcagcggaa tgcctacatt tgcatccct gtcccagatg gtgggtgttgg ttttgactat   1380
cgcctgcata tggctgtagc agataaatgg attgaactcc tcaagcaaag tgacgaatct   1440
tggaaaatgg gcgatattgt gcacacccta acaaatagaa ggtggcttga aagtgtgtc   1500
acttatgcag aaagtcatga tcaagcacta gttggtgaca agactattgc attctggttg   1560
atggataagg atatgtatga tttcatggct ctggatagac cttcaacccc tcgcattgat   1620
cgtggcatag cattacataa aatgatcagg cttgtcacca tgggtttagg tggcgaaggc   1680
tatcttaatt tcatgggaaa tgagtttggg catcctgaat ggatagattt tccaagaggt   1740
ccgcaaactc ttccaaccgg caaagttctc cctggaaata acaatagtta tgataaatgc   1800
cgccgtagat ttgatcttgg agatgcagat tttcttagat atcgtggtat gcaagagttc   1860
gatcaggcaa tgcagcatct tgaggaaaaa tatgggttta tgacatctga gcaccagtat   1920
gtttctcgga acatgagga agataaggtg atcatcttcg aaagaggaga tttggtattt   1980
gttttcaact tccactggag caatagcaaa aaagactacc gtgttgggtg ttccaagcct   2040
gggaagtaca aggtggcctt agactctgat gatgcactct ttggtggatt cagcaggctt   2100
gatcatgatg tcgactactt cacaaccgaa catccgcatg acaacaggcc acgctctttc   2160
tcggtgtaca ctccgagcag aactgcggtc gtgtatgccc ttacagagta agaaccagca   2220
gctgtttgtt acaaggcaaa aagagaactc cagtgagctc gtggattgtg agcgaagcga   2280
cgggcaacgg tccgagactg ttctaaccgc cgtgattggg aggggatcgt gcctcttccc   2340
cagatgctag gaggatcaga tggataggta gcttgctggc gagccctcgt tttcaagtga   2400
cctgcgaaag aaaatggacg ggcctgggtg acattttgta gtgctgcact gaaccatcct   2460
atctctcaca ttcccggttg tttatgtaca tataaactaa taattgcccg tgcgcttcaa   2520
cttggacaaa aaaaaaaaaa aaaaaaaaa aaaa                                 2554
```

<210> SEQ ID NO 2
<211> LENGTH: 2780
<212> TYPE: DNA
<213> ORGANISM: Hordeum vulgare
<220> FEATURE:
<223> OTHER INFORMATION: SSBEIIb cDNA

```
<400> SEQUENCE: 2
ggcgagatgg cggcgccggc gttcgcagtt ccgcggcgg  ggatcgcccg gccatcggct      60
cgtcgatcca gcggggcaga gccgagatcg ctgctcttcg gccgcaacaa gggcacccgt     120
ttcccccgtg ccgtcggcgt cggaggttct gggtggcgcg tggtcatgcg cgcgggcggc     180
ccgtccgggg aggtgatgat ccctgacggc ggtagtggcg gaagcggaac accgccttcc     240
atcgagggtt ccgttcagtt cgagtctgat gatctggagg ttccattcat cgacgatgaa     300
ccaagcctgc acgatggagg tgaagatact attcggtctt cagagacata tcaggttact     360
gaagaaattg atgctgaagg cgtgagcaga atggacaaag aatcatccac ggtgaagaaa     420
atacgcattg tgccacaacc cggaaatgga cagcaaatat acgacattga cccaatgctc     480
cgagacttta agtaccatct tgagtatcga tacagcctat ataggagaat acgttcagac     540
attgatgaat acgatggagg catgatgtta ttttcccgcg gctacgagaa gtttggattt     600
gttcgcagcg ctgaaggtat cacttaccga gaatgggctc ctggagcaga ttctgcagca     660
ttagttggcg acttcaacaa ttgggatcca actgcagacc atatgagcaa aaatgacttg     720
ggtatttggg agattttcct gccaaacaat gcagatggtt cgccgccaat tcctcatggc     780
tcacgggtga aggtgcggat ggatactcca tctgggacaa aggattcaat tcctgcttgg     840
atcaagtact ccgtgcagac tccaggagat ataccataca atggaatata ttatgaccct     900
cctgaagagg agaagtatgt attcaagcat cctcaaccta acgaccaaa  atcattgcgg     960
atatatgaaa cacatgttgg catgagtagc ccggaaccaa agatcaacac atatgcaaac    1020
ttcagagatg aggtgcttcc aagaattaaa agacttggat acaatgcagt tcaaataatg    1080
gcaatccaag agcattcata ctatggaagc tttgggtacc atgttaccaa tttcttttgca   1140
ccaagtagcc gttttgggtc cccagaagat ttaaaatcct tgattgatag agctcacgag    1200
cttggtttgc ttgtcctgat ggatgttgtt cacagtcacg catcaagtaa taccttggac    1260
ggtttgaatg gttttgatgg cacggataca cattactttc atggcggctc acggggccat    1320
cactggatgt gggattctcg tgtgttcaac tacgggaata aggaagttat aaggtttcta    1380
cttttccaatg caagatggtg gctagaggaa tataagttcg atggtttccg attcgacggc    1440
gcgacctcca tgatgtatac ccaccatgga ttacaagtaa cctttacagg gagctaccat    1500
gaatattttg gctttgccac ggatgtagat gcagttgttt acttgatgct ggtgaatgat    1560
ctaattcacg cgctttatcc tgaagccgtt actattggtg aagatgttag tggaatgcct    1620
acatttgccc ttcctgttca gttggtgggg gttggttttg actatcgctt acatatggcc    1680
gttgccgata aatggattga acttctcaaa ggaagcgatg aaggttggga gatgggtaat    1740
attgtgcaca cactaacaaa tagaaggtgg ttggaaaagt gtgttactta tgctgaaagt    1800
catgatcaag cacttgttgg agacaagact attgcattct ggttgatgga caaggatatg    1860
tatgatttca tggctctgaa cggaccttcg acacctaata ttgatcgcgg aatagcactg    1920
cataaaatga ttagacttat cacaatggct ttaggaggag agggttatct taactttatg    1980
ggaaatgagt tcgggcatcc tgaatggata gactttccaa gaggcccaca agtacttcca    2040
actggtaagt tcatcccagg aaataacaac agttacgaca aatgccgtcg aagatttgac    2100
ctgggtgatg cagaatttct caggtatcat ggtatgcagc aatttgatca ggcaatgcag    2160
catcttgagg aaaaatatgg ctttatgaca tcagaccacc agtacgtatc tcggaaacac    2220
gaggaagata aggtgatcgt gtttgaaaaa ggggacttgg tatttgtgtt caacttccac    2280
tggagtaata gctatttcga ctaccgggtc ggttgcttaa agcctgggaa gtacaaggtg    2340
```

```
gtgttagact cagacgctgg actctttggt ggatttggta ggatccatca cactggagag    2400
cacttcacta atggctgcca acatgacaac aggccccatt cgttctcagt gtacactcct    2460
agcagaacct gtgttgtcta tgctccaatg aactaacagc aaagtgcagc atgcgcatgc    2520
gcgctgttgt tgcttagtag caacataaat cgtatggtca atacaaccag gtgcaaggtt    2580
taataaggtt tttttttttt tttttttttt tttttttttt tttttttttt ttttgcttca    2640
accagtcctg atagacaag acaacatgat gttgtgctgt gtgctcccaa tccccagggc    2700
gttgtgagga aaacatgctc atctgtgtta ccattttatg aatcagcaac gatacttctc    2760
ccaaaaaaaa aaaaaaaaa                                                  2780
```

<210> SEQ ID NO 3
<211> LENGTH: 11476
<212> TYPE: DNA
<213> ORGANISM: Aegilops tauschii
<220> FEATURE:
<221> NAME/KEY: MISC_FEATURE
<222> LOCATION: (1)...(11476)
<223> OTHER INFORMATION: n is a, c, g or t
<220> FEATURE:
<223> OTHER INFORMATION: SSBEIIa gene

<400> SEQUENCE: 3

```
agaaacacct ccatttaga ttttttttt gttcttttcg gacggtgggt cgtggagaga      60
ttagcgtcta gtttcttaa aagaacaggc catttaggcc ctgctttaca aaaggctcaa    120
ccagtccaaa acgtctgcta ggatcaccag ctgcaaagtt aagcgcgaga ccaccaaaac    180
aggcgcattc gaactggaca cgcgctcacg caggagccca gcaccacagg cttgagcctg    240
acagcggacg tgagtgcgtg acacatgggg tcatctatgg gcgtcggagc aaggaagaga    300
gacgcacatg aacaccatga tgatgctatc aggcctgatg gagggagcaa ccatgcacct    360
tttcccctct ggaaattcat agctcacact ttttttaat ggaagcaaga gttggcaaac    420
acatgcattt tcaaacaagg aaaattaatt ctcaaaccac catgacatgc aattctcaaa    480
ccatgcaccg acgagtccat gcgaggtgga aacgaagaac tgaaaatcaa catcccagtt    540
gtcgagtcga aagaggatg acactgaaag tatgcgtatt acgatttcat ttacatacat    600
gtacaaatac ataatgtacc ctacaatttg tttttggag cagagtggtg tggtcttttt    660
tttttacacg aaaatgccat agctggcccg catgcgtgca gatcggatga tcggtcggag    720
acgacggaca atcagacact caccaactgc ttttgtctgg gacacaataa atgtttttgt    780
aaacaaaata aatacttata aacgagggta ctagaggccg ctaacggcat ggccaggtaa    840
acgcgctccc agccgttggt ttgcgatctc gtcctcccgc acgcagcgtc gcctccaccg    900
tccgtccgtc gctgccacct ctgctgtgcg cgcgcacgaa gggaggaaga acgaacgccg    960
cacacacact cacacacggc acactccccg tgggtcccct ttccggcttg gcgtctatct   1020
cctctccccc gcccatcccc atgcactgca ccgtacccgc cagcttccac cccgccgca   1080 cacgttgctc cccttctca tcgcttctca attaatatct ccatcactcg ggttccgcgc   1140
tgcatttcgg ccggcgggtt gagtgagatc tgggcgactg gctgactcaa tcactacgcg   1200
gggatggcga cgttcgcggt gtccggcgcg actctcggtg tggcgcgggc cggcgtcgga   1260
gtggcgcggg ccggctcgga gcggaggggc ggggcggact gccgtcgct gctcctcagg   1320 aagaaggact cctctcgtac gcctcgctct ctcgaatctc ccccgtctgg ctttggctcc   1380
ccttctctct cctctgcgcg cgcatggcct gttcgatgct gttccccaat tgatctccat   1440
gagtgagaga gatagctgga ttaggcgatc gcgcttcctg aacctgtatt ttttcccccg   1500
```

```
cggggaaatg cgttagtgtc acccaggccc tggtgttacc acggctttga tcattcctcg    1560
tttcattctg atatatattt tctcattctt tttcttcctg ttcttgctgt aactgcaagt    1620
tgtggcgttt tttcactatt gtagtcatcc ttgcattttg caggcgccgt cctgagccgc    1680
gcggcctctc cagggaaggt cctggtgcct gacggcgaga gngacgactt ggcaagtccg    1740
gcgcaacctg aagaattaca ggtacacaca ctcgtgccgg taaatcttca tacaatcgtt    1800
attcacttac caaatgccgg atgaaaccaa ccacggatgc gtcaggtttc gagcttcttc    1860
tatcagcatt gtgcagtact gcactgcctt gttcattttg ttagccttgg ccccgtgctg    1920
gctcttgggc cactgaaaaa atcagatgga tgtgcattct agcaagaact tcacaacata    1980
atgcaccgtt tggggtttcg tcagtctgct ctacaattgc tattttttcgt gctgtagata    2040 cctgaagata tcgaggagca acggcggaa gtgaacatga caggggggac tgcagagaaa    2100
cttcaatctt cagaaccgac tcagggcatt gtggaaacaa tcactgatgg tgtaaccaaa    2160
ggagttaagg aactagtcgt gggggagaaa ccgcgagttg tcccaaaacc aggagatggg    2220
cagaaaatat acgagattga cccaacactg aaagattttc ggagccatct tgactaccgg    2280
taatgcctac ccgctgcttt cgctcatttt gaattaaggt cctttcatca tgcaaatttg    2340
gggaacatca aagagacaaa gactagggac caccatttca tacagatccc ttcgtggtct    2400
gagaatatgc tgggaagtaa atgtataatt gatggctaca atttgctcaa aattgcaata    2460
cgaataactg tctccgatca ttacaattaa agagtggcaa actgatgaaa atgtggtgga    2520
tgggttatag atttttacttt gctaattcct ctaccaaatt cctaggggg aaatctacca    2580 gttgggaaac ttagtttctt atctttgtgg cctttttgtt ttggggaaaa cacattgcta    2640
aattcgaatg attttgggta tacctcggtg gattcaacag atacagcgaa tacaagagaa    2700
ttcgtgctgc tattgaccaa catgaaggtg gattggaagc attttctcgt ggttatgaaa    2760
agcttggatt tacccgcagg taaatttaaa gctttattat tatgaaacgc ctccactagt    2820
ctaattgcat atcttataag aaaatttata attcctgttt tccctctct ttttcccagt    2880 gctgaaggta tcgtctaatt gcatatctta taagaaaatt tatattcctg tttcccccta    2940 tttccagtg ctgaaggtat cacttaccga gaatgggctc cctggagcgc atgttatgtt    3000
cttttaagtt cctaacgag acaccttcca atttattgtt aatggtcact attccaccaac    3060 tagcttactg gacttacaaa ttagcttact gaatactgac cagttactat aaatttatga    3120
tctggctttt gcaccctgtt acagtctgca gcattagtag gtgacttcaa caattggaat    3180
ccaaatgcag atactatgac cagagtatgt ctacagcttg gcaattttcc accttttgctt    3240 cataactact gatacatcta tttgtattta tttagctgtt tgcacattcc ttaaagttga    3300
gcctcaacta catcatatca aaatggtata atttgtcagt gtcttaagct tcagcccaaa    3360
gattctactg aatttagtcc atctttttga gattgaaaat gagtatatta aggatgaatg    3420
aatacgtgca acactcccat ctgcattatg tgtgcttttc catctacaat gagcatattt    3480
ccatgctatc agtgaaggtt tgctcctatt gatgcagata tttgtatatgg tcttttcagg    3540 atgattatgg tgtttgggag attttcctcc ctaacaacgc tgatggatcc tcagctattc    3600
ctcatggctc acgtgtaaag gtaagctggc caattattta gtcgaggatg tagcattttc    3660
gaactctgcc tactaagggt cccttttcct ctctgttttt tagatacgga tggatactcc    3720
atccggtgtg aaggattcaa tttctgcttg gatcaagttc tctgtgcagg ctccaggtga    3780
aatacctttc aatggcatat attatgatcc acctgaagag gtaagtatcg atctacatta    3840
cattattaaa tgaaatttcc agtgttacag ttttttaata cccacttctt actgacatgt    3900
```

```
gagtcaagac aatacttttg aatttggaag tgacatatgc attaattcac cttctaaggg    3960
ctaaggggca accaaccttg gtgatgtgtg tatgcttgtg tgtgacataa gatcttatag    4020
ctcttttatg tgttctctgt tggttaggat attccatttt ggccttttgt gaccatttac    4080
taaggatatt tacatgcaaa tgcaggagaa gtatgtcttc caacatctca actaaacgac    4140
cagagtcact aaggatttat gaatcacaca ttggaatgag cagcccggta tgtcaataag    4200
ttatttcacc tgtttctggt ctgatggttt attctatgga ttttctagtt ctgttatgta    4260
ctgttaacat attacatggt gcattcactt gacaacctcg attttatttt ctaatgtctt    4320
catattggca agtgcaaaac tttgcttcct ctttgtctgc ttgttctttt gtcttctgta    4380
agatttccat tgcatttgga ggcagtgggc atgtgaaagt catatctatt ttttttttgt    4440
cagagcatag ttatatgaat tccattgttg ttgcaatagc tcggtataat gtaaccatgt    4500
tactagctta agatttccca cttaggatgt aagaaatatt gcattggagc gtctccagca    4560
agccatttcc taccttatta atgagagaga gacaaggggg ggggggggg ggggttccc     4620 ttcattattc tgcgagcgat tcaaaaactt ccattgttct gaggtgtacg tactgcaggg    4680
atctcccatt atgaagagga tatagttaat tctttgtaac ctacttggaa acttgagtct    4740
tgaggcatcg ctaatatata ctatcatcac aatacttaga ggatgcatct gaanattta    4800 gtgtgatctt gcacaggaac cgaagataaa ttcatatgct aatttaggg atgaggtgtt     4860 gccaagaatt aaaaggcttg gatacaatgc agtgcagata atggcaatcc aggagcattc    4920
atactatgca agctttgggt attcacacaa tccatttttt tctgtataca cntcttcacc    4980
catttggagc tattacatcc taatgcttca tgcacataaa atatttggat ataatccttt    5040
attagatata tagtacaact acacttagta ttctgannaa naagatcatt ttattgttgt    5100
tggcttgttc caggtaccat gttactaatt ttttgcacc aagtagccgt tttggaactc     5160
cagaggactt aaaatccttg atcgatagag cacatgagct tggtttgctt gttcttatgg    5220
atattgttca taggtaatta gtccaattta attttagctg ttttactgtt tatctggtat    5280
tctaagggga aattcaggca attatgatac attgtcaaaa gctaagagtg gcgaaagtga    5340
aatgtcaaaa tctagagtgg cataaggaaa attggcaaaa actagagtgg caaaaataaa    5400
attttcccat cctaaatggc agggccctat cgccgaatat ttttccattc tatataattg    5460
tgctacgtga cttctttttt ctcagatgta ttaaaccagt tggacatgaa atgtatttgg    5520
tacatgtagt aaaactgacag ttccatagaa tatcgttttg taatggcaac acaatttgat    5580
gccatagatg tggattgaga agttcagatg ctatcaatag aattaatcaa ctggccatgt    5640
actcgtggca ctacatatag tttgcaagtt ggaaaactga cagcaatacc tcactgataa    5700
gtggccaggc cccacttgcc agcttcatac tagatgttac ttccctgttg aattcatttg    5760
aacatattac ttaaagttct tcatttgtcc taagtcaaac ttctttaagt ttgaccaagt    5820
ctattggaaa atatatcaac atctacaaca ccaaattact ttgatcagat taacaatttt    5880
tattttatta tattagcaca tctttgatgt tgtagatatc agcacatttt tctatagact    5940
tggtcaaata tagagaagtt tgacttagga caaatctaga acttcaatca atttggatca    6000
gagggaacat caaataatat agatagatgt caacacttca acaaaaaaat cagaccttgt    6060
caccatatat gcatcagacc atctgtttgc tttagccact tgctttcata tttatgtgtt    6120
tgtacctaat ctacttttcc ttctacttgg tttggttgat tctatttcag ttgcattgct    6180
tcatcaatga ttttgtgtac cctgcagtca ttcgtcaaat aatacccttg acggtttgaa    6240
tggtttcgat ggcactgata cacattactt ccacggtggt ccacgcggcc atcattggat    6300
```

```
gtgggattct cgtctattca actatgggag ttgggaagta tgtagctctg acttctgtca    6360
ccatatttgg ctaactgttc ctgttaatct gttcttacac atgttgatat tctattctta    6420
tgcaggtatt gagattctta ctgtcaaacg cgagatggtg gcttgaagaa tataagtttg    6480
atggatttcg atttgatggg gtgacctcca tgatgtatac tcaccatgga ttacaagtaa    6540
gtcatcaagt ggtttcagta acttttttag ggcactgaaa caattgctat gcatcataac    6600
atgtatcatg atcaggactt gtgctacgga gtcttagata gttccctagt atgcttgtac    6660
aattttacct gatgagatca tggaagattg gaagtgatta ttatttattt tctttctaag    6720
tttgtttctt gttctagatg acatttactg ggaactatgg cgaatatttt ggatttgcta    6780
ctgatgttga tgcggtagtt tacttgatgc tggtcaacga tctaattcat ggactttatc    6840
ctgatgctgt atccattggt gaagatgtaa gtgcttacag tatttatgat ttttaactag    6900
ttaagtagtt ttattttggg gatcagtctg ttacactttt tgttaggggt aaaatctctc    6960
ttttcataac aatgctaatt tataccttgt atgataatgc atcacttang taatttgaaa    7020
agtgcaaggg cattcaagct tacgagcata ttttttgatg gctgtaattt atttgatagt    7080
atgcttgttt gggttttttca ataagtggga gtgtgtgact aatgttgtat tatttattta    7140
attgcggaag aaatgggcaa ccttgtcaat tgcttcagaa ggctaacttt gattccataa    7200
acgctttgga aatgagaggc tattcccaag gacatgaatt atacttcagt gtgttctgta    7260
catgtatttg taatagtggt ttaacttaaa ttcctgcact gctatggaat ctcactgtat    7320
gttgtnagtg tacacatcca caaacaagta atcctgagct ttcaactcat gagaaaatan    7380
gangtccgct tctgccagca ttaactgttc acagttctaa tttgtgtaac tgtgaaattg    7440
ttcaggtcag tggaatgcct acattttgca tccctgttcc agatggtggt gttggttttg    7500
actaccgcct gcatatggct gtagcagata aatggattga actcctcaag taagtgcagg    7560
aatattggtg attacatgcg cacaatgatc tagattacat tttctaaatg gtaaaaagga    7620
aaatatgtat gtgaatatct agacatttgc ctgttatcag cttgaatacg agaagtcaaa    7680
tacatgattt aaatagcaaa tctcggaaat gtaatggcta gtgtctttat gctgggcagt    7740
gtacattgcg ctgtagcagg ccagtcaaca cagttagcaa tattttcaga aacaatatta    7800
tttatatccg tatatganga aagttagtat ataaactgtg gtcattaatt gtgttcacct    7860
tttgtcctgt ttaaggatgg gcagtaggta ataaatttag ccagataaaa taaatcgtta    7920
ttaggtttac aaaaggaata tacagggtca tgtagcatat ctagttgtaa ttaatgaaaa    7980
ggctgacaaa aggctcggta aaaaaaactt tatgatgatc cagatagata tgcaggaacg    8040
cgactaaagc tcaaatactt attgctacta cacagctgcc aatctgtcat gatctgtgtt    8100
ctgctttgtg ctatttagat ttaaatacta actcgataca ttggcaataa taaacttaac    8160
tattcaacca atttggtgga taccaganat ttctgccctc ttgttagtaa tgatgtgctc    8220
cctgctgctg ttctctgccg ttacaaaagc tgttttcagt tttttgcatc attattttg    8280 tgtgtgagta gtttaagcat gtttttttgaa gctgtgagct gttggtactt aatacattct    8340
tggaagtgtc caaatatgct gcagtgtaat ttagcatttc tttaacacag gcaaagtgac    8400
gaatcttgga aaatgggcga tattgtgcac accctaacaa atagaaggtg gcttgagaag    8460
tgtgtaactt atgcagaaag tcatgatcaa gcactagttg gtgacaagac tattgcattc    8520
tggttgatgg ataaggtact agctgttact tttggacaaa agaattactc cctcccgttc    8580
ctaaatataa gtctttgtag agattccact atggaccaca tagtatatag atgcatttta    8640
gagtgtagat tcactcattt tgcttcgtat gtagtccata gtgaaatctc tacagagact    8700
```

```
tatatttagg aacggaggga gtacataatt gatttgtctc atcagattgc tagtgttttc   8760
ttgtgataaa gattggctgc ctcacccatc accagctatt tcccaactgt tacttgagca   8820
gaatttgctg aaaacgtacc atgtggtact gtggcggctt gtgaactttg acagttatgt   8880
tgcaattttc tgttcttatt tatttgattg cttatgttac cgttcatttg ctcattcctt   8940
tccgagacca gccaaagtca cgtgttagct gtgtgatctg ttatctgaat cttgagcaaa   9000
ttttattaat aggctaaaat ccaacgaatt atttgcttga atttaaatat acagacgtat   9060
agtcacctgg ctctttctta gatgattacc atagtgcctg aaggctgaaa tagttttggt   9120
gtttcttgga tgccgcctaa aggagtgatt tttattggat agattcctgg ccgagtcttc   9180
gttacaacat aacattttgg agatatgctt agtaacagct ctgggaagtt tggtcacaag   9240
tctgcatcta cacgctcctt gaggttttat tatggcgcca tctttgtaac tagtggcacc   9300
tgtaaggaaa cacattcaaa aggaaacggt cacatcattc taatcaggac caccatacta   9360
agagcaagat tctgttccaa ttttatgagt tttgggact ccaaagggaa caaaagtgtc    9420
tcatattgtg cttataacta cagttgtttt taccagtg tagttttatt ccaggacagt     9480
tgatacttgg tactgtgctg taaattattt atccgacata aacagcatg aacatatcaa    9540
gctctctttg tgcaggatat gtatgatttc atggctctgg ataggcttca actcttcgca   9600
ttgatcgtgg catagcatta cataaaatga tcaggcttgt caccatgggt ttaggtggtg   9660
aaggctatct taacttcatg ggaaatgagt ttgggcatcc tggtcagtct ttacaacatt   9720
attgcattct gcatgattgt gatttactgt aatttgaacc atgcttttct ttcacattgt   9780
atgtattatg taatctgttg cttccaagga ggaagttaac ttctatttac ttggcagaat   9840
ggatagattt tccaagaggc ccacaaactc ttccaaccgg caaagttctc ccctggaaat   9900
aacaatagtt atgataaatg ccgccgtaga tttgatcttg taagttttag ctgtgctatt   9960
acattccctc actagatctt tattggccat ttatttcttg atgaaatcat aatgtttgtt  10020
aggaaagatc aacattgctt ttgtagtttt gtagacgtta acataagtat gtgttgagag  10080
ttgttgatca ttaaaaatat catgattttt tgcagggaga tgcagatttt cttagatatc  10140
gtggtatgca agagttcgat caggcaatgc agcatcttga ggaaaaatat ggggtatgtc  10200
actggtttgt ctttgttgca taacaagtca cagtttaacg tcagtctctt caagtggtaa  10260
aaaaagtgta gaattaattc ctgtaatgag atgaaaactg tgcaaaggcg gagctggaat  10320
tgcttttcac caaaactatt ttcttaagtg cttgtgtatt gatacatata ccagcactga  10380
caatgtaact gcagtttatg acatctgagc accagtatgt ttcacggaaa catgaggaag  10440
ataaggtgat catcctcnaa aagaggagat ttggtatttg ttttcaactt ccactgagc   10500
aatagctttt ttgactaccg tgttgggtgt tccaagcctg ggaagtacaa ggtatgcttg  10560
ccttttcatt gtccaccctt caccagtagg gttagtgggg gcttctacaa cttttaattc  10620
cacatggata gagtttgttg gtcgtgcagc tatcaatata aagaataggg taatttgtaa  10680
agaaaagaat ttgctcgagc tgttgtagcc ataggaaggt tgttcttaac agccccgaag  10740
cacataccat tcattcatat tatctactta agtgtttgtt tcaatcttta tgctcagttg  10800
gactcggtct aatactagaa ctattttccg aatctaccct aaccatccta gcagttttag  10860
agcagcccca tttggacaat tggctgggtt tttgttagtt gtgacagttt ctgctatttc  10920
ttaatcaggt ggccttggac tctgacgatg cactctttgg tggattcagc aggcttgatc  10980
atgatgtcga ctacttcaca accgtaagtc tgggctcaag cgtcacttga ctcgtcttga  11040
ctcaactgct tacaaatctg aatcaacttc ccaattgctg atgcccttgc aggaacatcc  11100
```

```
gcatgacaac aggccgcgct ctttctcggt gtacactccg agcagaactg cggtcgtgta   11160
tgcccttaca gagtaagaac cagcagcggc ttgttacaag gcaaagagag aactccagag   11220
agctcgtgga tcgtgagcga agcgacgggc aacggcgcga ggctgctcca agcgccatga   11280
ctgggagggg atcgtgcctc ttccccagat gccaggagga gcagatggat aggtagcttg   11340
ttggtgagcg ctcgaaagaa aatggacggg cctgggtgtt tgttgtgctg cactgaaccc   11400
tcctcctatc ttgcacattc ccggttgttt ttgtacatat aactaataat tgcccgtgcg   11460
ctcaacgtga aaatcc                                                   11476

<210> SEQ ID NO 4
<211> LENGTH: 6550
<212> TYPE: DNA
<213> ORGANISM: Aegilops tauschii
<220> FEATURE:
<221> NAME/KEY: MISC_FEATURE
<222> LOCATION: (1)...(6550)
<223> OTHER INFORMATION: n is a, c, g or t
<220> FEATURE:
<223> OTHER INFORMATION: partial SSBEIIb gene

<400> SEQUENCE: 4
aagctttgta gccttgcacg ggctccccaa caaactgcct cactcgattg tcaaaaaagt     60
aaaaatgatt gtagaaaaaa aaactgactc actcgtcact accctaccgt cctacatgac    120
acctggccgc aagacgacgc cgtcctcctg ccgcgcgcgt ccgcgatcac accaccgcaa    180
aaaccaaaac ctcttcgccg gtgcgtccca cgctaccatc catgcagccg tccgcccgcg    240
cgcgcgttgc ccgcaccacc cgctggcggc caccacgccg ccactctcgc gtgaaggctc    300
cgtccgcttc ctcctagttc cactctctct ccgtgctagc agtatatagc atccgccctc    360
cgccccctcc caatcttaga acacccctcc ctttgcctcc tcatttcgct cgcgtgggtt    420
taagcaggag acgaggcggg gtcagttggg cagttaggtt ggatccgatc cggctgcggc    480
ggcggcgacg ggatggctgc gccggcattc gcagtttccg cggcggggct ggcccggccg    540
tcggctcctc gatccggcgg ggcagagcgg aggggcgcg gggtggagct gcagtcgcca    600
tcgctgctct tcggccgcaa caagggcacc cgttcacccc gtaattattt gcgccacctt    660
tctcactcac attctctcgt gtattctgtc gtgctcgccc ttcgccgacg acgcgtgccg    720
attccgtatc gggctgcggt gttcagcgat cttacgtcgg ttccctcctg gtgtggtgat    780
gtctgtaggt gccgtcggcg tcggaggttc tggatggcgc gtggtcatgc gcgcggggg    840 gccgtccggg gaggtgatga tccctgacgg cggtagtggc ggaacaccgc cttccatcga    900
cggtcccgtt cagttcgatt ctgatgatct gaaggtagtt tttttttttgc atcgatctga    960 aggtacttga catatactac tgtattaccc tgagtaaata ctgccaccat atttttatgg   1020
ttcgcttgaa ataccctgtttt acttgctacg gttttcactt tcattgagac gtcggacgaa   1080
attcactgaa ttcctataat ttggtagaca ccgaaatata tactactcct tccgtcccat   1140
aatataagag cgttttttggc acctatatt ataggggcgga gggagtacct tttaggtcaa   1200
aatattgtgg tagtttcaat tgtatacaag aattcaaata tttttttttaa aaaaaaatca   1260 actaattggt tgagtttcaa gtgaagcgtt ttggtccttt ggctgagatg taaaccgaaa   1320
tcactgaaat tcatagtagc cgaaacttta atagaactga aactcaaaat ctgctatccg   1380
gcgaaattct aaagatttgc ttatttcaca cgtaggttgc agtacaccct ctttctaatt   1440
tattggggaa ggggtattat tatcttgtta gtacctgcct gcatgacaat tgaaatctaa   1500
gacaaaacac catatgcgag gcctacacac ggtaggttgg tttacaacta tgtgtgccac   1560
```

```
agttcgtctg aacttttttgt ccttcacatc gtgttaggtt ccattcattg atgatgaaac      1620
aagcctacag gatggaggtg aagatagtat ttggtcttca gagacaaatc aggttagtga      1680
agaaattgat gctgaagaca cgagcagaat ggacaaagaa tcatctacga gggagaaatt      1740
acgcattctg ccaccaccgg gaaatggaca gcaaatatac gagattgacc caacgctccg      1800
agactttaag taccatcttg agtatcggta tgcttcgctt ctattgtgtg cactttaaaa      1860
acaatttaca gtctttgata agatgtgaat ggctgcttgc tgtgacacga aactcttgaa      1920
gttcgtagtc actcttgtgt gttcatggtt ctgaggtaac atggtaaccg aacaaaaata      1980
ggaaagtggc aagcactgca atgtgagcta ctgataacca cccattgtaa ttgggtacac      2040
tgattaatat atatgtcttc atgggctcta ttttttttca atatctatgc caattgaaca      2100
acaatgcttt gtggacgggt gttcttttac cctcttcttc tatcaataga tgatatgcat      2160
actcatgcgt atcctacaaa aaattgaaca acaatgccac tttcccccgt gttgcttttg      2220
taaggatgaa acacatatgt ccagatcaaa ctatactagc agtctaactg tgccttaatg      2280
gatcaaaaac agatatagcc tatacaggag aatacgttca gacattgatg aacacgaagg      2340
aggcatggat gtatttttccc gcggttacga gaagtttgga tttatgcgca ggtgaaattt      2400
cttgactaaa taactatgta tctacctttt ctttgtactc tatcaacatt cctcttccca      2460
tgcagcgctg aaggtatcac ttaccgagaa tgggctcctg gagcagatgt acgttcttct      2520
aaccatctga tcgtttacct gactatacta attctatctt tcaactaatt gtgaataatt      2580
actgctcatc agctatccta aggttgggga ttttgcacct cccagatgaa cagcatatta      2640
agtcgcacaa ctagcattat taagaactaa ctcctgcttc caattgcagt ctgcagcatt      2700
agttggcgac ttcaacaatt gggatccaaa tgcagaccat atgagcaaag tatgcatgta      2760
gtttcacaaa tatatcatat tttctttgta gattttttttt tttagatcgg cttatctatt      2820
taaatgtggt tgaatataca ccttatatgt acgttgagct gtaaatatag ttggaagtgt      2880
ttaggagtat taaattcact ggactctatt ctttcacttg cctgttgcac gagcccatta      2940
ctagatatca atgttgatga tgcttttgtt gtatgaggtc gaagtgaaac atgcatgtta      3000
cccttttata taagtaaggt tgcacatgta tttttttatga tctaaacatt atttactgat      3060
tttgttcttg caagcactaa agcagttttta cataataatg gcgttggagc aggccgactg      3120
cacatctgaa ctgtagctcc atgtggttga tatagattac aaatgctcat attcaatgta      3180
actgttttca gaatgacctt ggtgtttggg agattttttct gccaaacaat gcagatggtt      3240
cgccaccaat tcctcacggc tcacgggtga aggttgtttt cttctccttg ccaacggtgt      3300
taggctcagg aacatgtcct gtattactca gaagctcttt tgaacatcta ggtgagaatg      3360
gatactccat ctgggataaa ggattcaatt cctgcttgga tcaagtactc cgtgcagact      3420
ccaggagata taccatacaa tggaatatat tatgatcctc ccgaagaggt attttacttc      3480
atcttctgtg cttttagatt tcagatattt ttattagaag aaaattatga ttttttccct      3540
cacgaacctt cccaattgct atttcaagct gtcctactta tttgctgctg gcatcttatt      3600
tttctattct ctaaccagtt atgaaattcc ttacatgcat atgcaggaga agtatgtatt      3660
caagcatcct caacctaaac gaccaaaatc attgcggata tatgaaacac atgttggcat      3720
gagtagcccg gtatttcatc tttaccatgt attccataaa tgaagttagc tatatgcagt      3780
tcaaatttat ttacaggttg ttacaatggt atttttgtgt tggtgcccctt ctttcgtttt      3840 ataagtaaaa aacttatcat aaatttattt gttatgccgc ttggttaata caatctgaaa      3900
aatgtaactg tggacaatct agaactagat aatacaaatc tgaaaaaaca tgctggaata      3960
```

```
gtgtcatttc agtcaactag gatgttttga atgctcaaga gaagtactag tgtgtagcat    4020
caaaagctgg tgtccatttg ttcaaatgtt taattaacac tatagtgaaa acaagtaatt    4080
gcacaaagaa acaagtaatt gcccaagttc atatgttttt tcactatatt acatgtttca    4140
tcaacaattt aattaacctc attccttaca aacatttgta tttacatttg ttcctacata    4200
tatagttatt ttatatatca actttataaa tcatgactgt tataattaaa accgatggta    4260
tatcaacgat tgagataatt tggcatatgt ggatgaattt tgtggcttgt tatgctcttg    4320
ttttaataac ataataaata gattatgctt gttggtagcc ttttttacatt aacacatggg    4380 caattacttg tttctttgtg caaccaggaa ccaaagatcg acacatatgc aaacttcagg    4440
gatgaggtgc ttccaagaat taaaagactt ggatacaatg cagtgcaaat aatggcaatc    4500
caagagcact catactatgg aagctttggg tagttctctg ggtcgatttc tggttctttt    4560
agttatcttt tgtccataga acatatttca actttagcaa ctatactatt atattaactt    4620
ttcagctatt gtcttncttt ttcttatgtg agagactgct gcntcttgct acttcctgtg    4680
ttctcattca gagtanacat cttatganta gacaactcta tgtngacatt ccggaagtat    4740
ncactggctg attcggtcta aaataacata ctgctcagat agccacataa cagtacgatt    4800
acacacataa tgaccatgtt tgcatagagt ggcggtagta tgttcctcac catactagca    4860
taatgacttg ttatataaga gtatatcata ttaacttctt ttccaatgac atggaagctg    4920
taacaacttt caaatcattt tgtcttttta agtgctgctt ttttcctgtt tgacaattaa    4980
tacaatacca cttttatgtg tttttacttc tattgcaggt accatgttac caatttcttt    5040
gcaccaagta gccgttttgg gtccccagaa gatttaaaat ctttgattga tagagctcac    5100
gagcttggct tggttgtcct catggatgtt gttcacaggt acttaatgta atttgaggtt    5160
ggcgtgttaa gttcacatta atcttaattc tttatttcaa ttcctatggc ctctctccta    5220
gattggaaca gtaaaagcat catccagttt gtataaattg ctaaaagaac attttacatg    5280 ttaagtatttt tcaattacta tgaaacatat aaatttacat acttattgat tttacgacag    5340
aagtaccgat ctcacaagat gaacaattgg ttgatcacat atcatttcat actacaatac    5400
aagaaaatga atagagaacg agttaatatt agccttggta aaatcagcaa cttgtttgga    5460
aataaagtat agtgatgcca gtgcaaanaa caaggcatca agttggtttc agctcccacg    5520
gtcggtgcta gctgtcaagg gtaatttgca cgtagtcgca catagatttg tgtgggagtg    5580
gaaagtaacc acagattgtc cgaggaacac gggacacacg tcttagccac aggtttgggc    5640
tccccttgat gcgggtagta gctttactcc ttatatgaaa ttatctcaag atagatttca    5700
atttggggtt acacttanga actcancaag ttaaggatca actcnctgag ttctatacga    5760
ctgatctttg accgagatat cttgatcagg ctaagtanca aaatccaggc cttgagatgt    5820
tgaacatgtc cttcattttg ggctgggtgc ccttgggcat aaggtgtngt ccttccttca    5880
tgtgcttctt gcagcgtatg acataaacnt cctctgagtt ggtanatgca cggttccctt    5940
tgaggaaatc aggggtagtc gcatctnggg aaagttggtc acccangcat ggatcctcng    6000
cgcacaccgg gcaaacacgg tgaaaccact tctcctcgac actagctaac ttgacattca    6060
agcaaactaa gaatataact ttatntctaa atgaaccgga caccctcctt gtgcctgcac    6120
ctacagagta caatgccagt tttggactga actcttgtgt tcatgtatgt gctaatncaa    6180
taggttctaa ccatgattct aaatagcgcg ttataactcc actatagtaa tgctatagcg    6240
tttanaagat cccgcactaa gggacccttag tccaaatcaa tgatcaaaca ttttacatag    6300
cgcgctatag ctatttaaaa ctatggtcac ccgctaagag gcataactcg ctatttaaaa    6360
```

-continued

```
ctatggttct aacttttaat ctattttatg tcttggtcca aagccccttt ttgttctata    6420
gctttacctt tgggttgaga tcacccttaa cccattggta atcctggttg atttactcca    6480
tcctttcttg cgtagcttta cttttggttt tttgtttctc acagtcacgc gtcaaataat    6540
accttggacg                                                          6550

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 5
caaccatgtc ctgaaccttc acc                                             23

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 6
ggtaccccat ctcctggttt tgggacaac                                       29

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 7
ggtaccgtcc atttcccggt ggtggca                                         27

<210> SEQ ID NO 8
<211> LENGTH: 18
<212> TYPE: PRT
<213> ORGANISM: Artificial Sequence
<220> FEATURE:
<223> OTHER INFORMATION: fragment of N-terminus of SBEIIa protein

<400> SEQUENCE: 8

Ala Ala Ser Pro Gly Lys Val Leu Val Pro Asp Glu Ser Asp Asp
1               5                   10                  15

Leu Gly Cys

<210> SEQ ID NO 9
<211> LENGTH: 12
<212> TYPE: PRT
<213> ORGANISM: Artificial Sequence
<220> FEATURE:
<223> OTHER INFORMATION: fragment of N-terminus of SBEIIb protein

<400> SEQUENCE: 9

Ala Gly Gly Pro Ser Gly Glu Val Met Ile Gly Cys
1               5                   10

<210> SEQ ID NO 10
<211> LENGTH: 20
<212> TYPE: DNA
<213> ORGANISM: Artificial Sequence
<220> FEATURE:
<223> OTHER INFORMATION: Oligonucelotide Primer
```

```
<400> SEQUENCE: 10
acgaagatgc tctgcctcac                                              20

<210> SEQ ID NO 11
<211> LENGTH: 20
<212> TYPE: DNA
<213> ORGANISM: Artificial Sequence
<220> FEATURE:
<223> OTHER INFORMATION: Oligonucelotide Primer

<400> SEQUENCE: 11
gtccaacatc atagccattt                                              20
```